US008475808B2

(12) United States Patent
Andrews et al.

(10) Patent No.: US 8,475,808 B2
(45) Date of Patent: Jul. 2, 2013

(54) IMMUNOGENIC REAGENTS FROM WEST NILE VIRUS

(75) Inventors: William Andrews, Oakland, CA (US); David Chien, Alamo, CA (US); Qui-Lim Choo, El Cerrito, CA (US); Stephen Coates, Orinda, CA (US); Doris Coit, Petaluma, CA (US); Charles Harrington, Davis, CA (US); Susan Hilt, Vacaville, CA (US); Michael Houghton, Danville, CA (US); Angelica Medina-Selby, San Francisco, CA (US); Sergio Pichuantes, El Cerrito, CA (US); Yiu-Lian Fong, Lafayette, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 498 days.

(21) Appl. No.: 10/557,427

(22) PCT Filed: May 21, 2004

(86) PCT No.: PCT/US2004/015976
§ 371 (c)(1),
(2), (4) Date: Nov. 27, 2006

(87) PCT Pub. No.: WO2004/112694
PCT Pub. Date: Dec. 29, 2004

(65) Prior Publication Data
US 2007/0092538 A1  Apr. 26, 2007

Related U.S. Application Data

(60) Provisional application No. 60/473,225, filed on May 23, 2003, provisional application No. 60/529,171, filed on Dec. 11, 2003.

(51) Int. Cl.
*A61K 39/12* (2006.01)
*C12Q 1/70* (2006.01)
*C12N 15/86* (2006.01)

(52) U.S. Cl.
USPC ............ 424/218.1; 435/69.1; 435/5; 435/7.1; 530/350

(58) Field of Classification Search
None
See application file for complete search history.

(56) References Cited

U.S. PATENT DOCUMENTS

| | | | |
|---|---|---|---|
| 5,695,930 A * | 12/1997 | Weinstein et al. | 435/5 |
| 5,895,651 A * | 4/1999 | Simmons et al. | 424/192.1 |
| 7,556,812 B2 | 7/2009 | Tangy et al. | |
| 2004/0037848 A1* | 2/2004 | Audonnet et al. | 424/199.1 |

FOREIGN PATENT DOCUMENTS

| | | |
|---|---|---|
| CA | 2432738 | 6/2003 |
| CA | 2420092 | 8/2004 |
| EP | 1935991 A2 | 6/2008 |
| WO | WO 01/39802 | 6/2001 |
| WO | WO 02/072036 A2 | 9/2002 |
| WO | WO 02/081621 | 10/2002 |
| WO | WO03/062408 | 7/2003 |
| WO | WO2004/076619 | 9/2004 |

OTHER PUBLICATIONS

Colombage et al. Virology, 1998, vol. 250, p. 151-163.*
Davis et al. (Journal of Virology, 2001, vol. 75, p. 4040-4047).*
Lanciotti et al. (Science 1999, vol. 286, p. 2333-2337).*
Database WPI Week 200218 Thomson Scientific, London, GB; AN 2002-134491 & JP 2001 299336 A (Konishi E) Oct. 30, 2001.
Office Action dated Jan. 8, 2009 for Israeli patent application No. 171949 (translation).
Blitvich et al., "Epitope-Blocking Enzyme-Linked Immunosorbent Assays for Detection of West Nile Virus Antibodies in Domestic Mammals," Journal of Clinical Microbiology, 41(6):2676-2679, 2003.
Chang et al., "*Flavivirus* DNA Vaccines: Current Status and Potential," Annals New York Academy of Sciences, 951:272-285, 2001.
Chang et al., "Recent Advancement in *Flavivirus* Vaccine Development," Expert Rev. Vaccines, 3(2):199-220, 2004.
Davis et al.,"West Nile Virus Recombinant DNA Vaccine Protects Mouse and Horse from Virus Challenge and Expresses In Vitro a Noninfectious Recombinant Antigen That Can Be Used in Enzyme-Linked Immunosorbent Assays," Journal of Virology, 75(9):4040-4047, 2001.
Johnson et al., "Detection of Anti-Arboviral Immunoglobulin G by Using a Monoclonal Antibody-Based Capture Enzyme-Linked Immunosorbent Assay," Journal of Clinical Microbiology, 38(5):1827-1831, 2000.
Lanciotti et al.,"Origin of the West Nile Virus Responsible for an Outbreak of Encephalitis in the Northeastern United States." Science, 286:2333-2337, 1999.
Malan et al.. "Evaluations of Commercial West Nile Virus Immunoglobulin G (IgG) and IgM Enzyme Immunoassays Show the Value of Continuous Validation," Journal of Clinical Microbiology, 42(2); 727-733, 2004.
Martin et al., "Standardization of Immunoglobulin M Capture Enzyme-Linked Immunosorbent Assays for Routine Diagnosis of Arboviral Infections," Journal of Clinical Microbiology,38(5):1823-1826,2000.
Monath et al., "West Nile Virus Vacines," Current Drug Targets-Infectious Disorders, 1:37-50, 2001.
Tesh et al., "Efficacy of Killed Virus Vacccine, Live Attenuated Chimeric Virus Vaccine, and Passive Immunization for Prevention of West Nile Virus Encephalitis in Hamster Model," Emerging Infectious Diseases, 8(12):1392-1397, 2002.

(Continued)

*Primary Examiner* — Agnieszka Boesen
(74) *Attorney, Agent, or Firm* — Helen Lee; Roberta L. Robins

(57) ABSTRACT

Recombinant production of immunogenic West Nile Virus (WNV) proteins is described. These proteins, heterodimers comprising the proteins, fusions thereof, polynucleotides encoding the proteins, and combinations thereof, as well as antibodies produced therefrom, can be used in immunogenic compositions for preventing, treating and diagnosing WNV infection. Also described are highly sensitive ELISA and strip immunoassay methods for detecting the presence of WNV in biological samples.

38 Claims, 32 Drawing Sheets

OTHER PUBLICATIONS

Wengler et al., "Cell-Associated West Nile *Flavivirus* Is Covered with E+Pre-M Protein Heterodimers Which Are Destroyed and Reorganized by Proteolytic Cleavage During Virus Release," Journal of Virology, 63(6):2521-2526, 1989.

Wong et al., "Detection of Human Anti-*Flavivirus* Antibodies with a West Nile Virus Recombinant Antigen Microsphere Immunoassay," Journal of Clinical Microbiology, 42(1);65-72, 2004.

* cited by examiner

| NC 1-96 | C 97-465 | Pr 466-741 | M 742-966 | E 967-2469 | NS1 2470-3525 | NS2a 3526-4218 | NS2B 4219-4611 | NS3 4612-6468 | NS4a 6469-6915 | NS4b 6916-7680 | NS5 7681-10395 | NC 10396-11029 |

FIGURE 1

```
                Capsid→
                1                                            10
                M   S   K   K   P   G   G   P   G   K   S   R   A   V   N
                ATG TCT AAG AAA CCA GGA GGG CCC GGC AAG AGC CGG GCT GTC AAT 20                                           30
M   L   K   R   G   M   P   R   V   L   S   L   I   G   L   K   R   A   M   L
ATG CTA AAA CGC GGA ATG CCC CGC GTG TTG TCC TTG ATT GGA CTG AAG AGG GCT ATG TTG 40                                           50
S   L   I   D   G   K   G   P   I   R   F   V   L   A   L   L   A   F   F   R
AGC CTG ATC GAC GGC AAG GGG CCA ATA CGA TTT GTG TTG GCT CTC TTG GCG TTC TTC AGG 60                                           70
F   T   A   I   A   P   T   R   A   V   L   D   R   W   R   G   V   N   K   Q
TTC ACA GCA ATT GCT CCG ACC CGA GCA GTG CTG GAT CGA TGG AGA GGT GTG AAC AAA CAA 80                                           90
T   A   M   K   H   L   L   S   F   K   K   E   L   G   T   L   T   S   A   I
ACA GCG ATG AAA CAC CTT CTG AGT TTT AAG AAG GAA CTA GGG ACC TTG ACC AGT GCT ATC 100                                          110
N   R   R   S   S   K   Q   K   K   R   G   G   K   T   G   I   A   V   M   I
AAT CGG CGG AGC TCA AAA CAA AAG AAA AGA GGA GGA AAG ACC GGA ATT GCA GTC ATG ATT

| Pr→
                        120                                          130
G   L   I   A   S   V   G   A   V   T   L   S   N   F   Q   G   K   V   M   M
GGC CTG ATC GCC AGC GTA GGA GCA GTT ACC CTC TCT AAC TTC CAA GGG AAG GTG ATG ATG 140                                          150
T   V   N   A   T   D   V   T   D   V   I   T   I   P   T   A   A   G   K   N
ACG GTA AAT GCT ACT GAC GTC ACA GAT GTC ATC ACG ATT CCA ACA GCT GCT GGA AAG AAC 160                                          170
L   C   I   V   R   A   M   D   V   G   Y   M   C   D   D   T   I   T   Y   E
CTA TGC ATT GTC AGA GCA ATG GAT GTG GGA TAC ATG TGC GAT GAT ACT ATC ACT TAT GAA 180                                          190
C   P   V   L   S   A   G   N   D   P   E   D   I   D   C   W   C   T   K   S
TGC CCA GTG CTG TCG GCT GGT AAT GAT CCA GAA GAC ATC GAC TGT TGG TGC ACA AAG TCA

|
                        200                                          210
A   V   Y   V   R   Y   G   R   C   T   K   T   R   H   S   R   R   S   R   R
GCA GTC TAC GTC AGG TAT GGA AGA TGC ACC AAG ACA CGC CAC TCA AGA CGC AGT CGG AGG

M→
                        220                                          230
S   L   T   V   Q   T   H   G   E   S   T   L   A   N   K   K   G   A   W   M
TCA CTG ACA GTG CAG ACA CAC GGA GAA AGC ACT CTA GCG AAC AAG AAG GGG GCT TGG ATG
```

FIG. 2A

```
              240                              250
  D   S   T   K   A   T   R   Y   L   V   K   T   E   S   W   I   L   R   N   P
 GAC AGC ACC AAG GCC ACA AGG TAT TTG GTA AAA ACA GAA TCA TGG ATC TTG AGG AAC CCT 260                              270
  G   Y   A   L   V   A   A   V   I   G   W   M   L   G   S   N   T   M   Q   R
 GGA TAT GCC CTG GTG GCA GCC GTC ATT GGT TGG ATG CTT GGG AGC AAC ACC ATG CAG AGA
                                                        | E→
              280                              290
  V   V   F   V   V   L   L   L   V   A   P   A   Y   S   F   N   C   L   G
 GTT GTG TTT GTC GTG CTA TTG CTT TTG GTG GCC CCA GCT TAC AGC TTC AAC TGC CTT GGA 300                              310
  M   S   N   R   D   F   L   E   G   V   S   G   A   T   W   V   D   L   V   L
 ATG AGC AAC AGA GAC TTC TTG GAA GGA GTG TCT GGA GCA ACA TGG GTG GAT TTG GTT CTC 320                              330
  E   G   D   S   C   V   T   I   M   S   K   D   K   P   T   I   D   V   K   M
 GAA GGC GAC AGC TGC GTG ACT ATC ATG TCT AAG GAC AAG CCT ACC ATC GAT GTG AAG ATG 340                              350
  M   N   M   E   A   A   N   L   A   E   V   R   S   Y   C   Y   L   A   T   V
 ATG AAT ATG GAG GCG GCC AAC CTG GCA GAG GTC CGC AGT TAT TGC TAT TTG GCT ACC GTC 360                              370
  S   D   L   S   T   K   A   A   C   P   T   M   G   E   A   H   N   D   K   R
 AGC GAT CTC TCC ACC AAA GCT GCG TGC CCG ACC ATG GGA GAA GCT CAC AAT GAC AAA CGT 380                              390
  A   D   P   A   F   V   C   R   Q   G   V   V   D   R   G   W   G   N   G   C
 GCT GAC CCA GCT TTT GTG TGC AGA CAA GGA GTG GTG GAC AGG GGC TGG GGC AAC GGC TGC 400                              410
  G   L   F   G   K   G   S   I   D   T   C   A   K   F   A   C   S   T   K   A
 GGA CTA TTT GGC AAA GGA AGC ATT GAC ACA TGC GCC AAA TTT GCC TGC TCT ACC AAG GCA 420                              430
  I   G   R   T   I   L   K   E   N   I   K   Y   E   V   A   I   F   V   H   G
 ATA GGA AGA ACC ATC TTG AAA GAG AAT ATC AAG TAC GAA GTG GCC ATT TTT GTC CAT GGA 440                              450
  P   T   T   V   E   S   H   G   N   Y   S   T   Q   V   G   A   T   Q   A   G
 CCA ACT ACT GTG GAG TCG CAC GGA AAC TAC TCC ACA CAG GTT GGA GCC ACT CAG GCA GGG 460                              470
  R   F   S   I   T   P   A   A   P   S   Y   T   L   K   L   G   E   Y   G   E
 AGA TTC AGC ATC ACT CCT GCG GCG CCT TCA TAC ACA CTA AAG CTT GGA GAA TAT GGA GAG 480                              490
  V   T   V   D   C   E   P   R   S   G   I   D   T   N   A   Y   Y   V   M   T
 GTG ACA GTG GAC TGT GAA CCA CGG TCA GGG ATT GAC ACC AAT GCA TAC TAC GTG ATG ACT
```

FIG. 2B

```
      500                                          510
V   G   T   K   T   F   L   V   H   R   E   W   F   M   D   L   N   L   P   W
GTT GGA ACA AAG ACG TTC TTG GTC CAT CGT GAG TGG TTC ATG GAC CTC AAC CTC CCT TGG 520                                              530
S   S   A   G   S   T   V   W   R   N   R   E   T   L   M   E   F   E   E   P
AGC AGT GCT GGA AGT ACT GTG TGG AGG AAC AGA GAG ACG TTA ATG GAG TTT GAG GAA CCA 540                                              550
H   A   T   K   Q   S   V   I   A   L   G   S   Q   E   G   A   L   H   Q   A
CAC GCC ACG AAG CAG TCT GTG ATA GCA TTG GGC TCA CAA GAG GGA GCT CTG CAT CAA GCT 560                                              570
L   A   G   A   I   P   V   E   F   S   S   N   T   V   K   L   T   S   G   H
TTG GCT GGA GCC ATT CCT GTG AAA TTT TCA AGC AAC ACT GTC AAG TTG ACG TCG GGT CAT 580                                              590
L   K   C   R   V   K   M   E   K   L   Q   L   K   G   T   T   Y   G   V   C
TTG AAG TGT AGA GTG AAG ATG GAA AAA TTG CAG TTG AAG GGA ACA ACC TAT GGC GTC TGT 600                                              610
S   K   A   F   K   F   L   G   T   P   A   D   T   G   H   G   T   V   V   L
TCA AAG GCT TTC AAG TTT CTT GGG ACT CCC GCA GAC ACA GGT CAC GGC ACT GTG GTG TTG 620                                              630
E   L   Q   Y   T   G   T   D   G   P   C   K   V   P   I   S   S   V   A   S
GAA TTG CAG TAC ACT GGC ACG GAT GGA CCT TGC AAA GTT CCT ATC TCG TCA GTG GCT TCA 640                                              650
L   N   D   L   T   P   V   G   R   L   V   T   V   N   P   F   V   S   V   A
TTG AAC GAC CTA ACG CCA GTG GGC AGA TTG GTC ACT GTC AAC CCT TTT GTT TCA GTG GCC 660                                              670
T   A   N   A   K   V   L   I   E   L   E   P   P   F   G   D   S   Y   I   V
ACG GCC AAC GCT AAG GTC CTG ATT GAA TTG GAA CCA CCC TTT GGA GAC TCA TAC ATA GTG 680                                              690
V   G   R   G   E   Q   Q   I   N   H   H   W   H   K   S   G   S   S   I   G
GTG GGC AGA GGA GAA CAA CAG ATC AAT CAC CAT TGG CAC AAG TCT GGA AGC AGC ATT GGC 700                                              710
K   A   F   T   T   T   L   K   G   A   Q   R   L   A   A   L   G   D   T   A
AAA GCC TTT ACA ACC ACC CTC AAA GGA GCG CAG AGA CTA GCC GCT CTA GGA GAC ACA GCT 720                                              730
W   D   F   G   S   V   G   G   V   F   T   S   V   G   K   A   V   H   Q   V
TGG GAC TTT GGA TCA GTT GGA GGG GTG TTC ACC TCA GTT GGG AAG GCT GTC CAT CAA GTG 740                                              750
F   G   G   A   F   R   S   L   F   G   G   M   S   W   I   T   Q   G   L   L
TTC GGA GGA GCA TTC CGC TCA CTG TTC GGA GGC ATG TCC TGG ATA ACG CAA GGA TTG CTG
```

FIG. 2C

```
              760                                         770
    G    A    L    L    L    W    M    G    I    N    A    R    D    R    S    I    A    L    T    F
    GGG  GCT  CTC  CTG  TTG  TGG  ATG  GGC  ATC  AAT  GCT  CGT  GAT  AGG  TCC  ATA  GCT  CTC  ACG  TTT

| NS1→
              780                                         790
    L    A    V    G    G    V    L    L    F    L    S    V    N    V    H    A    D    T    G    C
    CTC  GCA  GTT  GGA  GGA  GTT  CTG  CTC  TTC  CTC  TCC  GTG  AAC  GTG  CAC  GCT  GAC  ACT  GGG  TGT 800                                         810
    A    I    D    I    S    R    Q    E    L    R    C    G    S    G    V    F    I    H    N    D
    GCC  ATA  GAC  ATC  AGC  CGG  CAA  GAG  CTG  AGA  TGT  GGA  AGT  GGA  GTG  TTC  ATA  CAC  AAT  GAT 820                                         830
    V    E    A    W    M    D    R    Y    K    Y    Y    P    E    T    P    Q    G    L    A    K
    GTG  GAG  GCT  TGG  ATG  GAC  CGG  TAC  AAG  TAT  TAC  CCT  GAA  ACG  CCA  CAA  GGC  CTA  GCC  AAG 840                                         850
    I    I    Q    K    A    H    K    E    G    V    C    G    L    R    S    V    S    R    L    E
    ATC  ATT  CAG  AAA  GCT  CAT  AAG  GAA  GGA  GTG  TGC  GGT  CTA  CGA  TCA  GTT  TCC  AGA  CTG  GAG 860                                         870
    H    Q    M    W    E    A    V    K    D    E    L    N    T    L    L    K    E    N    G    V
    CAT  CAA  ATG  TGG  GAA  GCA  GTG  AAG  GAC  GAG  CTG  AAC  ACT  CTT  TTG  AAG  GAG  AAT  GGT  GTG 880                                         890
    D    L    S    V    V    V    E    K    Q    E    G    M    Y    K    S    A    P    K    R    L
    GAC  CTT  AGT  GTC  GTG  GTT  GAG  AAA  CAG  GAG  GGA  ATG  TAC  AAG  TCA  GCA  CCT  AAA  CGC  CTC 900                                         910
    T    A    T    T    E    K    L    E    I    G    W    K    A    W    G    K    S    I    L    F
    ACC  GCC  ACC  ACG  GAA  AAA  TTG  GAA  ATT  GGC  TGG  AAG  GCC  TGG  GGA  AAG  AGT  ATT  TTA  TTT 920                                         930
    A    P    E    L    A    N    N    T    F    V    V    D    G    P    E    T    K    E    C    P
    GCA  CCA  GAA  CTC  GCC  AAC  AAC  ACC  TTT  GTG  GTT  GAT  GGT  CCG  GAG  ACC  AAG  GAA  TGT  CCG 940                                         950
    T    Q    N    R    A    W    N    S    L    E    V    E    D    F    G    F    G    L    T    S
    ACT  CAG  AAT  CGC  GCT  TGG  AAT  AGC  TTA  GAA  GTG  GAG  GAT  TTT  GGA  TTT  GGT  CTC  ACC  AGC 960                                         970
    T    R    M    F    L    K    V    R    E    S    N    T    T    E    C    D    S    K    I    I
    ACT  CGG  ATG  TTC  CTG  AAG  GTC  AGA  GAG  AGC  AAC  ACA  ACT  GAA  TGT  GAC  TCG  AAG  ATC  ATT 980                                         990
    G    T    A    V    K    N    N    L    A    I    H    S    D    L    S    Y    W    I    E    S
    GGA  ACG  GCT  GTC  AAG  AAC  AAC  TTG  GCG  ATC  CAC  AGT  GAC  CTG  TCC  TAT  TGG  ATT  GAA  AGC 1000                                        1010
    R    L    N    D    T    W    K    L    E    R    A    V    L    G    E    V    K    S    C    T
    AGG  CTC  AAT  GAT  ACG  TGG  AAG  CTT  GAA  AGG  GCA  GTT  CTG  GGT  GAA  GTC  AAA  TCA  TGT  ACG
```

FIG. 2D

```
                    1020                                              1030
    W   P   E   T   H   T   L   W   G   D   G   I   L   E   S   D   L   I   I   P
    TGG CCT GAG ACG CAT ACC TTG TGG GGC GAT GGA ATC CTT GAG AGT GAC TTG ATA ATA CCA 1040                                          1050
    V   T   L   A   G   P   R   S   N   H   N   R   R   P   G   Y   K   T   Q   N
    GTC ACA CTG GCG GGA CCA CGA AGC AAT CAC AAT CGG AGA CCT GGG TAC AAG ACA CAA AAC 1060                                          1070
    Q   G   P   W   D   E   G   R   V   E   I   D   F   D   Y   C   P   G   T   T
    CAG GGC CCA TGG GAC GAA GGC CGG GTA GAG ATT GAC TTC GAT TAC TGC CCA GGA ACT ACG 1080                                          1090
    V   T   L   S   E   S   C   G   H   R   G   P   A   T   R   T   T   T   E   S
    GTC ACC CTG AGT GAG AGC TGC GGA CAC CGT GGA CCT GCC ACT CGC ACC ACC ACA GAG AGC 1100                                          1110
    G   K   L   I   T   D   W   C   C   R   S   C   T   L   P   P   L   R   Y   Q
    GGA AAG TTG ATA ACA GAT TGG TGC TGC AGG AGC TGC ACC TTA CCA CCA CTG CGC TAC CAA 1120                                          1130
    T   D   S   G   C   W   Y   G   M   E   I   R   P   Q   R   H   D   E   K   T
    ACT GAC AGC GGC TGT TGG TAT GGT ATG GAG ATC AGA CCA CAG AGA CAT GAT GAA AAG ACC

| NS2a→
                            1140                                          1150
    L   V   Q   S   Q   V   N   A   Y   N   A   D   M   I   D   P   F   Q   L   G
    CTC GTG CAG TCA CAA GTG AAT GCT TAT AAT GCT GAT ATG ATT GAC CCT TTT CAG TTG GGC 1160                                          1170
    L   L   V   V   F   L   A   T   Q   E   V   L   R   K   R   W   T   A   K   I
    CTT CTG GTC GTG TTC TTG GCC ACC CAG GAG GTC CTT CGC AAG AGG TGG ACA GCC AAG ATC 1180                                          1190
    S   M   P   A   I   L   I   A   L   L   V   L   V   F   G   G   I   T   Y   T
    AGC ATG CCA GCT ATA CTG ATT GCT CTG CTA GTC CTG GTG TTT GGG GGC ATT ACT TAC ACT 1200                                          1210
    D   V   L   R   Y   V   I   L   V   G   A   A   F   A   E   S   N   S   G   G
    GAT GTG TTA CGC TAT GTC ATC TTG GTG GGG GCA GCT TTC GCA GAA TCT AAT TCG GGA GGA 1220                                          1230
    D   V   V   H   L   A   L   M   A   T   F   K   I   Q   P   V   F   M   V   A
    GAC GTG GTA CAC TTG GCG CTC ATG GCG ACC TTC AAG ATA CAA CCA GTG TTT ATG GTG GCA 1240                                          1250
    S   F   L   K   A   R   W   T   N   Q   E   N   I   L   L   M   L   A   A   V
    TCG TTT CTC AAA GCG AGA TGG ACC AAC CAG GAG AAC ATT TTG TTG ATG TTG GCG GCT GTT 1260                                          1270
    F   F   Q   M   A   Y   H   D   A   R   Q   I   L   L   W   E   I   P   D   V
    TTC TTT CAA ATG GCT TAT CAC GAT GCC CGC CAA ATT CTG CTC TGG GAG ATC CCT GAT GTG
```

FIG. 2E

```
             1280                                              1290
 L   N   S   L   A   V   A   W   M   I   L   R   A   I   T   F   T   T   T   S
TTG AAT TCA CTG GCG GTA GCT TGG ATG ATA CTG AGA GCC ATA ACA TTC ACA ACG ACA TCA 1300                                              1310
 N   V   V   V   P   L   L   A   L   L   T   P   G   L   R   C   L   N   L   D
AAC GTG GTT GTT CCG CTG CTA GCC CTG CTA ACA CCC GGG CTG AGA TGC TTG AAT CTG GAT 1320                                              1330
 V   Y   R   I   L   L   L   M   V   G   I   G   S   L   I   R   E   K   R   S
GTC TAC AGG ATA CTG CTG TTG ATG GTC GGA ATA GGC AGC TTG ATC AGG GAG AAG AGG AGT 1340                                              1350
 A   A   A   K   K   K   G   A   S   L   L   C   L   A   L   A   S   T   G   L
GCA GCT GCA AAA AAG AAA GGA GCA AGT CTG CTA TGC TTG GCT CTA GCC TCA ACA GGA CTT

| NS2b→
             1360                                              1370
 F   N   P   M   I   L   A   A   G   L   I   A   C   D   P   N   R   K   R   G
TTC AAC CCC ATG ATC CTT GCT GCT GGA CTG ATT GCA TGT GAT CCC AAC CGT AAA CGC GGA 1380                                              1390
 W   P   A   T   E   V   M   T   A   V   G   L   M   F   A   I   V   G   G   L
TGG CCC GCA ACT GAA GTG ATG ACA GCT GTC GGC CTA ATG TTT GCC ATC GTC GGA GGG CTG 1400                                              1410
 A   E   L   D   I   D   S   M   A   I   P   M   T   I   A   G   L   M   F   A
GCA GAG CTT GAC ATT GAC TCC ATG GCC ATT CCA ATG ACT ATC GCG GGG CTC ATG TTT GCT 1420                                              1430
 A   F   V   I   S   G   K   S   T   D   M   W   I   E   R   T   A   D   I   S
GCT TTC GTG ATT TCT GGG AAA TCA ACA GAT ATG TGG ATT GAG AGA ACG GCG GAC ATT TCC 1440                                              1450
 W   E   S   D   A   E   I   T   G   S   S   E   R   V   D   V   R   L   D   D
TGG GAA AGT GAT GCA GAA ATT ACA GGC TCG AGC GAA AGA GTT GAT GTG CGG CTT GAT GAT 1460                                              1470
 D   G   N   F   Q   L   M   N   D   P   G   A   P   W   K   I   W   M   L   R
GAT GGA AAC TTC CAG CTC ATG AAT GAT CCA GGA GCA CCT TGG AAG ATA TGG ATG CTC AGA 1480                                              1490
 M   V   C   L   A   I   S   A   Y   T   P   W   A   I   L   P   S   V   V   G
ATG GTC TGT CTC GCG ATT AGT GCG TAC ACC CCC TGG GCA ATC TTG CCC TCA GTA GTT GGA

| NS3→
             1500                                              1510
 F   W   I   T   L   Q   Y   T   K   R   G   G   V   L   W   D   T   P   S   P
TTT TGG ATA ACT CTC CAA TAC ACA AAG AGA GGA GGC GTG TTG TGG GAC ACT CCC TCA CCA 1520                                              1530
 K   E   Y   K   K   G   D   T   T   T   G   V   Y   R   I   M   T   R   G   L
AAG GAG TAC AAA AAG GGG GAC ACG ACC ACC GGC GTC TAC AGG ATC ATG ACT CGT GGG CTG
```

FIG. 2F

```
           1540                                         1550
 L   G   S   Y   Q   A   G   A   G   V   M   V   E   G   V   F   H   T   L   W
CTC GGC AGT TAT CAA GCA GGA GCG GGC GTG ATG GTT GAA GGT GTT TTC CAC ACC CTT TGG 1560                                         1570
 H   T   T   K   G   A   A   L   M   S   G   E   G   R   L   D   P   Y   W   G
CAT ACA ACA AAA GGA GCC GCT TTG ATG AGC GGA GAG GGC CGC CTG GAC CCA TAC TGG GGC 1580                                         1590
 S   V   K   E   D   R   L   C   Y   G   G   P   W   K   L   Q   H   K   W   N
AGT GTC AAG GAG GAT CGA CTT TGT TAC GGA GGA CCC TGG AAA TTG CAG CAC AAG TGG AAC 1600                                         1610
 G   Q   D   E   V   Q   M   I   V   V   E   P   G   K   N   V   K   N   V   Q
GGG CAG GAT GAG GTG CAG ATG ATT GTG GTG GAA CCT GGC AAG AAC GTT AAG AAC GTC CAG 1620                                         1630
 T   K   P   G   V   F   K   T   P   E   G   E   I   G   A   V   T   L   D   F
ACG AAA CCA GGG GTG TTC AAA ACA CCT GAA GGA GAA ATC GGG GCC GTG ACT TTG GAC TTC 1640                                         1650
 P   T   G   T   S   G   S   P   I   V   D   K   N   G   D   V   I   G   L   Y
CCC ACT GGA ACA TCA GGC TCA CCA ATA GTG GAC AAA AAC GGT GAT GTG ATT GGG CTT TAT 1660                                         1670
 G   N   G   V   I   M   P   N   G   S   Y   I   S   A   I   V   Q   G   E   R
GGC AAT GGA GTC ATA ATG CCC AAC GGC TCA TAC ATA AGC GCG ATA GTG CAG GGT GAA AGG 1680                                         1690
 M   D   E   P   I   P   A   G   F   E   P   E   M   L   R   K   K   Q   I   T
ATG GAT GAG CCA ATC CCA GCC GGA TTC GAA CCT GAG ATG CTG AGG AAA AAA CAG ATC ACT 1700                                         1710
 V   L   D   L   H   P   G   A   G   K   T   R   R   I   L   P   Q   I   I   K
GTA CTG GAT CTC CAT CCC GGC GCC GGT AAA ACA AGG AGG ATT CTG CCA CAG ATC ATC AAA 1720                                         1730
 E   A   I   N   R   R   L   R   T   A   V   L   A   P   T   R   V   V   A   A
GAG GCC ATA AAC AGA AGA CTG AGA ACA GCC GTG CTA GCA CCA ACC AGG GTT GTG GCT GCT 1740                                         1750
 E   M   A   E   A   L   R   G   L   P   I   R   Y   Q   T   S   A   V   P   R
GAG ATG GCT GAA GCA CTG AGA GGA CTG CCC ATC CGG TAC CAG ACA TCC GCA GTG CCC AGA 1760                                         1770
 E   H   N   G   N   E   I   V   D   V   M   C   H   A   T   L   T   H   R   L
GAA CAT AAT GGA AAT GAG ATT GTT GAT GTC ATG TGT CAT GCT ACC CTC ACC CAC AGG CTG 1780                                         1790
 M   S   P   H   R   V   P   N   Y   N   L   F   V   M   D   E   A   H   F   T
ATG TCT CCT CAC AGG GTG CCG AAC TAC AAC CTG TTC GTG ATG GAT GAG GCT CAT TTC ACC
```

FIG. 2G

```
        1800                                    1810
D   P   A   S   I   A   A   R   G   Y   I   S   T   K   V   E   L   G   E   A
GAC CCA GCT AGC ATT GCA GCA AGA GGT TAC ATT TCC ACA AAG GTC GAG CTA GGG GAG GCG 1820                                    1830
A   A   I   F   M   T   A   T   P   P   G   T   S   D   P   F   P   E   S   N
GCG GCA ATA TTC ATG ACA GCC ACC CCA CCA GGC ACT TCA GAT CCA TTC CCA GAG TCC AAT 1840                                    1850
S   P   I   S   D   L   Q   T   E   I   P   D   R   A   W   N   S   G   Y   E
TCA CCA ATT TCC GAC TTA CAG ACT GAG ATC CCG GAT CGA GCT TGG AAC TCT GGA TAC GAA 1860                                    1870
W   I   T   E   Y   T   G   K   T   V   W   F   V   P   S   V   K   M   G   N
TGG ATC ACA GAA TAC ACC GGG AAG ACG GTT TGG TTT GTG CCT AGT GTC AAG ATG GGG AAT 1880                                    1890
E   I   A   L   C   L   Q   R   A   G   K   K   V   V   Q   L   N   R   K   S
GAG ATT GCC CTT TGC CTA CAA CGT GCT GGA AAG AAA GTA GTC CAA TTG AAC AGA AAG TCG 1900                                    1910
Y   E   T   E   Y   P   K   C   K   N   D   D   W   D   F   V   I   T   T   D
TAC GAG ACG GAG TAC CCA AAA TGT AAG AAC GAT GAT TGG GAC TTT GTT ATC ACA ACA GAC 1920                                    1930
I   S   E   M   G   A   N   F   K   A   S   R   V   I   D   S   R   K   S   V
ATA TCT GAA ATG GGG GCT AAC TTC AAG GCG AGC AGG GTG ATT GAC AGC CGG AAG AGT GTG 1940                                    1950
K   P   T   I   I   T   E   G   E   G   R   V   I   L   G   E   P   S   A   V
AAA CCA ACC ATC ATA ACA GAA GGA GAA GGG AGA GTG ATC CTG GGA GAA CCA TCT GCA GTG 1960                                    1970
T   A   A   S   A   A   Q   R   R   G   R   I   G   R   N   P   S   Q   V   G
ACA GCA GCT AGT GCC GCC CAG AGA CGT GGA CGT ATC GGT AGA AAT CCG TCG CAA GTT GGT 1980                                    1990
D   E   Y   C   Y   G   G   H   T   N   E   D   D   S   N   F   A   H   W   T
GAT GAG TAC TGT TAT GGG GGG CAC ACG AAT GAA GAC GAC TCG AAC TTC GCC CAT TGG ACT 2000                                    2010
E   A   R   I   M   L   D   N   I   N   M   P   N   G   L   I   A   Q   F   Y
GAG GCA CGA ATC ATG CTG GAC AAC ATC AAC ATG CCA AAC GGA CTG ATC GCT CAA TTC TAC 2020                                    2030
Q   P   E   R   E   K   V   Y   T   M   D   G   E   Y   R   L   R   G   E   E
CAA CCA GAG CGT GAG AAG GTA TAT ACC ATG GAT GGG GAA TAC CGG CTC AGA GGA GAA GAG 2040                                    2050
R   K   N   F   L   E   L   L   R   T   A   D   L   P   V   W   L   A   Y   K
AGA AAA AAC TTT CTG GAA CTG TTG AGG ACT GCA GAT CTG CCA GTT TGG CTG GCT TAC AAG
```

FIG. 2H

```
                    2060                                                2070
     V    A    A    A    G    V    S    Y    H    D    R    R    W    C    F    D    G    P    R    T
    GTT  GCA  GCG  GCT  GGA  GTG  TCA  TAC  CAC  GAC  CGG  AGG  TGG  TGC  TTT  GAT  GGT  CCT  AGG  ACA
                    2080                                                2090
     N    T    I    L    E    D    N    N    E    V    E    V    I    T    K    L    G    E    R    K
    AAC  ACA  ATT  TTA  GAA  GAC  AAC  AAC  GAA  GTG  GAA  GTC  ATC  ACG  AAG  CTT  GGT  GAA  AGG  AAG
                    2100                                                2110
     I    L    R    P    R    W    I    D    A    R    V    Y    S    D    H    Q    A    L    K    A
    ATT  CTG  AGG  CCG  CGC  TGG  ATT  GAC  GCC  AGG  GTG  TAC  TCG  GAT  CAC  CAG  GCA  CTA  AAG  GCG
                                          | NS4a→
                    2120                                                2130
     F    K    D    F    A    S    G    K    R    S    Q    I    G    L    I    E    V    L    G    K
    TTC  AAG  GAC  TTC  GCC  TCG  GGA  AAA  CGT  TCT  CAG  ATA  GGG  CTC  ATT  GAG  GTT  CTG  GGA  AAG
                    2140                                                2150
     M    P    E    H    F    M    G    K    T    W    E    A    L    D    T    M    Y    V    V    A
    ATG  CCT  GAG  CAC  TTC  ATG  GGG  AAG  ACA  TGG  GAA  GCA  CTT  GAC  ACC  ATG  TAC  GTT  GTG  GCC
                    2160                                                2170
     T    A    E    K    G    G    R    A    H    R    M    A    L    E    E    L    P    D    A    L
    ACT  GCA  GAG  AAA  GGA  GGA  AGA  GCT  CAC  AGA  ATG  GCC  CTG  GAG  GAA  CTG  CCA  GAT  GCT  CTT
                    2180                                                2190
     Q    T    I    A    L    I    A    L    L    S    V    M    T    M    G    V    F    F    L    L
    CAG  ACA  ATT  GCC  TTG  ATT  GCC  TTA  TTG  AGT  GTG  ATG  ACC  ATG  GGA  GTA  TTC  TTC  CTC  CTC
                    2200                                                2210
     M    Q    R    K    G    I    G    K    I    G    L    G    G    A    V    L    G    V    A    T
    ATG  CAG  CGG  AAG  GGC  ATT  GGA  AAG  ATA  GGT  TTG  GGA  GGC  GCT  GTC  TTG  GGA  GTC  GCG  ACC
                    2220                                                2230
     F    F    C    W    M    A    E    V    P    G    T    K    I    A    G    M    L    L    L    S
    TTT  TTC  TGT  TGG  ATG  GCT  GAA  GTT  CCA  GGA  ACG  AAG  ATC  GCC  GGA  ATG  TTG  CTG  CTC  TCC
                    2240                                                2250
     L    L    L    M    I    V    L    I    P    E    P    E    K    Q    R    S    Q    T    D    N
    CTT  CTC  TTG  ATG  ATT  GTG  CTA  ATT  CCT  GAG  CCA  GAG  AAG  CAA  CGT  TCG  CAG  ACA  GAC  AAC
                                                                              | NS4b→
                    2260                                                2270
     Q    L    A    V    F    L    I    C    V    M    T    L    V    S    A    V    A    A    N    E
    CAG  CTA  GCC  GTG  TTC  CTG  ATT  TGT  GTC  ATG  ACC  CTT  GTG  AGC  GCA  GTG  GCA  GCC  AAC  GAG
                    2280                                                2290
     M    G    W    L    D    K    T    K    S    D    I    S    S    L    F    G    Q    R    I    E
    ATG  GGT  TGG  CTA  GAT  AAG  ACC  AAG  AGT  GAC  ATA  AGC  AGT  TTG  TTT  GGG  CAA  AGA  ATT  GAG
                    2300                                                2310
     V    K    E    N    F    S    M    G    E    F    L    L    D    L    R    P    A    T    A    W
    GTC  AAG  GAG  AAT  TTC  AGC  ATG  GGA  GAG  TTT  CTT  TTG  GAC  TTG  AGG  CCG  GCA  ACA  GCC  TGG
```

FIG. 2I

```
                2320                              2330
  S   L   Y   A   V   T   T   A   V   L   T   P   L   L   K   H   L   I   T   S
TCA CTG TAC GCT GTG ACA ACA GCG GTC CTC ACT CCA CTG CTA AAG CAT TTG ATC ACG TCA 2340                              2350
  D   Y   I   N   T   S   L   T   S   I   N   V   Q   A   S   A   L   F   T   L
GAT TAC ATC AAC ACC TCA TTG ACC TCA ATA AAC GTT CAG GCA AGT GCA CTA TTC ACA CTC 2360                              2370
  A   R   G   F   P   F   V   D   V   G   V   S   A   L   L   L   A   A   G   C
GCG CGA GGC TTC CCC TTC GTC GAT GTT GGA GTG TCG GCT CTC CTG CTA GCA GCC GGA TGC 2380                              2390
  W   G   Q   V   T   L   T   V   T   V   T   A   A   T   L   L   F   C   H   Y
TGG GGA CAA GTC ACC CTC ACC GTT ACG GTA ACA GCG GCA ACA CTC CTT TTT TGC CAC TAT 2400                              2410
  A   Y   M   V   P   G   W   Q   A   E   A   M   R   S   A   Q   R   R   T   A
GCC TAC ATG GTT CCC GGT TGG CAA GCT GAG GCA ATG CGC TCA GCC CAG CGG CGG ACA GCG 2420                              2430
  A   G   I   M   K   N   A   V   V   D   G   I   V   A   T   D   V   P   E   L
GCC GGA ATC ATG AAG AAC GCT GTA GTG GAT GGC ATC GTG GCC ACG GAC GTC CCA GAA TTA 2440                              2450
  E   R   T   T   P   I   M   Q   K   K   V   G   Q   I   M   L   I   L   V   S
GAG CGC ACC ACA CCC ATC ATG CAG AAG AAA GTT GGA CAG ATC ATG CTG ATC TTG GTG TCT 2460                              2470
  L   A   A   V   V   V   N   P   S   V   K   T   V   R   E   A   G   I   L   I
CTA GCT GCA GTA GTA GTG AAC CCG TCT GTG AAG ACA GTA CGA GAA GCC GGA ATT TTG ATC 2480                              2490
  T   A   A   A   V   T   L   W   E   N   G   A   S   S   V   W   N   A   T   T
ACG GCC GCA GCG GTG ACG CTT TGG GAG AAT GGA GCA AGC TCT GTT TGG AAC GCA ACA ACT 2500                              2510
  A   I   G   L   C   H   I   M   R   G   G   W   L   S   C   L   S   I   T   W
GCC ATC GGA CTC TGC CAC ATC ATG CGT GGG GGT TGG TTG TCA TGT CTA TCC ATA ACA TGG

| NS5→
                2520                              2530
  T   L   I   K   N   M   E   K   P   G   L   K   R   G   G   A   K   G   R   T
ACA CTC ATA AAG AAC ATG GAA AAA CCA GGA CTA AAA AGA GGT GGG GCA AAA GGA CGC ACC 2540                              2550
  L   G   E   V   W   K   E   R   L   N   Q   M   T   K   E   E   F   T   R   Y
TTG GGA GAG GTT TGG AAA GAA AGA CTC AAC CAG ATG ACA AAA GAA GAG TTC ACT AGG TAC 2560                              2570
  R   K   E   A   I   I   E   V   D   R   S   A   A   K   H   A   R   K   E   G
CGC AAA GAG GCC ATC ATC GAA GTC GAT CGC TCA GCG GCA AAA CAC GCC AGG AAA GAA GGC
```

FIG. 2J

```
                      2580                                                  2590
      N   V   T   G   G   H   P   V   S   R   G   T   A   K   L   R   W   L   V   E
     AAT GTC ACT GGA GGG CAT CCA GTC TCT AGG GGC ACA GCA AAA CTG AGA TGG CTG GTC GAA 2600                                                  2610
      R   R   F   L   E   P   V   G   K   V   I   D   L   G   C   G   R   G   G   W
     CGG AGG TTT CTC GAA CCG GTC GGA AAA GTG ATT GAC CTT GGA TGT GGA AGA GGC GGT TGG 2620                                                  2630
      C   Y   Y   M   A   T   Q   K   R   V   Q   E   V   R   G   Y   T   K   G   G
     TGT TAC TAT ATG GCA ACC CAA AAA AGA GTC CAA GAA GTC AGA GGG TAC ACA AAG GGC GGT 2640                                                  2650
      P   G   H   E   E   P   Q   L   V   Q   S   Y   G   W   N   I   V   T   M   K
     CCC GGA CAT GAA GAG CCC CAA CTA GTG CAA AGT TAT GGA TGG AAC ATT GTC ACC ATG AAG 2660                                                  2670
      S   G   V   D   V   F   Y   R   P   S   E   C   C   D   T   L   L   C   D   I
     AGT GGA GTG GAT GTG TTC TAC AGA CCT TCT GAG TGT TGT GAC ACC CTC CTT TGT GAC ATC 2680                                                  2690
      G   E   S   S   S   S   A   E   V   E   E   H   R   T   I   R   V   L   E   M
     GGA GAG TCC TCG TCA AGT GCT GAG GTT GAA GAG CAT AGG ACG ATT CGG GTC CTT GAA ATG 2700                                                  2710
      V   E   D   W   L   H   R   G   P   R   E   F   C   V   K   V   L   C   P   Y
     GTT GAG GAC TGG CTG CAC CGA GGG CCA AGG GAA TTT TGC GTG AAG GTG CTC TGC CCC TAC 2720                                                  2730
      M   P   K   V   I   E   K   M   E   L   L   Q   R   R   Y   G   G   G   L   V
     ATG CCG AAA GTC ATA GAG AAG ATG GAG CTG CTC CAA CGC CGG TAT GGG GGG GGA CTG GTC 2740                                                  2750
      R   N   P   L   S   R   N   S   T   H   E   M   Y   W   V   S   R   A   S   G
     AGA AAC CCA CTC TCA CGG AAT TCC ACG CAC GAG ATG TAT TGG GTG AGT CGA GCT TCA GGC 2760                                                  2770
      N   V   V   H   S   V   N   M   T   S   Q   V   L   L   G   R   M   E   K   R
     AAT GTG GTA CAT TCA GTG AAT ATG ACC AGC CAG GTG CTC CTA GGA AGA ATG GAA AAA AGG 2780                                                  2790
      T   W   K   G   P   Q   Y   E   E   D   V   N   L   G   S   G   T   R   A   V
     ACC TGG AAG GGA CCC CAA TAC GAG GAA GAT GTA AAC TTG GGA AGT GGA ACC AGG GCG GTG 2800                                                  2810
      G   K   P   L   L   N   S   D   T   S   K   I   K   N   R   I   E   R   L   R
     GGA AAA CCC CTG CTC AAC TCA GAC ACC AGT AAA ATC AAG AAC AGG ATT GAA CGA CTC AGG 2820                                                  2830
      R   E   Y   S   S   T   W   H   H   D   E   N   H   P   Y   R   T   W   N   Y
     CGT GAG TAC AGT TCG ACG TGG CAC CAC GAT GAG AAC CAC CCA TAT AGA ACC TGG AAC TAT
```

FIG. 2K

```
                2840                                              2850
     H   G   S   Y   D   V   K   P   T   G   S   A   S   S   L   V   N   G   V   V
    CAC GGC AGT TAT GAT GTG AAG CCC ACA GGC TCC GCC AGT TCG CTG GTC AAT GGA GTG GTC 2860                                              2870
     R   L   L   S   K   P   W   D   T   I   T   N   V   T   T   M   A   M   T   D
    AGG CTC CTC TCA AAA CCA TGG GAC ACC ATC ACG AAT GTT ACC ACC ATG GCC ATG ACT GAC 2880                                              2890
     T   T   P   F   G   Q   Q   R   V   F   K   E   K   V   D   T   K   A   P   E
    ACT ACT CCC TTC GGG CAG CAG CGA GTG TTC AAA GAG AAG GTG GAC ACG AAA GCT CCT GAA 2900                                              2910
     P   P   E   G   V   K   Y   V   L   N   E   T   T   N   W   L   W   A   F   L
    CCG CCA GAA GGA GTG AAG TAC GTG CTC AAT GAG ACC ACC AAC TGG TTG TGG GCG TTT TTG 2920                                              2930
     A   R   E   K   R   P   R   M   C   S   R   E   E   F   I   R   K   V   N   S
    GCC AGA GAA AAA CGT CCC AGA ATG TGC TCT CGA GAG GAA TTC ATA AGA AAG GTC AAC AGC 2940                                              2950
     N   A   A   L   G   A   M   F   E   E   Q   N   Q   W   R   S   A   R   E   A
    AAT GCA GCT TTG GGT GCC ATG TTT GAA GAG CAG AAT CAA TGG AGG AGC GCC AGA GAA GCA 2960                                              2970
     V   E   D   P   K   F   W   E   M   V   D   E   E   R   E   A   H   L   R   G
    GTT GAA GAT CCA AAA TTT TGG GAG ATG GTG GAT GAG GAG CGC GAG GCA CAT CTG CGG GGG 2980                                              2990
     E   C   H   T   C   I   Y   N   M   M   G   K   R   E   K   K   P   G   E   F
    GAA TGT CAC ACT TGC ATT TAC AAC ATG ATG GGA AAG AGA GAG AAA AAA CCC GGA GAG TTC 3000                                              3010
     G   K   A   K   G   S   R   A   I   W   F   M   W   L   G   A   R   F   L   E
    GGA AAG GCC AAG GGA AGC AGA GCC ATT TGG TTC ATG TGG CTC GGA GCT CGC TTT CTG GAG 3020                                              3030
     F   E   A   L   G   F   L   N   E   D   H   W   L   G   R   K   N   S   G   G
    TTC GAG GCT CTG GGT TTT CTC AAT GAA GAC CAC TGG CTT GGA AGA AAG AAC TCA GGA GGA 3040                                              3050
     G   V   E   G   L   G   L   Q   K   L   G   Y   I   L   R   E   V   G   T   R
    GGT GTC GAG GGC TTG GGC CTC CAA AAA CTG GGT TAC ATC CTG CGT GAA GTT GGC ACC CGG 3060                                              3070
     P   G   G   K   I   Y   A   D   D   T   A   G   W   D   T   R   I   T   R   A
    CCT GGG GGC AAG ATC TAT GCT GAT GAC ACA GCT GGC TGG GAC ACC CGC ATC ACG AGA GCT 3080                                              3090
     D   L   E   N   E   A   K   V   L   E   L   L   D   G   E   H   R   R   L   A
    GAC TTG GAA AAT GAA GCT AAG GTG CTT GAG CTG CTT GAT GGG GAA CAT CGG CGT CTT GCC

FIG. 2L
```

```
            3100                                         3110
 R   A   I   I   E   L   T   Y   R   H   K   V   V   K   V   M   R   P   A   A
AGG GCC ATC ATT GAG CTC ACC TAT CGT CAC AAA GTT GTG AAA GTG ATG CGC CCG GCT GCT 3120                                         3130
 D   G   R   T   V   M   D   V   I   S   R   E   D   Q   R   G   S   G   Q   V
GAT GGA AGA ACC GTC ATG GAT GTT ATC TCC AGA GAA GAT CAG AGG GGG AGT GGA CAA GTT 3140                                         3150
 V   T   Y   A   L   N   T   F   T   N   L   A   V   Q   L   V   R   M   M   E
GTC ACC TAC GCC CTA AAC ACT TTC ACC AAC CTG GCC GTC CAG CTG GTG AGG ATG ATG GAA 3160                                         3170
 G   E   G   V   I   G   P   D   D   V   E   K   L   T   K   G   K   G   P   K
GGG GAA GGA GTG ATT GGC CCA GAT GAT GTG GAG AAA CTC ACA AAA GGG AAA GGA CCC AAA 3180                                         3190
 V   R   T   W   L   F   E   N   G   E   E   R   L   S   R   M   A   V   S   G
GTC AGG ACC TGG CTG TTT GAG AAT GGG GAA GAA AGA CTC AGC CGC ATG GCT GTC AGT GGA 3200                                         3210
 D   D   C   V   V   K   P   L   D   D   R   F   A   T   S   L   H   F   L   N
GAT GAC TGT GTG GTA AAG CCC CTG GAC GAT CGC TTT GCC ACC TCG CTC CAC TTC CTC AAT 3220                                         3230
 A   M   S   K   V   R   K   D   I   Q   E   W   K   P   S   T   G   W   Y   D
GCT ATG TCA AAG GTT CGC AAA GAC ATC CAA GAG TGG AAA CCG TCA ACT GGA TGG TAT GAT 3240                                         3250
 W   Q   Q   V   P   F   C   S   N   H   F   T   E   L   I   M   K   D   G   R
TGG CAG CAG GTT CCA TTT TGC TCA AAC CAT TTC ACT GAA TTG ATC ATG AAA GAT GGA AGA 3260                                         3270
 T   L   V   V   P   C   R   G   Q   D   E   L   V   G   R   A   R   I   S   P
ACA CTG GTG GTT CCA TGC CGA GGA CAG GAT GAA TTG GTA GGC AGA GCT CGC ATA TCT CCA 3280                                         3290
 G   A   G   W   N   V   R   D   T   A   C   L   A   K   S   Y   A   Q   M   W
GGG GCC GGA TGG AAC GTC CGC GAC ACT GCT TGT CTG GCT AAG TCT TAT GCC CAG ATG TGG 3300                                         3310
 L   L   L   Y   F   H   R   R   D   L   R   L   M   A   N   A   I   C   S   A
CTG CTT CTG TAC TTC CAC AGA AGA GAC CTG CGG CTC ATG GCC AAC GCC ATT TGC TCC GCT 3320                                         3330
 V   P   V   N   W   V   P   T   G   R   T   T   W   S   I   H   A   G   G   E
GTC CCT GTG AAT TGG GTC CCT ACC GGA AGA ACC ACG TGG TCC ATC CAT GCA GGA GGA GAG 3340                                         3350
 W   M   T   T   E   D   M   L   E   V   W   N   R   V   W   I   E   E   N   E
TGG ATG ACA ACA GAG GAC ATG TTG GAG GTC TGG AAC CGT GTT TGG ATA GAG GAG AAT GAA
```

FIG. 2M

```
                      3360                                                    3370
     W    M    E    D    K    T    P    V    E    K    W    S    D    V    P    Y    S    G    K    R
    TGG  ATG  GAA  GAC  AAA  ACC  CCA  GTG  GAG  AAA  TGG  AGT  GAC  GTC  CCA  TAT  TCA  GGA  AAA  CGA 3380                                                    3390
     E    D    I    W    C    G    S    L    I    G    T    R    A    R    A    T    W    A    E    N
    GAG  GAC  ATC  TGG  TGT  GGC  AGC  CTG  ATT  GGC  ACA  AGA  GCC  CGA  GCC  ACG  TGG  GCA  GAA  AAC 3400                                                    3410
     I    Q    V    A    I    N    Q    V    R    A    I    I    G    D    E    K    Y    V    D    Y
    ATC  CAG  GTG  GCT  ATC  AAC  CAA  GTC  AGA  GCA  ATC  ATC  GGA  GAT  GAG  AAG  TAT  GTG  GAT  TAC 3420                                          3430           3433
     M    S    S    L    K    R    Y    E    D    T    T    L    V    E    D    T    V    L
    ATG  AGT  TCA  CTA  AAG  AGA  TAT  GAA  GAC  ACA  ACT  TTG  GTT  GAG  GAC  ACA  GTA  CTG
```

FIG. 2N

```
                             prM------->
     360  gtaggagca [GTTACCCTCTCTAACTTCCAAGGGAAGGTGATGATGACGGTAAATGCTA
       0  .........  [GTTACCCTCTCTAACTTCCAAGGGAAGGTGATGATGACGGTAAATGCTA 418  CTGACGTCACAGATGTCATCACGATTCCAACAGCTGCTGGAAAGAACCTATGCATTGTCA
      50  CTGACGTCACAGATGTCATCACGATTCCAACAGCTGCTGGAAAGAACCTATGCATTGTCA 478  GAGCAATGGATGTGGGATACATGTGCGATGATACTATCACTTATGAATGCCCAGTGCTGT
     110  GAGCAATGGATGTGGGATACATGTGCGATGATACTATCACTTATGAATGCCCAGTGCTGT PstI created
                                                          **********
     538  CGGCTGGTAATGATCCAGAAGACATCGACTGTTGGTGCACAAAGTC] a [GCAGTCTAC
     170  CGGCTGGTAATGATCCAGAAGACATCGACTGTTGGTGCACAAAGTC] t [GCAGTCTAC MluI created
                           ********
     594  GTCAGGTATGGAAGATGCACCAAGAC] acgc [CACTCAAGACGCAGTCGGAGGTCACT
     226  GTCAGGTATGGAAGATGCACCAAGAC] gcgt [CACTCAAGACGCAGTCGGAGGTCACT Dra3 created
              ************
              M------>
     650  GACAGTGCAGACACACGG] a [GAAAGCACTCTAGCGAACAAGAAGGGGGCTTGGATGG
     282  GACAGTGCAGACACACGG] t [GAAAGCACTCTAGCGAACAAGAAGGGGGCTTGGATGG 706  ACAGCACCAAGGCCACAAGGTATTTGGTAAAAACAGAATCATGGATCTTGAGGAACCCTG
     338  ACAGCACCAAGGCCACAAGGTATTTGGTAAAAACAGAATCATGGATCTTGAGGAACCCTG 766  GATATGCCCTGGTGGCAGCCGTCATTGGTTGGATGCTTGGGAGCAACACCATGCAGAGAG
     398  GATATGCCCTGGTGGCAGCCGTCATTGGTTGGATGCTTGGGAGCAACACCATGCAGAGAG E-------------->
     826  TTGTGTTTGTCGTGCTATTGCTTTTGGTGGCCCCAGCTTACAGCTTCAACTGCCTTGGAA
     458  TTGTGTTTGTCGTGCTATTGCTTTTGGTGGCCCCAGCTTACAGCTTCAACTGCCTTGGAA Bgl2 created
                                               ********
     886  TGAGCAACAGAGACTTCTTGGAAGGAGTGTCTGGAGCAACATGGGT] ggatt [TGGTT
     518  TGAGCAACAGAGACTTCTTGGAAGGAGTGTCTGGAGCAACATGGGT] agatc [TGGTT 942  CTCGAAGGCGACAGCTGCGTGACTATCATGTCTAAGGACAAGCCTACCATCGATGTGAAG
     574  CTCGAAGGCGACAGCTGCGTGACTATCATGTCTAAGGACAAGCCTACCATCGATGTGAAG 1002  ATGATGAATATGGAGGCGGCCAACCTGGCAGAGGTCCGCAGTTATTGCTATTTGGCTACC
     634  ATGATGAATATGGAGGCGGCCAACCTGGCAGAGGTCCGCAGTTATTGCTATTTGGCTACC NcoI destroyed
                                            **********
    1062  GTCAGCGATCTCTCCACCAAAGCTGCGTGCCCGAC] c [ATGGGAGAAGCTCACAATGA
     694  GTCAGCGATCTCTCCACCAAAGCTGCGTGCCCGAC] g [ATGGGAGAAGCTCACAATGA 1118  CAAACGTGCTGACCCAGCTTTTGTGTGCAGACAAGGAGTGGTGGACAGGGGCTGGGGCAA
     750  CAAACGTGCTGACCCAGCTTTTGTGTGCAGACAAGGAGTGGTGGACAGGGGCTGGGGCAA 1178  CGGCTGCGGACTATTTGGCAAAGGAAGCATTGACACATGCGCCAAATTTGCCTGCTCTAC
     810  CGGCTGCGGACTATTTGGCAAAGGAAGCATTGACACATGCGCCAAATTTGCCTGCTCTAC 1238  CAAGGCAATAGGAAGAACCATCTTGAAAGAGAATATCAAGTACGAAGTGGCCATTTTTGT
     870  CAAGGCAATAGGAAGAACCATCTTGAAAGAGAATATCAAGTACGAAGTGGCCATTTTTGT 1298  CCATGGACCAACTACTGTGGAGTCGCACGGAAACTACTCCACACAGGTTGGAGCCACTCA
     930  CCATGGACCAACTACTGTGGAGTCGCACGGAAACTACTCCACACAGGTTGGAGCCACTCA
```

FIGURE 3A

```
                    EagI                                        HindIII
                    created                                     destroyed
                    ********                                    ********
      1358    GGC] aggga [GATTCAGCATCACTCCTGCGGCGCCTTCATACACACTAAA] gctt [
       990    GGC] cggcc [GATTCAGCATCACTCCTGCGGCGCCTTCATACACACTAAA] actc [

1410    GGAGAATATGGAGAGGTGACAGTGGACTGTGAACCACGGTCAGGGATTGACACCAATGCA
      1042    GGAGAATATGGAGAGGTGACAGTGGACTGTGAACCACGGTCAGGGATTGACACCAATGCA

1470    TACTACGTGATGACTGTTGGAACAAAGACGTTCTTGGTCCATCGTGAGTGGTTCATGGAC
      1102    TACTACGTGATGACTGTTGGAACAAAGACGTTCTTGGTCCATCGTGAGTGGTTCATGGAC

1530    CTCAACCTCCCTTGGAGCAGTGCTGGAAGTACTGTGTGGAGGAACAGAGAGACGTTAATG
      1162    CTCAACCTCCCTTGGAGCAGTGCTGGAAGTACTGTGTGGAGGAACAGAGAGACGTTAATG

1590    GAGTTTGAGGAACCACACGCCACGAAGCAGTCTGTGATAGCATTGGGCTCACAAGAGGGA
      1222    GAGTTTGAGGAACCACACGCCACGAAGCAGTCTGTGATAGCATTGGGCTCACAAGAGGGA

HindIII destroyed
                    **********
      1650    GCTCTGCATCA] agct [TTGGCTGGAGCCATTCCTGTGGAATTTTCAAGCAACACTGT
      1282    GCTCTGCATCA] ggca [TTGGCTGGAGCCATTCCTGTGGAATTTTCAAGCAACACTGT 1706    CAAGTTGACGTCGGGTCATTTGAAGTGTAGAGTGAAGATGGAAAAATTGCAGTTGAAGGG
      1338    CAAGTTGACGTCGGGTCATTTGAAGTGTAGAGTGAAGATGGAAAAATTGCAGTTGAAGGG 1766    AACAACCTATGGCGTCTGTTCAAAGGCTTTCAAGTTTCTTGGGACTCCCGCAGACACAGG
      1398    AACAACCTATGGCGTCTGTTCAAAGGCTTTCAAGTTTCTTGGGACTCCCGCAGACACAGG 1826    TCACGGCACTGTGGTGTTGGAATTGCAGTACACTGGCACGGATGGACCTTGCAAAGTTCC
      1458    TCACGGCACTGTGGTGTTGGAATTGCAGTACACTGGCACGGATGGACCTTGCAAAGTTCC SpeI created
                                                           **********
      1886    TATCTCGTCAGTGGCTTCATTGAACGACCTAACGCCAGTGGGCAGA] ttg [GTCACTG
      1518    TATCTCGTCAGTGGCTTCATTGAACGACCTAACGCCAGTGGGCAGA] cta [GTCACTG 1942    TCAACCCTTTTGTTTCAGTGGCCACGGCCAACGCTAAGGTCCTGATTGAATTGGAACCAC
      1574    TCAACCCTTTTGTTTCAGTGGCCACGGCCAACGCTAAGGTCCTGATTGAATTGGAACCAC 2002    CCTTTGGAGACTCATACATAGTGGTGGGCAGAGGAGAACAACAGATCAATCACCATTGGC
      1634    CCTTTGGAGACTCATACATAGTGGTGGGCAGAGGAGAACAACAGATCAATCACCATTGGC 2062    ACAAGTCTGGAAGCAGCATTGGCAAAGCCTTTACAACCACCCTCAAAGGAGCGCAGAGAC
      1694    ACAAGTCTGGAAGCAGCATTGGCAAAGCCTTTACAACCACCCTCAAAGGAGCGCAGAGAC 2122    TAGCCGCTCTAGGAGACACAGCTTGGGACTTTGGATCAGTTGGAGGGGTGTTCACCTCAG
      1754    TAGCCGCTCTAGGAGACACAGCTTGGGACTTTGGATCAGTTGGAGGGGTGTTCACCTCAG 2182    TTGGGAAGGCTGTCCATCAAGTGTTCGGAGGAGCATTCCGCTCACTGTTCGGAGGCATGT
      1814    TTGGGAAGGCTGTCCATCAAGTGTTCGGAGGAGCATTCCGCTCACTGTTCGGAGGCATGT 2242    CCTGGATAACGCAAGGATTGCTGGGGGCTCTCCTGTTGTGGATGGGCATCAATGCTCGTG
      1874    CCTGGATAACGCAAGGATTGCTGGGGGCTCTCCTGTTGTGGATGGGCATCAATGCTCGTG 2302    ATAGGTCCATAGCTCTCACGTTTCTCGCAGTTGGAGGAGTTCTGCTCTTCCTCTCCGTGA
      1934    ATAGGTCCATAGCTCTCACGTTTCTCGCAGTTGGAGGAGTTCTGCTCTTCCTCTCCGTGA 2362    ACGTGCACGCT] gacactgggtgtgccatagacatcagccggcaagagctgagatgtgg
      1994    ACGTGCACGCT] ...........................................
```

FIGURE 3B

```
  1                                                 10
  V   T   L   S   N   F   Q   G   K   V   M   M   T   V   N
GTT ACC CTC TCT AAC TTC CAA GGG AAG GTG ATG ATG ACG GTA AAT 20                                              30
  A   T   D   V   T   D   V   I   T   I   P   T   A   A   G
GCT ACT GAC GTC ACA GAT GTC ATC ACG ATT CCA ACA GCT GCT GGA

40
  K   N   L   C   I   V   R   A   M   D   V   G   Y   M   C
AAG AAC CTA TGC ATT GTC AGA GCA ATG GAT GTG GGA TAC ATG TGC 50                                                  60
  D   D   T   I   T   Y   E   C   P   V   L   S   A   G   N
GAT GAT ACT ATC ACT TAT GAA TGC CCA GTG CTG TCG GCT GGT AAT

70
  D   P   E   D   I   D   C   W   C   T   K   S   A   V   Y
GAT CCA GAA GAC ATC GAC TGT TGG TGC ACA AAG TCT GCA GTC TAC 80                                              90
  V   R   Y   G   R   C   T   K   T   R   H   S   R   R   S
GTC AGG TAT GGA AGA TGC ACC AAG ACG CGT CAC TCA AGA CGC AGT

100
  R   R   S   L   T   V   Q   T   H   G   E   S   T   L   A
CGG AGG TCA CTG ACA GTG CAG ACA CAC GGT GAA AGC ACT CTA GCG 110                                             120
  N   K   K   G   A   W   M   D   S   T   K   A   T   R   Y
AAC AAG AAG GGG GCT TGG ATG GAC AGC ACC AAG GCC ACA AGG TAT

130
  L   V   K   T   E   S   W   I   L   R   N   P   G   Y   A
TTG GTA AAA ACA GAA TCA TGG ATC TTG AGG AAC CCT GGA TAT GCC 140                                             150
  L   V   A   A   V   I   G   W   M   L   G   S   N   T   M
CTG GTG GCA GCC GTC ATT GGT TGG ATG CTT GGG AGC AAC ACC ATG

160
  Q   R   V   V   F   V   V   L   L   L   V   A   P   A
CAG AGA GTT GTG TTT GTC GTG CTA TTG CTT TTG GTG GCC CCA GCT 170                                             180
  Y   S   F   N   C   L   G   M   S   N   R   D   F   L   E
TAC AGC TTC AAC TGC CTT GGA ATG AGC AAC AGA GAC TTC TTG GAA

190
  G   V   S   G   A   T   W   V   D   L   V   L   E   G   D
GGA GTG TCT GGA GCA ACA TGG GTA GAT CTG GTT CTC GAA GGC GAC 200                                             210
  S   C   V   T   I   M   S   K   D   K   P   T   I   D   V
AGC TGC GTG ACT ATC ATG TCT AAG GAC AAG CCT ACC ATC GAT GTG

220
  K   M   M   N   M   E   A   A   N   L   A   E   V   R   S
AAG ATG ATG AAT ATG GAG GCG GCC AAC CTG GCA GAG GTC CGC AGT 230                                             240
  Y   C   Y   L   A   T   V   S   D   L   S   T   K   A   A
TAT TGC TAT TTG GCT ACC GTC AGC GAT CTC TCC ACC AAA GCT GCG
```

FIGURE 4A

```
                                        250
  C    P    T    M    G    E    A    H    N    D    K    R    A    D    P
 TGC  CCG  ACG  ATG  GGA  GAA  GCT  CAC  AAT  GAC  AAA  CGT  GCT  GAC  CCA 260                                              270
  A    F    V    C    R    Q    G    V    V    D    R    G    W    G    N
 GCT  TTT  GTG  TGC  AGA  CAA  GGA  GTG  GTG  GAC  AGG  GGC  TGG  GGC  AAC

280
  G    C    G    L    F    G    K    G    S    I    D    T    C    A    K
 GGC  TGC  GGA  CTA  TTT  GGC  AAA  GGA  AGC  ATT  GAC  ACA  TGC  GCC  AAA 290                                              300
  F    A    C    S    T    K    A    I    G    R    T    I    L    K    E
 TTT  GCC  TGC  TCT  ACC  AAG  GCA  ATA  GGA  AGA  ACC  ATC  TTG  AAA  GAG

310
  N    I    K    Y    E    V    A    I    F    V    H    G    P    T    T
 AAT  ATC  AAG  TAC  GAA  GTG  GCC  ATT  TTT  GTC  CAT  GGA  CCA  ACT  ACT 320                                              330
  V    E    S    H    G    N    Y    S    T    Q    V    G    A    T    Q
 GTG  GAG  TCG  CAC  GGA  AAC  TAC  TCC  ACA  CAG  GTT  GGA  GCC  ACT  CAG

340
  A    G    R    F    S    I    T    P    A    A    P    S    Y    T    L
 GCC  GGC  CGA  TTC  AGC  ATC  ACT  CCT  GCG  GCG  CCT  TCA  TAC  ACA  CTA 350                                              360
  K    L    G    E    Y    G    E    V    T    V    D    C    E    P    R
 AAA  CTC  GGA  GAA  TAT  GGA  GAG  GTG  ACA  GTG  GAC  TGT  GAA  CCA  CGG

370
  S    G    I    D    T    N    A    Y    Y    V    M    T    V    G    T
 TCA  GGG  ATT  GAC  ACC  AAT  GCA  TAC  TAC  GTG  ATG  ACT  GTT  GGA  ACA 380                                              390
  K    T    F    L    V    H    R    E    W    F    M    D    L    N    L
 AAG  ACG  TTC  TTG  GTC  CAT  CGT  GAG  TGG  TTC  ATG  GAC  CTC  AAC  CTC

400
  P    W    S    S    A    G    S    T    V    W    R    N    R    E    T
 CCT  TGG  AGC  AGT  GCT  GGA  AGT  ACT  GTG  TGG  AGG  AAC  AGA  GAG  ACG 410                                              420
  L    M    E    F    E    E    P    H    A    T    K    Q    S    V    I
 TTA  ATG  GAG  TTT  GAG  GAA  CCA  CAC  GCC  ACG  AAG  CAG  TCT  GTG  ATA

430
  A    L    G    S    Q    E    G    A    L    H    Q    A    L    A    G
 GCA  TTG  GGC  TCA  CAA  GAG  GGA  GCT  CTG  CAT  CAG  GCA  TTG  GCT  GGA 440                                              450
  A    I    P    V    E    F    S    S    N    T    V    K    L    T    S
 GCC  ATT  CCT  GTG  GAA  TTT  TCA  AGC  AAC  ACT  GTC  AAG  TTG  ACG  TCG

460
  G    H    L    K    C    R    V    K    M    E    K    L    Q    L    K
 GGT  CAT  TTG  AAG  TGT  AGA  GTG  AAG  ATG  GAA  AAA  TTG  CAG  TTG  AAG 470                                              480
  G    T    T    Y    G    V    C    S    K    A    F    K    F    L    G
 GGA  ACA  ACC  TAT  GGC  GTC  TGT  TCA  AAG  GCT  TTC  AAG  TTT  CTT  GGG
```

FIGURE 4B

```
                                490
    T   P   A   D   T   G   H   G   T   V   V   L   E   L   Q
    ACT CCC GCA GAC ACA GGT CAC GGC ACT GTG GTG TTG GAA TTG CAG 500                                         510
    Y   T   G   T   D   G   P   C   K   V   P   I   S   S   V
    TAC ACT GGC ACG GAT GGA CCT TGC AAA GTT CCT ATC TCG TCA GTG

520
    A   S   L   N   D   L   T   P   V   G   R   L   V   T   V
    GCT TCA TTG AAC GAC CTA ACG CCA GTG GGC AGA CTA GTC ACT GTC 530                                         540
    N   P   F   V   S   V   A   T   A   N   A   K   V   L   I
    AAC CCT TTT GTT TCA GTG GCC ACG GCC AAC GCT AAG GTC CTG ATT

550
    E   L   E   P   P   F   G   D   S   Y   I   V   V   G   R
    GAA TTG GAA CCA CCC TTT GGA GAC TCA TAC ATA GTG GTG GGC AGA 560                                     570
    G   E   Q   Q   I   N   H   H   W   H   K   S   G   S   S
    GGA GAA CAA CAG ATC AAT CAC CAT TGG CAC AAG TCT GGA AGC AGC

580
    I   G   K   A   F   T   T   T   L   K   G   A   Q   R   L
    ATT GGC AAA GCC TTT ACA ACC ACC CTC AAA GGA GCG CAG AGA CTA 590                                         600
    A   A   L   G   D   T   A   W   D   F   G   S   V   G   G
    GCC GCT CTA GGA GAC ACA GCT TGG GAC TTT GGA TCA GTT GGA GGG

610
    V   F   T   S   V   G   K   A   V   H   Q   V   F   G   G
    GTG TTC ACC TCA GTT GGG AAG GCT GTC CAT CAA GTG TTC GGA GGA 620                                     630
    A   F   R   S   L   F   G   G   M   S   W   I   T   Q   G
    GCA TTC CGC TCA CTG TTC GGA GGC ATG TCC TGG ATA ACG CAA GGA

640
    L   L   G   A   L   L   L   W   M   G   I   N   A   R   D
    TTG CTG GGG GCT CTC CTG TTG TGG ATG GGC ATC AAT GCT CGT GAT 650                                     660
    R   S   I   A   L   T   F   L   A   V   G   G   V   L   L
    AGG TCC ATA GCT CTC ACG TTT CTC GCA GTT GGA GGA GTT CTG CTC

668
    F   L   S   V   N   V   H   A
    TTC CTC TCC GTG AAC GTG CAC GCT
```

High WNV MoAb control band – defined as 3+

Band intensity = low WNV MoAb is scored 1+

Band intensity > high WNV MoAb is scored 4+

Band intensity between low & high WNV MoAb is scored 2+

Band intensity = high WNV MoAb is scored 3+

(Band intensity visible but < low WNV MoAb is scored +/-)

Low WNV MoAb control band – defined as 1+ ( assay cutoff)

FIGURE 8

```
MetAspAlaMetLysArgGlyLeuCysCysValLeuLeuLeuCysGlyAlaValPheValSerProSerAlaSer
ATGGATGCAATGAAGAGAGGGCTCTGCTGTGTGCTGCTGCTGTGTGGAGCAGTCTTCGTTTCGCCCAGCGCTAGC
TACCTACGTTACTTCTCTCCCGAGACGACACACGACGACGACACACCTCGTCAGAAGCAAAGCGGGTCGCGATCG
```

FIGURE 12

```
                                10                                              20
V   T   L   S   N   F   Q   G   K   V   M   M
GTT ACC CTC TCT AAC TTC CAA GGG AAG GTG ATG ATG 20                                          30
T   V   N   A   T   D   V   T   D   V   I   T   I   P   T   A   A   G   K   N
ACG GTA AAT GCT ACT GAC GTC ACA GAT GTC ATC ACG ATT CCA ACA GCT GCT GGA AAG AAC 40                                          50
L   C   I   V   R   A   M   D   V   G   Y   M   C   D   D   T   I   T   Y   E
CTA TGC ATT GTC AGA GCA ATG GAT GTG GGA TAC ATG TGC GAT GAT ACT ATC ACT TAT GAA 60                                          70
C   P   V   L   S   A   G   N   D   P   E   D   I   D   C   W   C   T   K   S
TGC CCA GTG CTG TCG GCT GGT AAT GAT CCA GAA GAC ATC GAC TGT TGG TGC ACA AAG TCA 80                                          90
A   V   Y   V   R   Y   G   R   C   T   K   T   R   H   S   R   R   S   R   R
GCA GTC TAC GTC AGG TAT GGA AGA TGC ACC AAG ACA CGC CAC TCA AGA CGC AGT CGG AGG 100                                         110
S   L   T   V   Q   T   H   G   E   S   T   L   A   N   K   K   G   A   W   M
TCA CTG ACA GTG CAG ACA CAC GGA GAA AGC ACT CTA GCG AAC AAG AAG GGG GCT TGG ATG 120                                         130
D   S   T   K   A   T   R   Y   L   V   K   T   E   S   W   I   L   R   N   P
GAC AGC ACC AAG GCC ACA AGG TAT TTG GTA AAA ACA GAA TCA TGG ATC TTG AGG AAC CCT 140                                         150
G   Y   A   L   V   A   A   V   I   G   W   M   L   G   S   N   T   M   Q   R
GGA TAT GCC CTG GTG GCA GCC GTC ATT GGT TGG ATG CTT GGG AGC AAC ACC ATG CAG AGA

160
V   V   F   V   V   L   L   L   V   A   P   A   Y   S
GTT GTG TTT GTC GTG CTA TTG CTT TTG GTG GCC CCA GCT TAC AGC
```

FIG. 13

```
F   N   C   L   G
TTC AAC TGC CTT GGA 10                                              20
M   S   N   R   D   F   L   E   G   V   S   G   A   T   W   V   D   L   V   L
ATG AGC AAC AGA GAC TTC TTG GAA GGA GTG TCT GGA GCA ACA TGG GTG GAT TTG GTT CTC 30                                              40
E   G   D   S   C   V   T   I   M   S   K   D   K   P   T   I   D   V   K   M
GAA GGC GAC AGC TGC GTG ACT ATC ATG TCT AAG GAC AAG CCT ACC ATC GAT GTG AAG ATG 50                                              60
M   N   M   E   A   A   N   L   A   E   V   R   S   Y   C   Y   L   A   T   V
ATG AAT ATG GAG GCG GCC AAC CTG GCA GAG GTC CGC AGT TAT TGC TAT TTG GCT ACC GTC 70                                              80
S   D   L   S   T   K   A   A   C   P   T   M   G   E   A   H   N   D   K   R
AGC GAT CTC TCC ACC AAA GCT GCG TGC CCG ACC ATG GGA GAA GCT CAC AAT GAC AAA CGT 90                                              100
A   D   P   A   F   V   C   R   Q   G   V   V   D   R   G   W   G   N   G   C
GCT GAC CCA GCT TTT GTG TGC AGA CAA GGA GTG GTG GAC AGG GGC TGG GGC AAC GGC TGC 110                                             120
G   L   F   G   K   G   S   I   D   T   C   A   K   F   A   C   S   T   K   A
GGA CTA TTT GGC AAA GGA AGC ATT GAC ACA TGC GCC AAA TTT GCC TGC TCT ACC AAG GCA 130                                             140
I   G   R   T   I   L   K   E   N   I   K   Y   E   V   A   I   F   V   H   G
ATA GGA AGA ACC ATC TTG AAA GAG AAT ATC AAG TAC GAA GTG GCC ATT TTT GTC CAT GGA 150                                             160
P   T   T   V   E   S   H   G   N   Y   S   T   Q   V   G   A   T   Q   A   G
CCA ACT ACT GTG GAG TCG CAC GGA AAC TAC TCC ACA CAG GTT GGA GCC ACT CAG GCA GGG 170                                             180
R   F   S   I   T   P   A   A   P   S   Y   T   L   K   L   G   E   Y   G   E
AGA TTC AGC ATC ACT CCT GCG GCG CCT TCA TAC ACA CTA AAG CTT GGA GAA TAT GGA GAG 190                                             200
V   T   V   D   C   E   P   R   S   G   I   D   T   N   A   Y   Y   V   M   T
GTG ACA GTG GAC TGT GAA CCA CGG TCA GGG ATT GAC ACC AAT GCA TAC TAC GTG ATG ACT
```

FIG. 14A

```
              210                                           220
V   G   T   K   T   F   L   V   H   R   E   W   F   M   D   L   N   L   P   W
GTT GGA ACA AAG ACG TTC TTG GTC CAT CGT GAG TGG TTC ATG GAC CTC AAC CTC CCT TGG 230                                           240
S   S   A   G   S   T   V   W   R   N   R   E   T   L   M   E   F   E   E   P
AGC AGT GCT GGA AGT ACT GTG TGG AGG AAC AGA GAG ACG TTA ATG GAG TTT GAG GAA CCA 250                                           260
H   A   T   K   Q   S   V   I   A   L   G   S   Q   E   G   A   L   H   Q   A
CAC GCC ACG AAG CAG TCT GTG ATA GCA TTG GGC TCA CAA GAG GGA GCT CTG CAT CAA GCT 270                                           280
L   A   G   A   I   P   V   E   F   S   S   N   T   V   K   L   T   S   G   H
TTG GCT GGA GCC ATT CCT GTG GAA TTT TCA AGC AAC ACT GTC AAG TTG ACG TCG GGT CAT 290                                           300
L   K   C   R   V   K   M   E   K   L   Q   L   K   G   T   T   Y   G   V   C
TTG AAG TGT AGA GTG AAG ATG GAA AAA TTG CAG TTG AAG GGA ACA ACC TAT GGC GTC TGT 310                                           320
S   K   A   F   K   F   L   G   T   P   A   D   T   G   H   G   T   V   V   L
TCA AAG GCT TTC AAG TTT CTT GGG ACT CCC GCA GAC ACA GGT CAC GGC ACT GTG GTG TTG 330                                           340
E   L   Q   Y   T   G   T   D   G   P   C   K   V   P   I   S   S   V   A   S
GAA TTG CAG TAC ACT GGC ACG GAT GGA CCT TGC AAA GTT CCT ATC TCG TCA GTG GCT TCA 350                                           360
L   N   D   L   T   P   V   G   R   L   V   T   V   N   P   F   V   S   V   A
TTG AAC GAC CTA ACG CCA GTG GGC AGA TTG GTC ACT GTC AAC CCT TTT GTT TCA GTG GCC 370                                           380
T   A   N   A   K   V   L   I   E   L   E   P   P   F   G   D   S   Y   I   V
ACG GCC AAC GCT AAG GTC CTG ATT GAA TTG GAA CCA CCC TTT GGA GAC TCA TAC ATA GTG 390                                           400
V   G   R   G   E   Q   Q   I   N   H   H   W   H   K   S   G   S   S   I   G
GTG GGC AGA GGA GAA CAA CAG ATC AAT CAC CAT TGG CAC AAG TCT GGA AGC AGC ATT GGC 410                                           420
K   A   F   T   T   T   L   K   G   A   Q   R   L   A   A   L   G   D   T   A
AAA GCC TTT ACA ACC ACC CTC AAA GGA GCG CAG AGA CTA GCC GCT CTA GGA GAC ACA GCT 430                                           440
W   D   F   G   S   V   G   G   V   F   T   S   V   G   K   A   V   H   Q   V
TGG GAC TTT GGA TCA GTT GGA GGG GTG TTC ACC TCA GTT GGG AAG GCT GTC CAT CAA GTG 450                                           460
F   G   G   A   F   R   S   L   F   G   G   M   S   W   I   T   Q   G   L   L
TTC GGA GGA GCA TTC CGC TCA CTG TTC GGA GGC ATG TCC TGG ATA ACG CAA GGA TTG CTG
```

FIG. 14B

```
            470                                              480
   G   A   L   L   L   W   M   G   I   N   A   R   D   R   S   I   A   L   T   F
  GGG GCT CTC CTG TTG TGG ATG GGC ATC AAT GCT CGT GAT AGG TCC ATA GCT CTC ACG TTT 490                                              500
   L   A   V   G   G   V   L   L   F   L   S   V   N   V   H   A
  CTC GCA GTT GGA GGA GTT CTG CTC TTC CTC TCC GTG AAC GTG CAC GCT
```

FIG. 14C

SEQUENCE LISTING

<160> NUMBER OF SEQ ID NOS: 12

<210> SEQ ID NO 1
<211> LENGTH: 10299
<212> TYPE: DNA
<213> ORGANISM: West Nile virus

<400> SEQUENCE: 1

```
atgtctaaga aaccaggagg gcccggcaag agccgggctg tcaatatgct aaaacgcgga        60
atgccccgcg tgttgtcctt gattggactg aagagggcta tgttgagcct gatcgacggc       120
aaggggccaa tacgatttgt gttggctctc ttggcgttct tcaggttcac agcaattgct       180
ccgacccgag cagtgctgga tcgatggaga ggtgtgaaca acaaacagc  gatgaaacac       240 cttctgagtt ttaagaagga actagggacc ttgaccagtg ctatcaatcg gcggagctca       300
aaacaaaaga aagaggagg  aaagaccgga attgcagtca tgattggcct gatcgccagc       360
gtaggagcag ttaccctctc taacttccaa gggaaggtga tgatgacggt aaatgctact       420
gacgtcacag atgtcatcac gattccaaca gctgctggaa agaacctatg cattgtcaga       480
gcaatggatg tgggatacat gtgcgatgat actatcactt atgaatgccc agtgctgtcg       540
gctggtaatg atccagaaga catcgactgt tggtgcacaa agtcagcagt ctacgtcagg       600
tatggaagat gcaccaagac acgccactca agacgcagtc ggaggtcact gacagtgcag       660
acacacggag aaagcactct agcgaacaag aaggggcctt ggatggacag caccaaggcc       720
acaaggtatt tggtaaaaac agaatcatgg atcttgagga accctggata tgccctggtg       780
gcagccgtca ttggttggat gcttgggagc aacaccatgc agagagttgt gtttgtcgtg       840
```

```
ctattgcttt tggtggcccc agcttacagc ttcaactgcc ttggaatgag caacagagac     900
ttcttggaag gagtgtctgg agcaacatgg gtggatttgg ttctcgaagg cgacagctgc     960
gtgactatca tgtctaagga caagcctacc atcgatgtga agatgatgaa tatggaggcg    1020
gccaacctgg cagaggtccg cagttattgc tatttggcta ccgtcagcga tctctccacc    1080
aaagctgcgt gcccgaccat gggagaagct cacaatgaca acgtgctga cccagctttt     1140 gtgtgcagac aaggagtggt ggacagggc tggggcaacg gctgcggact atttggcaaa     1200
ggaagcattg acacatgcgc caaatttgcc tgctctacca aggcaatagg aagaaccatc    1260
ttgaaagaga atatcaagta cgaagtggcc atttttgtcc atggaccaac tactgtggag    1320
tcgcacggaa actactccac acaggttgga gccactcagg cagggagatt cagcatcact    1380
cctgcggcgc cttcatacac actaaagctt ggagaatatg gagaggtgac agtggactgt    1440
gaaccacggt cagggattga caccaatgca tactacgtga tgactgttgg aacaaagacg    1500
ttcttggtcc atcgtgagtg gttcatggac ctcaacctcc cttggagcag tgctggaagt    1560
actgtgtgga ggaacagaga gacgttaatg gagtttgagg aaccacacgc cacgaagcag    1620
tctgtgatag cattgggctc acaagaggga gctctgcatc aagctttggc tggagccatt    1680
cctgtggaat tttcaagcaa cactgtcaag ttgacgtcgg gtcatttgaa gtgtagagtg    1740
aagatggaaa aattgcagtt gaagggaaca acctatggcg tctgttcaaa ggctttcaag    1800
tttcttggga ctcccgcaga cacaggtcac ggcactgtgg tgttggaatt gcagtacact    1860
ggcacggatg gaccttgcaa agttcctatc tcgtcagtgg cttcattgaa cgacctaacg    1920
ccagtgggca gattggtcac tgtcaaccct tttgtttcag tggccacggc caacgctaag    1980
gtcctgattg aattggaacc acccttttgga gactcataca tagtggtggg cagaggagaa    2040
caacagatca atcaccattg gcacaagtct ggaagcagca ttggcaaagc ctttacaacc    2100 acccttcaaag gagcgcagag actagccgct ctaggagaca cagcttggga ctttggatca    2160
gttggagggg tgttcacctc agttgggaag gctgtccatc aagtgttcgg aggagcattc    2220
cgctcactgt tcggaggcat gtcctggata acgcaaggat tgctggggc tctcctgttg    2280 tggatgggca tcaatgctcg tgataggtcc atagctctca cgtttctcgc agttggagga    2340
gttctgctct tcctctccgt gaacgtgcac gctgacactg ggtgtgccat agacatcagc    2400
cggcaagagc tgagatgtgg aagtggagtg ttcatacaca atgatgtgga ggcttggatg    2460
gaccggtaca gtattacccc tgaaacgcca caaggcctag ccaagatcat tcagaaagct    2520
cataaggaag gagtgtgcgg tctacgatca gtttccagac tggagcatca aatgtgggaa    2580
gcagtgaagg acgagctgaa cactcttttg aaggagaatg gtgtggacct tagtgtcgtg    2640
gttgagaaac aggagggaat gtacaagtca gcacctaaac gcctcaccgc cacccggaa    2700 aaattggaaa ttggctggaa ggcctgggga aagagtattt tatttgcacc agaactcgcc    2760
aacaacacct ttgtggttga tggtccggag accaaggaat gtccgactca gaatcgcgct    2820
tggaatagct tagaagtgga ggattttgga tttggtctca ccagcactcg gatgttcctg    2880
aaggtcagag agagcaacac aactgaatgt gactcgaaga tcattggaac ggctgtcaag    2940
aacaacttgg cgatccacag tgacctgtcc tattggattg aaagcaggct caatgatacg    3000
tggaagcttg aaagggcagt tctgggtgaa gtcaaatcat gtacgtggcc tgagacgcat    3060
accttgtggg gcgatggaat ccttgagagt gacttgataa taccagtcac actggcggga    3120
ccacgaagca atcacaatcg gagacctggg tacaagacac aaaaccaggg cccatgggac    3180
gaaggccggg tagagattga cttcgattac tgcccaggaa ctacggtcac cctgagtgag    3240
```

```
agctgcggac accgtggacc tgccactcgc accaccacag agagcggaaa gttgataaca   3300
gattggtgct gcaggagctg caccttacca ccactgcgct accaaactga cagcggctgt   3360
tggtatggta tggagatcag accacagaga catgatgaaa agaccctcgt gcagtcacaa   3420
gtgaatgctt ataatgctga tatgattgac ccttttcagt tgggccttct ggtcgtgttc   3480
ttggccaccc aggaggtcct tcgcaagagg tggacagcca agatcagcat gccagctata   3540
ctgattgctc tgctagtcct ggtgtttggg ggcattactt acactgatgt gttacgctat   3600
gtcatcttgg tgggggcagc tttcgcagaa tctaattcgg gaggagacgt ggtacacttg   3660
gcgctcatgg cgaccttcaa gatacaacca gtgtttatgg tggcatcgtt tctcaaagcg   3720
agatggacca accaggagaa cattttgttg atgttggcgg ctgttttctt tcaaatggct   3780
tatcacgatg cccgccaaat tctgctctgg agatccctg atgtgttgaa ttcactggcg   3840
gtagcttgga tgatactgag agccataaca ttcacaacga catcaaacgt ggttgttccg   3900
ctgctagccc tgctaacacc cgggctgaga tgcttgaatc tggatgtgta caggatactg   3960
ctgttgatgg tcggaatagg cagcttgatc agggagaaga ggagtgcagc tgcaaaaaag   4020
aaaggagcaa gtctgctatg cttggctcta gcctcaacag gacttttcaa ccccatgatc   4080
cttgctgctg gactgattgc atgtgatccc aaccgtaaac gcggatggcc cgcaactgaa   4140
gtgatgcacag ctgtcggcct aatgtttgcc atcgtcggag ggctggcaga gcttgacatt   4200
gactccatgg ccattccaat gactatcgcg gggctcatgt tgctgctttt cgtgatttct   4260
gggaaatcaa cagatatgtg gattgagaga acggcggaca tttcctggga aagtgatgca   4320
gaaattacag gctcgagcga aagagttgat gtgcggcttg atgatgatgg aaacttccag   4380
ctcatgaatg atccaggagc accttggaag atatggatgc tcagaatggt ctgtctcgcg   4440
attagtgcgt acaccccctg gcaatcttg ccctcagtag ttggatttg gataactctc   4500
caatacacaa agagaggagg cgtgttgtgg gacactccct caccaaagga gtacaaaaag   4560
ggggacacga ccaccggcgt ctacaggatc atgactcgtg ggctgctcgg cagttatcaa   4620
gcaggagcgg gcgtgatggt tgaaggtgtt ttccacaccc tttggcatac aacaaaagga   4680
gccgctttga tgagcggaga gggccgcctg gacccatact ggggcagtgt caaggaggat   4740
cgactttgtt acgaggacc ctggaaattg cagcacaagt ggaacgggca ggatgaggtg   4800
cagatgattg tggtggaacc tggcaagaac gttaagaacg tccagacgaa accagggtg   4860
ttcaaaacac ctgaaggaga aatcgggggcc gtgactttgg acttcccac tggaacatca   4920
ggctcaccaa tagtggacaa aaacggtgat gtgattgggc tttatggcaa tggagtcata   4980
atgcccaacg gctcatacat aagcgcgata gtgcagggtg aaaggatgga tgagccaatc   5040
ccagccggat tcgaacctga gatgctgagg aaaaaacaga tcactgtact ggatctccat   5100
cccggcgccg gtaaaacaag gaggattctg ccacagatca tcaaagaggc cataaacaga   5160
agactgagaa cagccgtgct agcaccaacc agggttgtgg ctgctgagat ggctgaagca   5220
ctgagaggac tgcccatccg gtaccagaca tccgcagtgc cagaaacaa taatggaaat   5280
gagattgttg atgtcatgtg tcatgctacc ctcacccaca ggctgatgtc tcctcacagg   5340
gtgccgaact acaacctgtt cgtgatggat gaggctcatt tcaccgaccc agctagcatt   5400
gcagcaagag gttacatttc cacaaaggtc gagctagggg aggcggcggc aatattcatg   5460
acagccaccc caccaggcac ttcagatcca ttcccagagt ccaattcacc aatttccgac   5520
ttacagactg agatcccgga tcgagcttgg aactctggat acgaatggat cacagaatac   5580
accgggaaga cggtttggtt tgtgcctagt gtcaagatgg ggaatgagat tgcccttttgc   5640
```

```
ctacaacgtg ctggaaagaa agtagtccaa ttgaacagaa agtcgtacga gacggagtac    5700
ccaaaatgta agaacgatga ttgggacttt gttatcacaa cagacatatc tgaaatgggg    5760
gctaacttca aggcgagcag ggtgattgac agccggaaga gtgtgaaacc aaccatcata    5820
acagaaggag aagggagagt gatcctggga gaaccatctg cagtgacagc agctagtgcc    5880
gcccagagac gtggacgtat cggtagaaat ccgtcgcaag ttggtgatga gtactgttat    5940 gggggcaca cgaatgaaga cgactcgaac ttcgcccatt ggactgaggc acgaatcatg    6000
ctggacaaca tcaacatgcc aaacggactg atcgctcaat tctaccaacc agagcgtgag    6060
aaggtatata ccatggatgg ggaataccgg ctcagaggag aagagagaaa aaactttctg    6120
gaactgttga ggactgcaga tctgccagtt tggctggctt acaaggttgc agcggctgga    6180
gtgtcatacc acgaccggag gtggtgcttt gatggtccta ggacaaacac aattttagaa    6240
gacaacaacg aagtgaagt catcacgaag cttggtgaaa ggaagattct gaggccgcgc    6300
tggattgacg ccagggtgta ctcggatcac caggcactaa aggcgttcaa ggacttcgcc    6360
tcgggaaaac gttctcagat agggctcatt gaggttctgg aaagatgcc tgagcacttc    6420 atggggaaga catgggaagc acttgacacc atgtacgttg tggccactgc agagaaagga    6480
ggaagagctc acagaatggc cctggaggaa ctgccagatg ctcttcagac aattgccttg    6540
attgccttat tgagtgtgat gaccatggga gtattcttcc tcctcatgca gcggaagggc    6600
attggaaaga taggtttggg aggcgctgtc ttgggagtcg gacctttttt ctgttggatg    6660
gctgaagttc caggaacgaa gatcgccgga atgttgctgc tctcccttct cttgatgatt    6720
gtgctaattc ctgagccaga gaagcaacgt tcgcagacag acaaccagct agccgtgttc    6780
ctgatttgtg tcatgaccct tgtgagcgca gtggcagcca acgagatggg ttggctagat    6840
aagaccaaga gtgacataag cagtttgttt gggcaaagaa ttgaggtcaa ggagaatttc    6900
agcatgggag agtttctttt ggacttgagg ccggcaacag cctggtcact gtacgctgtg    6960
acaacagcgg tcctcactcc actgctaaag catttgatca cgtcagatta catcaacacc    7020
tcattgacct caataaacgt tcaggcaagt gcactattca cactcgcgcg aggcttcccc    7080
ttcgtcgatg ttggagtgtc ggctctcctg ctagcagccg gatgctgggg acaagtcacc    7140
ctcaccgtta cggtaacagc ggcaacactc cttttttgcc actatgccta catggttccc    7200
ggttggcaag ctgaggcaat gcgctcagcc cagcggcgga cagcggccgg aatcatgaag    7260
aacgctgtag tggatggcat cgtggccacg gacgtcccag aattagagcg caccacaccc    7320
atcatgcaga agaaagttgg acagatcatg ctgatcttgg tgtctctagc tgcagtagta    7380
gtgaacccgt ctgtgaagac agtacgagaa gccggaattt tgatcacggc cgcagcggtg    7440
acgctttggg agaatggagc aagctctgtt tggaacgcaa caactgccat cggactctgc    7500
cacatcatgc gtgggggttg gttgtcatgt ctatccataa catggacact cataaagaac    7560
atggaaaaac caggactaaa aagaggtggg gcaaaaggac gcaccttggg agaggtttgg    7620
aaagaaagac tcaaccagat gacaaaagaa gagttcacta ggtaccgcaa agaggccatc    7680
atcgaagtcg atcgctcagc ggcaaaacac gccaggaaag aaggcaatgt cactggaggg    7740
catccagtct ctaggggcac agcaaaactg agatggctgg tcgaacggag gtttctcgaa    7800 ccggtcgaa aagtgattga ccttggatgt ggaagaggcg gttggtgtta ctatatggca    7860
acccaaaaaa gagtccaaga agtcagaggg tacacaaagg gcggtccgg acatgaagag    7920 ccccaactag tgcaaagtta tggatggaac attgtcacca tgaagagtgg agtggatgtg    7980
ttctacagac cttctgagtg ttgtgacacc ctcctttgtg acatcggaga gtcctcgtca    8040
```

```
agtgctgagg ttgaagagca taggacgatt cgggtccttg aaatggttga ggactggctg    8100
caccgagggc caagggaatt tgcgtgaag gtgctctgcc cctacatgcc gaaagtcata     8160
gagaagatgg agctgctcca acgccggtat gggggggac tggtcagaaa cccactctca     8220
cggaattcca cgcacgagat gtattgggtg agtcgagctt caggcaatgt ggtacattca    8280
gtgaatatga ccagccaggt gctcctagga agaatggaaa aaaggacctg aagggaccc     8340
caatacgagg aagatgtaaa cttgggaagt ggaaccaggg cggtgggaaa accctgctc     8400
aactcagaca ccagtaaaat caagaacagg attgaacgac tcaggcgtga gtacagttcg    8460
acgtggcacc acgatgagaa ccacccatat agaacctgga actatcacgg cagttatgat    8520
gtgaagccca caggctccgc cagttcgctg tcaatggag tggtcaggct cctctcaaaa     8580
ccatgggaca ccatcacgaa tgttaccacc atggccatga ctgacactac tcccttcggg    8640
cagcagcgag tgttcaaaga aaggtggac acgaaagctc ctgaaccgcc agaaggagtg     8700
aagtacgtgc tcaatgagac caccaactgg ttgtgggcgt ttttggccag agaaaaacgt    8760
cccagaatgt gctctcgaga ggaattcata agaaaggtca acagcaatgc agctttgggt    8820
gccatgtttg aagagcagaa tcaatggagg agcgccagaa aagcagttga agatccaaaa    8880
ttttgggaga tggtggatga ggagcgcgag gcacatctgc gggggaatg tcacacttgc     8940
atttacaaca tgatgggaaa gagagagaaa aaacccggag agttcggaaa ggccaaggga    9000
agcagagcca tttggttcat gtggctcgga gctcgctttc tggagttcga ggctctgggt    9060
tttctcaatg aagaccactg gcttggaaga aagaactcag gaggaggtgt cgagggcttg    9120
ggcctccaaa aactgggtta catcctgcgt gaagttggca cccggcctgg gggcaagatc    9180
tatgctgatg acacagctgg ctgggacacc cgcatcacga gagctgactt ggaaaatgaa    9240
gctaaggtgc ttgagctgct tgatggggaa catcggcgtc ttgccagggc catcattgag    9300
ctcacctatc gtcacaaagt tgtgaaagtg atgcgcccgg ctgctgatgg aagaaccgtc    9360
atggatgtta tctccagaga agatcagagg gggagtggac aagttgtcac ctacgcccta    9420
aacactttca ccaacctggc cgtccagctg gtgaggatga tggaaggga aggagtgatt    9480
ggcccagatg atgtggagaa actcacaaaa gggaaaggac ccaaagtcag gacctggctg    9540
tttgagaatg gggaagaaag actcagccgc atggctgtca gtggagatga ctgtgtggta    9600
aagcccctgg acgatcgctt tgccacctcg ctccacttcc tcaatgctat gtcaaaggtt    9660
cgcaaagaca tccaagagtg gaaaccgtca actggatggt atgattggca gcaggttcca    9720
ttttgctcaa accatttcac tgaattgatc atgaaagatg gaagaacact ggtggttcca    9780
tgccgaggac aggatgaatt ggtaggcaga gctcgcatat ctccagggc cggatggaac    9840
gtccgcgaca ctgcttgtct ggctaagtct tatgcccaga tgtggctgct tctgtacttc    9900
cacagaagag acctgcggct catggccaac gccatttgct ccgctgtccc tgtgaattgg    9960
gtccctaccg aagaaccac gtggtccatc catgcaggag gagagtggat gacaacagag   10020
gacatgttgg aggtctggaa ccgtgtttgg atagaggaga tgaatggat ggaagacaaa    10080
accccagtgg agaaatggag tgacgtccca tattcaggaa aacgagagga catctggtgt   10140
ggcagcctga ttggcacaag agcccgagcc acgtgggcag aaaacatcca ggtggctatc    10200
aaccaagtca gagcaatcat cggagatgag aagtatgtgg attacatgag ttcactaaag   10260
agatatgaag acacaacttt ggttgaggac acagtactg                           10299
```

<210> SEQ ID NO 2
<211> LENGTH: 3433

<212> TYPE: PRT
<213> ORGANISM: West Nile virus

<400> SEQUENCE: 2

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Met Ile Gly Leu Ile Ala Ser Val Gly Ala Val Thr Leu Ser Asn
        115                 120                 125

Phe Gln Gly Lys Val Met Met Thr Val Asn Ala Thr Asp Val Thr Asp
130                 135                 140

Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                165                 170                 175

Pro Val Leu Ser Ala Gly Asn Asp Pro Glu Asp Ile Asp Cys Trp Cys
            180                 185                 190

Thr Lys Ser Ala Val Tyr Val Arg Tyr Gly Arg Cys Thr Lys Thr Arg
        195                 200                 205

His Ser Arg Arg Ser Arg Arg Ser Leu Thr Val Gln Thr His Gly Glu
    210                 215                 220

Ser Thr Leu Ala Asn Lys Lys Gly Ala Trp Met Asp Ser Thr Lys Ala
225                 230                 235                 240

Thr Arg Tyr Leu Val Lys Thr Glu Ser Trp Ile Leu Arg Asn Pro Gly
                245                 250                 255

Tyr Ala Leu Val Ala Ala Val Ile Gly Trp Met Leu Gly Ser Asn Thr
            260                 265                 270

Met Gln Arg Val Val Phe Val Val Leu Leu Leu Leu Val Ala Pro Ala
        275                 280                 285

Tyr Ser Phe Asn Cys Leu Gly Met Ser Asn Arg Asp Phe Leu Glu Gly
    290                 295                 300

Val Ser Gly Ala Thr Trp Val Asp Leu Val Leu Glu Gly Asp Ser Cys
305                 310                 315                 320

Val Thr Ile Met Ser Lys Asp Lys Pro Thr Ile Asp Val Lys Met Met
                325                 330                 335

Asn Met Glu Ala Ala Asn Leu Ala Glu Val Arg Ser Tyr Cys Tyr Leu
            340                 345                 350

Ala Thr Val Ser Asp Leu Ser Thr Lys Ala Ala Cys Pro Thr Met Gly
        355                 360                 365

Glu Ala His Asn Asp Lys Arg Ala Asp Pro Ala Phe Val Cys Arg Gln
    370                 375                 380

Gly Val Val Asp Arg Gly Trp Gly Asn Gly Cys Gly Leu Phe Gly Lys
385                 390                 395                 400
```

```
Gly Ser Ile Asp Thr Cys Ala Lys Phe Ala Cys Ser Thr Lys Ala Ile
            405                 410                 415

Gly Arg Thr Ile Leu Lys Glu Asn Ile Lys Tyr Glu Val Ala Ile Phe
        420                 425                 430

Val His Gly Pro Thr Thr Val Glu Ser His Gly Asn Tyr Ser Thr Gln
    435                 440                 445

Val Gly Ala Thr Gln Ala Gly Arg Phe Ser Ile Thr Pro Ala Ala Pro
450                 455                 460

Ser Tyr Thr Leu Lys Leu Gly Glu Tyr Gly Glu Val Thr Val Asp Cys
465                 470                 475                 480

Glu Pro Arg Ser Gly Ile Asp Thr Asn Ala Tyr Tyr Val Met Thr Val
                485                 490                 495

Gly Thr Lys Thr Phe Leu Val His Arg Glu Trp Phe Met Asp Leu Asn
            500                 505                 510

Leu Pro Trp Ser Ser Ala Gly Ser Thr Val Trp Arg Asn Arg Glu Thr
        515                 520                 525

Leu Met Glu Phe Glu Glu Pro His Ala Thr Lys Gln Ser Val Ile Ala
    530                 535                 540

Leu Gly Ser Gln Glu Gly Ala Leu His Gln Ala Leu Ala Gly Ala Ile
545                 550                 555                 560

Pro Val Glu Phe Ser Ser Asn Thr Val Lys Leu Thr Ser Gly His Leu
                565                 570                 575

Lys Cys Arg Val Lys Met Glu Lys Leu Gln Leu Lys Gly Thr Thr Tyr
            580                 585                 590

Gly Val Cys Ser Lys Ala Phe Lys Phe Leu Gly Thr Pro Ala Asp Thr
        595                 600                 605

Gly His Gly Thr Val Val Leu Glu Leu Gln Tyr Thr Gly Thr Asp Gly
    610                 615                 620

Pro Cys Lys Val Pro Ile Ser Ser Val Ala Ser Leu Asn Asp Leu Thr
625                 630                 635                 640

Pro Val Gly Arg Leu Val Thr Val Asn Pro Phe Val Ser Val Ala Thr
                645                 650                 655

Ala Asn Ala Lys Val Leu Ile Glu Leu Glu Pro Pro Phe Gly Asp Ser
            660                 665                 670

Tyr Ile Val Val Gly Arg Gly Glu Gln Gln Ile Asn His His Trp His
        675                 680                 685

Lys Ser Gly Ser Ser Ile Gly Lys Ala Phe Thr Thr Thr Leu Lys Gly
    690                 695                 700

Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
                725                 730                 735

Gly Gly Ala Phe Arg Ser Leu Phe Gly Gly Met Ser Trp Ile Thr Gln
            740                 745                 750

Gly Leu Leu Gly Ala Leu Leu Leu Trp Met Gly Ile Asn Ala Arg Asp
        755                 760                 765

Arg Ser Ile Ala Leu Thr Phe Leu Ala Val Gly Gly Val Leu Leu Phe
    770                 775                 780

Leu Ser Val Asn Val His Ala Asp Thr Gly Cys Ala Ile Asp Ile Ser
785                 790                 795                 800

Arg Gln Glu Leu Arg Cys Gly Ser Gly Val Phe Ile His Asn Asp Val
                805                 810                 815

Glu Ala Trp Met Asp Arg Tyr Lys Tyr Tyr Pro Glu Thr Pro Gln Gly
            820                 825                 830
```

-continued

Leu Ala Lys Ile Ile Gln Lys Ala His Lys Glu Gly Val Cys Gly Leu
        835                 840                 845

Arg Ser Val Ser Arg Leu Glu His Gln Met Trp Glu Ala Val Lys Asp
        850                 855                 860

Glu Leu Asn Thr Leu Leu Lys Glu Asn Gly Val Asp Leu Ser Val Val
865                 870                 875                 880

Val Glu Lys Gln Glu Gly Met Tyr Lys Ser Ala Pro Lys Arg Leu Thr
                    885                 890                 895

Ala Thr Thr Glu Lys Leu Glu Ile Gly Trp Lys Ala Trp Gly Lys Ser
                900                 905                 910

Ile Leu Phe Ala Pro Glu Leu Ala Asn Asn Thr Phe Val Val Asp Gly
        915                 920                 925

Pro Glu Thr Lys Glu Cys Pro Thr Gln Asn Arg Ala Trp Asn Ser Leu
        930                 935                 940

Glu Val Glu Asp Phe Gly Phe Gly Leu Thr Ser Thr Arg Met Phe Leu
945                 950                 955                 960

Lys Val Arg Glu Ser Asn Thr Thr Glu Cys Asp Ser Lys Ile Ile Gly
                965                 970                 975

Thr Ala Val Lys Asn Asn Leu Ala Ile His Ser Asp Leu Ser Tyr Trp
                980                 985                 990

Ile Glu Ser Arg Leu Asn Asp Thr Trp Lys Leu Glu Arg Ala Val Leu
                995                 1000                1005

Gly Glu Val Lys Ser Cys Thr Trp Pro Glu Thr His Thr Leu Trp
        1010                1015                1020

Gly Asp Gly Ile Leu Glu Ser Asp Leu Ile Ile Pro Val Thr Leu
        1025                1030                1035

Ala Gly Pro Arg Ser Asn His Asn Arg Arg Pro Gly Tyr Lys Thr
        1040                1045                1050

Gln Asn Gln Gly Pro Trp Asp Glu Gly Arg Val Glu Ile Asp Phe
        1055                1060                1065

Asp Tyr Cys Pro Gly Thr Thr Val Thr Leu Ser Glu Ser Cys Gly
        1070                1075                1080

His Arg Gly Pro Ala Thr Arg Thr Thr Thr Glu Ser Gly Lys Leu
        1085                1090                1095

Ile Thr Asp Trp Cys Cys Arg Ser Cys Thr Leu Pro Pro Leu Arg
        1100                1105                1110

Tyr Gln Thr Asp Ser Gly Cys Trp Tyr Gly Met Glu Ile Arg Pro
        1115                1120                1125

Gln Arg His Asp Glu Lys Thr Leu Val Gln Ser Gln Val Asn Ala
        1130                1135                1140

Tyr Asn Ala Asp Met Ile Asp Pro Phe Gln Leu Gly Leu Leu Val
        1145                1150                1155

Val Phe Leu Ala Thr Gln Glu Val Leu Arg Lys Arg Trp Thr Ala
        1160                1165                1170

Lys Ile Ser Met Pro Ala Ile Leu Ile Ala Leu Leu Val Leu Val
        1175                1180                1185

Phe Gly Gly Ile Thr Tyr Thr Asp Val Leu Arg Tyr Val Ile Leu
        1190                1195                1200

Val Gly Ala Ala Phe Ala Glu Ser Asn Ser Gly Gly Asp Val Val
        1205                1210                1215

His Leu Ala Leu Met Ala Thr Phe Lys Ile Gln Pro Val Phe Met
        1220                1225                1230

Val Ala Ser Phe Leu Lys Ala Arg Trp Thr Asn Gln Glu Asn Ile

```
             1235                1240                1245

Leu Leu Met Leu Ala Ala Val Phe Phe Gln Met Ala Tyr His Asp
    1250                1255                1260

Ala Arg Gln Ile Leu Leu Trp Glu Ile Pro Asp Val Leu Asn Ser
    1265                1270                1275

Leu Ala Val Ala Trp Met Ile Leu Arg Ala Ile Thr Phe Thr Thr
    1280                1285                1290

Thr Ser Asn Val Val Val Pro Leu Leu Ala Leu Leu Thr Pro Gly
    1295                1300                1305

Leu Arg Cys Leu Asn Leu Asp Val Tyr Arg Ile Leu Leu Leu Met
    1310                1315                1320

Val Gly Ile Gly Ser Leu Ile Arg Glu Lys Arg Ser Ala Ala Ala
    1325                1330                1335

Lys Lys Lys Gly Ala Ser Leu Leu Cys Leu Ala Leu Ala Ser Thr
    1340                1345                1350

Gly Leu Phe Asn Pro Met Ile Leu Ala Ala Gly Leu Ile Ala Cys
    1355                1360                1365

Asp Pro Asn Arg Lys Arg Gly Trp Pro Ala Thr Glu Val Met Thr
    1370                1375                1380

Ala Val Gly Leu Met Phe Ala Ile Val Gly Gly Leu Ala Glu Leu
    1385                1390                1395

Asp Ile Asp Ser Met Ala Ile Pro Met Thr Ile Ala Gly Leu Met
    1400                1405                1410

Phe Ala Ala Phe Val Ile Ser Gly Lys Ser Thr Asp Met Trp Ile
    1415                1420                1425

Glu Arg Thr Ala Asp Ile Ser Trp Glu Ser Asp Ala Glu Ile Thr
    1430                1435                1440

Gly Ser Ser Glu Arg Val Asp Val Arg Leu Asp Asp Gly Asn
    1445                1450                1455

Phe Gln Leu Met Asn Asp Pro Gly Ala Pro Trp Lys Ile Trp Met
    1460                1465                1470

Leu Arg Met Val Cys Leu Ala Ile Ser Ala Tyr Thr Pro Trp Ala
    1475                1480                1485

Ile Leu Pro Ser Val Val Gly Phe Trp Ile Thr Leu Gln Tyr Thr
    1490                1495                1500

Lys Arg Gly Gly Val Leu Trp Asp Thr Pro Ser Pro Lys Glu Tyr
    1505                1510                1515

Lys Lys Gly Asp Thr Thr Thr Gly Val Tyr Arg Ile Met Thr Arg
    1520                1525                1530

Gly Leu Leu Gly Ser Tyr Gln Ala Gly Ala Gly Val Met Val Glu
    1535                1540                1545

Gly Val Phe His Thr Leu Trp His Thr Thr Lys Gly Ala Ala Leu
    1550                1555                1560

Met Ser Gly Glu Gly Arg Leu Asp Pro Tyr Trp Gly Ser Val Lys
    1565                1570                1575

Glu Asp Arg Leu Cys Tyr Gly Gly Pro Trp Lys Leu Gln His Lys
    1580                1585                1590

Trp Asn Gly Gln Asp Glu Val Gln Met Ile Val Val Glu Pro Gly
    1595                1600                1605

Lys Asn Val Lys Asn Val Gln Thr Lys Pro Gly Val Phe Lys Thr
    1610                1615                1620

Pro Glu Gly Glu Ile Gly Ala Val Thr Leu Asp Phe Pro Thr Gly
    1625                1630                1635
```

```
Thr Ser Gly Ser Pro Ile Val Asp Lys Asn Gly Asp Val Ile Gly
    1640                1645                1650

Leu Tyr Gly Asn Gly Val Ile Met Pro Asn Gly Ser Tyr Ile Ser
    1655                1660                1665

Ala Ile Val Gln Gly Glu Arg Met Asp Glu Pro Ile Pro Ala Gly
    1670                1675                1680

Phe Glu Pro Glu Met Leu Arg Lys Lys Gln Ile Thr Val Leu Asp
    1685                1690                1695

Leu His Pro Gly Ala Gly Lys Thr Arg Arg Ile Leu Pro Gln Ile
    1700                1705                1710

Ile Lys Glu Ala Ile Asn Arg Arg Leu Arg Thr Ala Val Leu Ala
    1715                1720                1725

Pro Thr Arg Val Val Ala Ala Glu Met Ala Glu Ala Leu Arg Gly
    1730                1735                1740

Leu Pro Ile Arg Tyr Gln Thr Ser Ala Val Pro Arg Glu His Asn
    1745                1750                1755

Gly Asn Glu Ile Val Asp Val Met Cys His Ala Thr Leu Thr His
    1760                1765                1770

Arg Leu Met Ser Pro His Arg Val Pro Asn Tyr Asn Leu Phe Val
    1775                1780                1785

Met Asp Glu Ala His Phe Thr Asp Pro Ala Ser Ile Ala Ala Arg
    1790                1795                1800

Gly Tyr Ile Ser Thr Lys Val Glu Leu Gly Glu Ala Ala Ala Ile
    1805                1810                1815

Phe Met Thr Ala Thr Pro Pro Gly Thr Ser Asp Pro Phe Pro Glu
    1820                1825                1830

Ser Asn Ser Pro Ile Ser Asp Leu Gln Thr Glu Ile Pro Asp Arg
    1835                1840                1845

Ala Trp Asn Ser Gly Tyr Glu Trp Ile Thr Glu Tyr Thr Gly Lys
    1850                1855                1860

Thr Val Trp Phe Val Pro Ser Val Lys Met Gly Asn Glu Ile Ala
    1865                1870                1875

Leu Cys Leu Gln Arg Ala Gly Lys Lys Val Val Gln Leu Asn Arg
    1880                1885                1890

Lys Ser Tyr Glu Thr Glu Tyr Pro Lys Cys Lys Asn Asp Asp Trp
    1895                1900                1905

Asp Phe Val Ile Thr Thr Asp Ile Ser Glu Met Gly Ala Asn Phe
    1910                1915                1920

Lys Ala Ser Arg Val Ile Asp Ser Arg Lys Ser Val Lys Pro Thr
    1925                1930                1935

Ile Ile Thr Glu Gly Glu Gly Arg Val Ile Leu Gly Glu Pro Ser
    1940                1945                1950

Ala Val Thr Ala Ala Ser Ala Ala Gln Arg Arg Gly Arg Ile Gly
    1955                1960                1965

Arg Asn Pro Ser Gln Val Gly Asp Glu Tyr Cys Tyr Gly Gly His
    1970                1975                1980

Thr Asn Glu Asp Asp Ser Asn Phe Ala His Trp Thr Glu Ala Arg
    1985                1990                1995

Ile Met Leu Asp Asn Ile Asn Met Pro Asn Gly Leu Ile Ala Gln
    2000                2005                2010

Phe Tyr Gln Pro Glu Arg Glu Lys Val Tyr Thr Met Asp Gly Glu
    2015                2020                2025

Tyr Arg Leu Arg Gly Glu Glu Arg Lys Asn Phe Leu Glu Leu Leu
    2030                2035                2040
```

```
Arg Thr Ala Asp Leu Pro Val Trp Leu Ala Tyr Lys Val Ala Ala
    2045            2050                2055
Ala Gly Val Ser Tyr His Asp Arg Arg Trp Cys Phe Asp Gly Pro
    2060            2065                2070
Arg Thr Asn Thr Ile Leu Glu Asp Asn Asn Glu Val Glu Val Ile
    2075            2080                2085
Thr Lys Leu Gly Glu Arg Lys Ile Leu Arg Pro Arg Trp Ile Asp
    2090            2095                2100
Ala Arg Val Tyr Ser Asp His Gln Ala Leu Lys Ala Phe Lys Asp
    2105            2110                2115
Phe Ala Ser Gly Lys Arg Ser Gln Ile Gly Leu Ile Glu Val Leu
    2120            2125                2130
Gly Lys Met Pro Glu His Phe Met Gly Lys Thr Trp Glu Ala Leu
    2135            2140                2145
Asp Thr Met Tyr Val Val Ala Thr Ala Glu Lys Gly Gly Arg Ala
    2150            2155                2160
His Arg Met Ala Leu Glu Glu Leu Pro Asp Ala Leu Gln Thr Ile
    2165            2170                2175
Ala Leu Ile Ala Leu Leu Ser Val Met Thr Met Gly Val Phe Phe
    2180            2185                2190
Leu Leu Met Gln Arg Lys Gly Ile Gly Lys Ile Gly Leu Gly Gly
    2195            2200                2205
Ala Val Leu Gly Val Ala Thr Phe Phe Cys Trp Met Ala Glu Val
    2210            2215                2220
Pro Gly Thr Lys Ile Ala Gly Met Leu Leu Leu Ser Leu Leu Leu
    2225            2230                2235
Met Ile Val Leu Ile Pro Glu Pro Glu Lys Gln Arg Ser Gln Thr
    2240            2245                2250
Asp Asn Gln Leu Ala Val Phe Leu Ile Cys Val Met Thr Leu Val
    2255            2260                2265
Ser Ala Val Ala Ala Asn Glu Met Gly Trp Leu Asp Lys Thr Lys
    2270            2275                2280
Ser Asp Ile Ser Ser Leu Phe Gly Gln Arg Ile Glu Val Lys Glu
    2285            2290                2295
Asn Phe Ser Met Gly Glu Phe Leu Leu Asp Leu Arg Pro Ala Thr
    2300            2305                2310
Ala Trp Ser Leu Tyr Ala Val Thr Thr Ala Val Leu Thr Pro Leu
    2315            2320                2325
Leu Lys His Leu Ile Thr Ser Asp Tyr Ile Asn Thr Ser Leu Thr
    2330            2335                2340
Ser Ile Asn Val Gln Ala Ser Ala Leu Phe Thr Leu Ala Arg Gly
    2345            2350                2355
Phe Pro Phe Val Asp Val Gly Val Ser Ala Leu Leu Leu Ala Ala
    2360            2365                2370
Gly Cys Trp Gly Gln Val Thr Leu Thr Val Thr Val Thr Ala Ala
    2375            2380                2385
Thr Leu Leu Phe Cys His Tyr Ala Tyr Met Val Pro Gly Trp Gln
    2390            2395                2400
Ala Glu Ala Met Arg Ser Ala Gln Arg Arg Thr Ala Ala Gly Ile
    2405            2410                2415
Met Lys Asn Ala Val Val Asp Gly Ile Val Ala Thr Asp Val Pro
    2420            2425                2430
Glu Leu Glu Arg Thr Thr Pro Ile Met Gln Lys Lys Val Gly Gln
```

-continued

```
              2435                2440                2445

Ile Met  Leu Ile Leu Val  Ser Leu Ala Ala Val  Val Val Asn Pro
    2450             2455                 2460

Ser Val  Lys Thr Val Arg  Glu Ala Gly Ile Leu  Ile Thr Ala Ala
    2465             2470                 2475

Ala Val  Thr Leu Trp Glu  Asn Gly Ala Ser Ser  Val Trp Asn Ala
    2480             2485                 2490

Thr Thr  Ala Ile Gly Leu  Cys His Ile Met Arg  Gly Gly Trp Leu
    2495             2500                 2505

Ser Cys  Leu Ser Ile Thr  Trp Thr Leu Ile Lys  Asn Met Glu Lys
    2510             2515                 2520

Pro Gly  Leu Lys Arg Gly  Gly Ala Lys Gly Arg  Thr Leu Gly Glu
    2525             2530                 2535

Val Trp  Lys Glu Arg Leu  Asn Gln Met Thr Lys  Glu Glu Phe Thr
    2540             2545                 2550

Arg Tyr  Arg Lys Glu Ala  Ile Ile Glu Val Asp  Arg Ser Ala Ala
    2555             2560                 2565

Lys His  Ala Arg Lys Glu  Gly Asn Val Thr Gly  Gly His Pro Val
    2570             2575                 2580

Ser Arg  Gly Thr Ala Lys  Leu Arg Trp Leu Val  Glu Arg Arg Phe
    2585             2590                 2595

Leu Glu  Pro Val Gly Lys  Val Ile Asp Leu Gly  Cys Gly Arg Gly
    2600             2605                 2610

Gly Trp  Cys Tyr Tyr Met  Ala Thr Gln Lys Arg  Val Gln Glu Val
    2615             2620                 2625

Arg Gly  Tyr Thr Lys Gly  Gly Pro Gly His Glu  Glu Pro Gln Leu
    2630             2635                 2640

Val Gln  Ser Tyr Gly Trp  Asn Ile Val Thr Met  Lys Ser Gly Val
    2645             2650                 2655

Asp Val  Phe Tyr Arg Pro  Ser Glu Cys Cys Asp  Thr Leu Leu Cys
    2660             2665                 2670

Asp Ile  Gly Glu Ser Ser  Ser Ser Ala Glu Val  Glu Glu His Arg
    2675             2680                 2685

Thr Ile  Arg Val Leu Glu  Met Val Glu Asp Trp  Leu His Arg Gly
    2690             2695                 2700

Pro Arg  Glu Phe Cys Val  Lys Val Leu Cys Pro  Tyr Met Pro Lys
    2705             2710                 2715

Val Ile  Glu Lys Met Glu  Leu Leu Gln Arg Arg  Tyr Gly Gly Gly
    2720             2725                 2730

Leu Val  Arg Asn Pro Leu  Ser Arg Asn Ser Thr  His Glu Met Tyr
    2735             2740                 2745

Trp Val  Ser Arg Ala Ser  Gly Asn Val Val His  Ser Val Asn Met
    2750             2755                 2760

Thr Ser  Gln Val Leu Leu  Gly Arg Met Glu Lys  Arg Thr Trp Lys
    2765             2770                 2775

Gly Pro  Gln Tyr Glu Glu  Asp Val Asn Leu Gly  Ser Gly Thr Arg
    2780             2785                 2790

Ala Val  Gly Lys Pro Leu  Leu Asn Ser Asp Thr  Ser Lys Ile Lys
    2795             2800                 2805

Asn Arg  Ile Glu Arg Leu  Arg Arg Glu Tyr Ser  Ser Thr Trp His
    2810             2815                 2820

His Asp  Glu Asn His Pro  Tyr Arg Thr Trp Asn  Tyr His Gly Ser
    2825             2830                 2835
```

```
Tyr Asp Val Lys Pro Thr Gly Ser Ala Ser Ser Leu Val Asn Gly
2840                2845                2850

Val Val Arg Leu Leu Ser Lys Pro Trp Asp Thr Ile Thr Asn Val
2855                2860                2865

Thr Thr Met Ala Met Thr Asp Thr Thr Pro Phe Gly Gln Gln Arg
2870                2875                2880

Val Phe Lys Glu Lys Val Asp Thr Lys Ala Pro Glu Pro Pro Glu
2885                2890                2895

Gly Val Lys Tyr Val Leu Asn Glu Thr Thr Asn Trp Leu Trp Ala
2900                2905                2910

Phe Leu Ala Arg Glu Lys Arg Pro Arg Met Cys Ser Arg Glu Glu
2915                2920                2925

Phe Ile Arg Lys Val Asn Ser Asn Ala Ala Leu Gly Ala Met Phe
2930                2935                2940

Glu Glu Gln Asn Gln Trp Arg Ser Ala Arg Glu Ala Val Glu Asp
2945                2950                2955

Pro Lys Phe Trp Glu Met Val Asp Glu Glu Arg Glu Ala His Leu
2960                2965                2970

Arg Gly Glu Cys His Thr Cys Ile Tyr Asn Met Met Gly Lys Arg
2975                2980                2985

Glu Lys Lys Pro Gly Glu Phe Gly Lys Ala Lys Gly Ser Arg Ala
2990                2995                3000

Ile Trp Phe Met Trp Leu Gly Ala Arg Phe Leu Glu Phe Glu Ala
3005                3010                3015

Leu Gly Phe Leu Asn Glu Asp His Trp Leu Gly Arg Lys Asn Ser
3020                3025                3030

Gly Gly Gly Val Glu Gly Leu Gly Leu Gln Lys Leu Gly Tyr Ile
3035                3040                3045

Leu Arg Glu Val Gly Thr Arg Pro Gly Gly Lys Ile Tyr Ala Asp
3050                3055                3060

Asp Thr Ala Gly Trp Asp Thr Arg Ile Thr Arg Ala Asp Leu Glu
3065                3070                3075

Asn Glu Ala Lys Val Leu Glu Leu Leu Asp Gly Glu His Arg Arg
3080                3085                3090

Leu Ala Arg Ala Ile Ile Glu Leu Thr Tyr Arg His Lys Val Val
3095                3100                3105

Lys Val Met Arg Pro Ala Ala Asp Gly Arg Thr Val Met Asp Val
3110                3115                3120

Ile Ser Arg Glu Asp Gln Arg Gly Ser Gly Gln Val Val Thr Tyr
3125                3130                3135

Ala Leu Asn Thr Phe Thr Asn Leu Ala Val Gln Leu Val Arg Met
3140                3145                3150

Met Glu Gly Glu Gly Val Ile Gly Pro Asp Asp Val Glu Lys Leu
3155                3160                3165

Thr Lys Gly Lys Gly Pro Lys Val Arg Thr Trp Leu Phe Glu Asn
3170                3175                3180

Gly Glu Glu Arg Leu Ser Arg Met Ala Val Ser Gly Asp Asp Cys
3185                3190                3195

Val Val Lys Pro Leu Asp Asp Arg Phe Ala Thr Ser Leu His Phe
3200                3205                3210

Leu Asn Ala Met Ser Lys Val Arg Lys Asp Ile Gln Glu Trp Lys
3215                3220                3225

Pro Ser Thr Gly Trp Tyr Asp Trp Gln Gln Val Pro Phe Cys Ser
3230                3235                3240
```

Asn His Phe Thr Glu Leu Ile Met Lys Asp Gly Arg Thr Leu Val
    3245                3250                3255

Val Pro Cys Arg Gly Gln Asp Glu Leu Val Gly Arg Ala Arg Ile
    3260                3265                3270

Ser Pro Gly Ala Gly Trp Asn Val Arg Asp Thr Ala Cys Leu Ala
    3275                3280                3285

Lys Ser Tyr Ala Gln Met Trp Leu Leu Leu Tyr Phe His Arg Arg
    3290                3295                3300

Asp Leu Arg Leu Met Ala Asn Ala Ile Cys Ser Ala Val Pro Val
    3305                3310                3315

Asn Trp Val Pro Thr Gly Arg Thr Thr Trp Ser Ile His Ala Gly
    3320                3325                3330

Gly Glu Trp Met Thr Thr Glu Asp Met Leu Glu Val Trp Asn Arg
    3335                3340                3345

Val Trp Ile Glu Glu Asn Glu Trp Met Glu Asp Lys Thr Pro Val
    3350                3355                3360

Glu Lys Trp Ser Asp Val Pro Tyr Ser Gly Lys Arg Glu Asp Ile
    3365                3370                3375

Trp Cys Gly Ser Leu Ile Gly Thr Arg Ala Arg Ala Thr Trp Ala
    3380                3385                3390

Glu Asn Ile Gln Val Ala Ile Asn Gln Val Arg Ala Ile Ile Gly
    3395                3400                3405

Asp Glu Lys Tyr Val Asp Tyr Met Ser Ser Leu Lys Arg Tyr Glu
    3410                3415                3420

Asp Thr Thr Leu Val Glu Asp Thr Val Leu
    3425                3430

```
<210> SEQ ID NO 3
<211> LENGTH: 2060
<212> TYPE: DNA
<213> ORGANISM: West Nile virus

<400> SEQUENCE: 3
```

| | | | | | |
|---|---|---|---|---|---|
| gtaggagcag | ttaccctctc | taacttccaa | gggaaggtga | tgatgacggt | aaatgctact | 60 |
| gacgtcacag | atgtcatcac | gattccaaca | gctgctggaa | agaacctatg | cattgtcaga | 120 |
| gcaatggatg | tgggatacat | gtgcgatgat | actatcactt | atgaatgccc | agtgctgtcg | 180 |
| gctggtaatg | atccagaaga | catcgactgt | tggtgcacaa | agtcagcagt | ctacgtcagg | 240 |
| tatggaagat | gcaccaagac | acgccactca | agacgcagtc | ggaggtcact | gacagtgcag | 300 |
| acacacggag | aaagcactct | agcgaacaag | aaggggggctt | ggatggacag | caccaaggcc | 360 |
| acaaggtatt | tggtaaaaac | agaatcatgg | atcttgagga | accctggata | tgccctggtg | 420 |
| gcagccgtca | ttggttggat | gcttgggagc | aacaccatgc | agagagttgt | gtttgtcgtg | 480 |
| ctattgcttt | tggtggcccc | agcttacagc | ttcaactgcc | ttggaatgag | caacagagac | 540 |
| ttcttggaag | gagtgtctgg | agcaacatgg | gtggatttgg | ttctcgaagg | cgacagctgc | 600 |
| gtgactatca | tgtctaagga | caagcctacc | atcgatgtga | agatgatgaa | tatggaggcg | 660 |
| gccaacctgg | cagaggtccg | cagttattgc | tatttggcta | ccgtcagcga | tctctccacc | 720 |
| aaagctgcgt | gcccgaccat | gggagaagct | cacaatgaca | aacgtgctga | cccagctttt | 780 |
| gtgtgcagac | aaggagtggt | ggacaggggc | tgggcaacg | gctgcggact | atttggcaaa | 840 |
| ggaagcattg | acatgcgc | caaatttgcc | tgctctacca | aggcaatagg | aagaaccatc | 900 |
| ttgaaagaga | atatcaagta | cgaagtggcc | attttcgtcc | atggaccaac | tactgtggag | 960 |

-continued

```
tcgcacggaa actactccac acaggttgga gccactcagg cagggagatt cagcatcact    1020
cctgcggcgc cttcatacac actaaagctt ggagaatatg gagaggtgac agtggactgt    1080
gaaccacggt cagggattga caccaatgca tactacgtga tgactgttgg aacaaagacg    1140
ttcttggtcc atcgtgagtg gttcatggac ctcaacctcc cttggagcag tgctggaagt    1200
actgtgtgga ggaacagaga gacgttaatg gagtttgagg aaccacacgc cacgaagcag    1260
tctgtgatag cattgggctc acaagaggga gctctgcatc aagctttggc tggagccatt    1320
cctgtggaat tttcaagcaa cactgtcaag ttgacgtcgg gtcatttgaa gtgtagagtg    1380
aagatggaaa aattgcagtt gaagggaaca acctatggcg tctgttcaaa ggctttcaag    1440
tttcttggga ctcccgcaga cacaggtcac ggcactgtgg tgttggaatt gcagtacact    1500
ggcacggatg gaccttgcaa agttcctatc tcgtcagtgg cttcattgaa cgacctaacg    1560
ccagtgggca gattggtcac tgtcaaccct tttgtttcag tggccacggc caacgctaag    1620
gtcctgattg aattggaacc accctttgga gactcataca tagtggtggg cagaggagaa    1680
caacagatca atcaccattg gcacaagtct ggaagcagca ttggcaaagc ctttacaacc    1740
accctcaaag gagcgcagag actagccgct ctaggagaca cagcttggga ctttggatca    1800
gttggagggg tgttcacctc agttgggaag gctgtccatc aagtgttcgg aggagcattc    1860
cgctcactgt tcggaggcat gtcctggata acgcaaggat tgctggggc tctcctgttg    1920 tggatgggca tcaatgctcg tgataggtcc atagctctca cgtttctcgc agttggagga    1980
gttctgctct tcctctccgt gaacgtgcac gctgacactg ggtgtgccat agacatcagc    2040
cggcaagagc tgagatgtgg                                               2060
```

<210> SEQ ID NO 4
<211> LENGTH: 2004
<212> TYPE: DNA
<213> ORGANISM: Artificial Sequence
<220> FEATURE:
<223> OTHER INFORMATION: synthetic nucleotide sequence of the PrM/E
region of WNV strain NY99

<400> SEQUENCE: 4

```
gttaccctct ctaacttcca agggaaggtg atgatgacgg taaatgctac tgacgtcaca      60
gatgtcatca cgattccaac agctgctgga aagaacctat gcattgtcag agcaatggat     120
gtgggataca tgtgcgatga tactatcact tatgaatgcc cagtgctgtc ggctggtaat     180
gatccagaag acatcgactg ttggtgcaca aagtctgcag tctacgtcag gtatggaaga     240
tgcaccaaga cgcgtcactc aagacgcagt cggaggtcac tgacagtgca gacacacggt     300
gaaagcactc tagcgaacaa gaagggggct tggatggaca gcaccaaggc cacaaggtat     360
ttggtaaaaa cagaatcatg gatcttgagg aaccctggat atgccctggt ggcagccgtc     420
attggttgga tgcttgggag caacaccatg cagagagttg tgtttgtcgt gctattgctt     480
ttggtggccc cagcttacag cttcaactgc cttggaatga gcaacagaga cttcttggaa     540
ggagtgtctg gagcaacatg gtagatctg gttctcgaag cgacagctg cgtgactatc     600 atgtctaagg acaagcctac catcgatgtg aagatgatga tatgagc ggccaacctg       660 gcagaggtcc gcagttattg ctatttggct accgtcagcg atctctccac caaagctgcg     720
tgcccgacga tgggagaagc tcacaatgac aaacgtgctg acccagcttt tgtgtgcaga     780
caaggagtgg tggacagggg ctgggcaac ggctgcggac tatttggcaa aggaagcatt    840
gacacatgcg ccaaatttgc ctgctctacc aaggcaatag aagaaccat cttgaaagag     900 aatatcaagt acgaagtggc cattttttgtc catggaccaa ctactgtgga gtcgcacgga     960
```

```
aactactcca cacaggttgg agccactcag gccggccgat tcagcatcac tcctgcggcg    1020
ccttcataca cactaaaact cggagaatat ggagaggtga cagtggactg tgaaccacgg    1080
tcagggattg acaccaatgc atactacgtg atgactgttg aacaaagac gttcttggtc     1140 catcgtgagt ggttcatgga cctcaacctc ccttggagca gtgctggaag tactgtgtgg    1200
aggaacagag agacgttaat ggagtttgag gaaccacacg ccacgaagca gtctgtgata    1260
gcattgggct cacaagaggg agctctgcat caggcattgg ctggagccat tcctgtggaa    1320
ttttcaagca acactgtcaa gttgacgtcg ggtcatttga agtgtagagt gaagatggaa    1380
aaattgcagt tgaagggaac aacctatggc gtctgttcaa aggctttcaa gtttcttggg    1440
actcccgcag acacaggtca cggcactgtg gtgttggaat tgcagtacac tggcacggat    1500
ggaccttgca aagttcctat ctcgtcagtg gcttcattga acgacctaac gccagtgggc    1560
agactagtca ctgtcaaccc ttttgtttca gtggccacgg ccaacgctaa ggtcctgatt    1620
gaattggaac caccctttgg agactcatac atagtggtgg gcagaggaga acaacagatc    1680
aatcaccatt ggcacaagtc tggaagcagc attggcaaag cctttacaac caccctcaaa    1740
ggagcgcaga gactagccgc tctaggagac acagcttggg actttggatc agttggaggg    1800
gtgttcacct cagttgggaa ggctgtccat caagtgttcg gaggagcatt ccgctcactg    1860
ttcggaggca tgtcctggat aacgcaagga ttgctggggg ctctcctgtt gtggatgggc    1920
atcaatgctc gtgataggtc catagctctc acgtttctcg cagttggagg agttctgctc    1980
ttcctctccg tgaacgtgca cgct                                           2004

<210> SEQ ID NO 5
<211> LENGTH: 2004
<212> TYPE: DNA
<213> ORGANISM: Artificial Sequence
<220> FEATURE:
<223> OTHER INFORMATION: synthetic  WNV PrM/E construct

<400> SEQUENCE: 5
gttaccctct ctaacttcca agggaaggtg atgatgacgg taaatgctac tgacgtcaca     60
gatgtcatca cgattccaac agctgctgga aagaacctat gcattgtcag agcaatggat    120
gtgggataca tgtgcgatga tactatcact tatgaatgcc cagtgctgtc ggctggtaat    180
gatccagaag acatcgactg ttggtgcaca aagtctgcag tctacgtcag gtatggaaga    240
tgcaccaaga cgcgtcactc aagacgcagt cggaggtcac tgacagtgca gacacacggt    300
gaaagcactc tagcgaacaa gagggggct tggatggaca gcaccaaggc cacaaggtat    360
ttggtaaaaa cagaatcatg gatcttgagg aaccctggat atgccctggt ggcagccgtc    420
attggttgga tgcttgggag caacaccatg cagagagttg tgtttgtcgt gctattgctt    480
ttggtggccc cagcttacag cttcaactgc cttggaatga gcaacagaga cttcttggaa    540
ggagtgtctg gagcaacatg ggtagatctg gttctcgaag gcgacagctg cgtgactatc    600
atgtctaagg acaagcctac catcgatgtg aagatgatga atatggaggc ggccaacctg    660
gcagaggtcc gcagttattg ctatttggct accgtcagcg atctctccac caaagctgcg    720
tgcccgacga tggagaagc tcacaatgac aaacgtgctg acccagcttt tgtgtgcaga    780
caaggagtgg tggacagggg ctgggcaac ggctgcggac tatttggcaa aggaagcatt    840
gacacatgcg ccaaatttgc ctgctctacc aaggcaatag gaagaaccat cttgaaagag    900
aatatcaagt acgaagtggc cattttttgtc catggaccaa ctactgtgga gtcgcacgga    960
aactactcca cacaggttgg agccactcag gccggccgat tcagcatcac tcctgcggcg    1020
```

```
ccttcataca cactaaaact cggagaatat ggagaggtga cagtggactg tgaaccacgg    1080
tcagggattg acaccaatgc atactacgtg atgactgttg gaacaaagac gttcttggtc    1140
catcgtgagt ggttcatgga cctcaacctc ccttggagca gtgctggaag tactgtgtgg    1200
aggaacagag agacgttaat ggagtttgag gaaccacacg ccacgaagca gtctgtgata    1260
gcattgggct cacaagaggg agctctgcat caggcattgg ctggagccat tcctgtggaa    1320
ttttcaagca acactgtcaa gttgacgtcg ggtcatttga agtgtagagt gaagatggaa    1380
aaattgcagt tgaagggaac aacctatggc gtctgttcaa aggctttcaa gtttcttggg    1440
actcccgcag acacaggtca cggcactgtg gtgttggaat gcagtacac tggcacggat     1500 ggaccttgca aagttcctat ctcgtcagtg gcttcattga cgacctaac gccagtgggc     1560 agactagtca ctgtcaaccc ttttgtttca gtggccacgg ccaacgctaa ggtcctgatt    1620
gaattggaac acccctttgg agactcatac atagtggtgg cagaggaga acaacagatc     1680 aatcaccatt ggcacaagtc tggaagcagc attggcaaag cctttacaac caccctcaaa    1740
ggagcgcaga gactagccgc tctaggagac acagcttggg actttggatc agttggaggg    1800
gtgttcacct cagttgggaa ggctgtccat caagtgttcg gaggagcatt ccgctcactg    1860
ttcggaggca tgtcctggat aacgcaagga ttgctggggg ctctcctgtt gtggatgggc    1920
atcaatgctc gtgataggtc catagctctc acgtttctcg cagttggagg agttctgctc    1980
ttcctctccg tgaacgtgca cgct                                           2004

<210> SEQ ID NO 6
<211> LENGTH: 668
<212> TYPE: PRT
<213> ORGANISM: Artificial Sequence
<220> FEATURE:
<223> OTHER INFORMATION: synthetic  WNV PrM/E construct

<400> SEQUENCE: 6

Val Thr Leu Ser Asn Phe Gln Gly Lys Val Met Met Thr Val Asn Ala
1               5                   10                  15

Thr Asp Val Thr Asp Val Ile Thr Ile Pro Thr Ala Ala Gly Lys Asn
            20                  25                  30

Leu Cys Ile Val Arg Ala Met Asp Val Gly Tyr Met Cys Asp Asp Thr
        35                  40                  45

Ile Thr Tyr Glu Cys Pro Val Leu Ser Ala Gly Asn Asp Pro Glu Asp
    50                  55                  60

Ile Asp Cys Trp Cys Thr Lys Ser Ala Val Tyr Val Arg Tyr Gly Arg
65                  70                  75                  80

Cys Thr Lys Thr Arg His Ser Arg Arg Ser Arg Ser Leu Thr Val
                85                  90                  95

Gln Thr His Gly Glu Ser Thr Leu Ala Asn Lys Lys Gly Ala Trp Met
            100                 105                 110

Asp Ser Thr Lys Ala Thr Arg Tyr Leu Val Lys Thr Glu Ser Trp Ile
        115                 120                 125

Leu Arg Asn Pro Gly Tyr Ala Leu Val Ala Ala Ile Gly Trp Met
    130                 135                 140

Leu Gly Ser Asn Thr Met Gln Arg Val Val Phe Val Val Leu Leu Leu
145                 150                 155                 160

Leu Val Ala Pro Ala Tyr Ser Phe Asn Cys Leu Gly Met Ser Asn Arg
                165                 170                 175

Asp Phe Leu Glu Gly Val Ser Gly Ala Thr Trp Val Asp Leu Val Leu
            180                 185                 190
```

```
Glu Gly Asp Ser Cys Val Thr Ile Met Ser Lys Asp Lys Pro Thr Ile
            195                 200                 205
Asp Val Lys Met Met Asn Met Glu Ala Ala Asn Leu Ala Glu Val Arg
        210                 215                 220
Ser Tyr Cys Tyr Leu Ala Thr Val Ser Asp Leu Ser Thr Lys Ala Ala
225                 230                 235                 240
Cys Pro Thr Met Gly Glu Ala His Asn Asp Lys Arg Ala Asp Pro Ala
                245                 250                 255
Phe Val Cys Arg Gln Gly Val Val Asp Arg Gly Trp Gly Asn Gly Cys
            260                 265                 270
Gly Leu Phe Gly Lys Gly Ser Ile Asp Thr Cys Ala Lys Phe Ala Cys
        275                 280                 285
Ser Thr Lys Ala Ile Gly Arg Thr Ile Leu Lys Glu Asn Ile Lys Tyr
290                 295                 300
Glu Val Ala Ile Phe Val His Gly Pro Thr Thr Val Glu Ser His Gly
305                 310                 315                 320
Asn Tyr Ser Thr Gln Val Gly Ala Thr Gln Ala Gly Arg Phe Ser Ile
                325                 330                 335
Thr Pro Ala Ala Pro Ser Tyr Thr Leu Lys Leu Gly Glu Tyr Gly Glu
            340                 345                 350
Val Thr Val Asp Cys Glu Pro Arg Ser Gly Ile Asp Thr Asn Ala Tyr
        355                 360                 365
Tyr Val Met Thr Val Gly Thr Lys Thr Phe Leu Val His Arg Glu Trp
    370                 375                 380
Phe Met Asp Leu Asn Leu Pro Trp Ser Ser Ala Gly Ser Thr Val Trp
385                 390                 395                 400
Arg Asn Arg Glu Thr Leu Met Glu Phe Glu Pro His Ala Thr Lys
                405                 410                 415
Gln Ser Val Ile Ala Leu Gly Ser Gln Glu Gly Ala Leu His Gln Ala
            420                 425                 430
Leu Ala Gly Ala Ile Pro Val Glu Phe Ser Ser Asn Thr Val Lys Leu
        435                 440                 445
Thr Ser Gly His Leu Lys Cys Arg Val Lys Met Glu Lys Leu Gln Leu
450                 455                 460
Lys Gly Thr Thr Tyr Gly Val Cys Ser Lys Ala Phe Lys Phe Leu Gly
465                 470                 475                 480
Thr Pro Ala Asp Thr Gly His Gly Thr Val Val Leu Glu Leu Gln Tyr
                485                 490                 495
Thr Gly Thr Asp Gly Pro Cys Lys Val Pro Ile Ser Ser Val Ala Ser
            500                 505                 510
Leu Asn Asp Leu Thr Pro Val Gly Arg Leu Val Thr Val Asn Pro Phe
        515                 520                 525
Val Ser Val Ala Thr Ala Asn Ala Lys Val Leu Ile Glu Leu Glu Pro
530                 535                 540
Pro Phe Gly Asp Ser Tyr Ile Val Val Gly Arg Gly Glu Gln Gln Ile
545                 550                 555                 560
Asn His His Trp His Lys Ser Gly Ser Ser Ile Gly Lys Ala Phe Thr
                565                 570                 575
Thr Thr Leu Lys Gly Ala Gln Arg Leu Ala Ala Leu Gly Asp Thr Ala
            580                 585                 590
Trp Asp Phe Gly Ser Val Gly Gly Val Phe Thr Ser Val Gly Lys Ala
        595                 600                 605
Val His Gln Val Phe Gly Gly Ala Phe Arg Ser Leu Phe Gly Gly Met
```

```
                610                 615                 620
Ser Trp Ile Thr Gln Gly Leu Leu Gly Ala Leu Leu Trp Met Gly
625                 630                 635                 640

Ile Asn Ala Arg Asp Arg Ser Ile Ala Leu Thr Phe Leu Ala Val Gly
                645                 650                 655

Gly Val Leu Leu Phe Leu Ser Val Asn Val His Ala
                660                 665

<210> SEQ ID NO 7
<211> LENGTH: 25
<212> TYPE: PRT
<213> ORGANISM: Artificial Sequence
<220> FEATURE:
<223> OTHER INFORMATION: synthetic TPA leader

<400> SEQUENCE: 7

Met Asp Ala Met Lys Arg Gly Leu Cys Cys Val Leu Leu Cys Gly
1               5                   10                  15

Ala Val Phe Val Ser Pro Ser Ala Ser
                20                  25

<210> SEQ ID NO 8
<211> LENGTH: 501
<212> TYPE: DNA
<213> ORGANISM: West Nile virus

<400> SEQUENCE: 8
gttaccctct ctaacttcca agggaaggtg atgatgacgg taaatgctac tgacgtcaca      60
gatgtcatca cgattccaac agctgctgga agaacctat  gcattgtcag agcaatggat     120
gtgggataca tgtgcgatga tactatcact tatgaatgcc cagtgctgtc ggctggtaat     180
gatccagaag acatcgactg ttggtgcaca aagtcagcag tctacgtcag gtatggaaga     240
tgcaccaaga cacgccactc aagacgcagt cggaggtcac tgacagtgca gacacacgga     300
gaaagcactc tagcgaacaa gaaggggct  tggatggaca gcaccaaggc cacaaggtat     360
ttggtaaaaa cagaatcatg gatcttgagg aaccctggat atgccctggt ggcagccgtc     420
attggttgga tgcttgggag caacaccatg cagagagttg tgtttgtcgt gctattgctt     480
ttggtggccc cagcttacag c                                               501

<210> SEQ ID NO 9
<211> LENGTH: 167
<212> TYPE: PRT
<213> ORGANISM: West Nile virus

<400> SEQUENCE: 9

Val Thr Leu Ser Asn Phe Gln Gly Lys Val Met Met Thr Val Asn Ala
1               5                   10                  15

Thr Asp Val Thr Asp Val Ile Thr Ile Pro Thr Ala Ala Gly Lys Asn
                20                  25                  30

Leu Cys Ile Val Arg Ala Met Asp Val Gly Tyr Met Cys Asp Asp Thr
            35                  40                  45

Ile Thr Tyr Glu Cys Pro Val Leu Ser Ala Gly Asn Asp Pro Glu Asp
        50                  55                  60

Ile Asp Cys Trp Cys Thr Lys Ser Ala Val Tyr Val Arg Tyr Gly Arg
65                  70                  75                  80

Cys Thr Lys Thr Arg His Ser Arg Arg Ser Arg Arg Ser Leu Thr Val
                85                  90                  95

Gln Thr His Gly Glu Ser Thr Leu Ala Asn Lys Lys Gly Ala Trp Met
```

```
                      100                 105                 110
Asp Ser Thr Lys Ala Thr Arg Tyr Leu Val Lys Thr Glu Ser Trp Ile
        115                 120                 125

Leu Arg Asn Pro Gly Tyr Ala Leu Val Ala Ala Val Ile Gly Trp Met
    130                 135                 140

Leu Gly Ser Asn Thr Met Gln Arg Val Val Phe Val Val Leu Leu Leu
145                 150                 155                 160

Leu Val Ala Pro Ala Tyr Ser
                165

<210> SEQ ID NO 10
<211> LENGTH: 1503
<212> TYPE: DNA
<213> ORGANISM: West Nile virus

<400> SEQUENCE: 10
ttcaactgcc ttggaatgag caacagagac ttcttggaag gagtgtctgg agcaacatgg      60
gtggatttgg ttctcgaagg cgacagctgc gtgactatca tgtctaagga caagcctacc     120
atcgatgtga agatgatgaa tatggaggcg gccaacctgg cagaggtccg cagttattgc     180
tatttggcta ccgtcagcga tctctccacc aaagctgcgt gcccgaccat gggagaagct     240
cacaatgaca acgtgctga cccagctttt gtgtgcagac aaggagtggt ggacaggggc     300
tggggcaacg gctgcggact atttggcaaa ggaagcattg acacatgcgc caaatttgcc     360
tgctctacca aggcaatagg aagaaccatc ttgaaagaga atatcaagta cgaagtggcc     420
atttttgtcc atggaccaac tactgtggag tcgcacggaa actactccac acaggttgga     480
gccactcagg cagggagatt cagcatcact cctgcggcgc cttcatacac actaaagctt     540
ggagaatatg gagaggtgac agtggactgt gaaccacggt cagggattga caccaatgca     600
tactacgtga tgactgttgg aacaaagacg ttcttggtcc atcgtgagtg gttcatggac     660
ctcaacctcc cttggagcag tgctggaagt actgtgtgga ggaacagaga gacgttaatg     720
gagtttgagg aaccacacgc cacgaagcag tctgtgatag cattgggctc acaagaggga     780
gctctgcatc aagcttttgc tggagccatt cctgtgaat tttcaagcaa cactgtcaag     840
ttgacgtcgg gtcatttgaa gtgtagagtg aagatggaaa aattgcagtt gaagggaaca     900
acctatggcg tctgttcaaa ggcttttcaag tttcttggga ctcccgcaga cacaggtcac     960
ggcactgtgg tgttggaatt gcagtacact ggcacggatg gaccttgcaa agttcctatc    1020
tcgtcagtgg cttcattgaa cgacctaacg ccagtgggca gattggtcac tgtcaaccct    1080
tttgtttcag tggccacggc caacgctaag gtcctgattg aattggaacc accctttgga    1140
gactcataca tagtggtggg cagaggagaa caacagatca tcaccattg cacaagtct    1200 ggaagcagca ttggcaaagc ctttacaacc accctcaaag gagcgcagag actagccgct    1260
ctaggagaca cagcttggga cttttggatca gttggagggg tgttcacctc agttgggaag    1320
gctgtccatc aagtgttcgg aggagcattc cgctcactgt tcggaggcat gtcctggata    1380
acgcaaggat tgctggggc tctcctgttg tggatgggca tcaatgctcg tgataggtcc    1440
atagctctca cgtttctcgc agttggagga gttctgctct tcctctccgt gaacgtgcac    1500
gct                                                                 1503

<210> SEQ ID NO 11
<211> LENGTH: 501
<212> TYPE: PRT
<213> ORGANISM: West Nile virus
```

<400> SEQUENCE: 11

```
Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Glu Val Arg Ser Tyr Cys Tyr Leu Ala Thr
    50                  55                  60

Val Ser Asp Leu Ser Thr Lys Ala Ala Cys Pro Thr Met Gly Glu Ala
65                  70                  75                  80

His Asn Asp Lys Arg Ala Asp Pro Ala Phe Val Cys Arg Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Ser Thr Lys Ala Ile Gly Arg
        115                 120                 125

Thr Ile Leu Lys Glu Asn Ile Lys Tyr Glu Val Ala Ile Phe Val His
130                 135                 140

Gly Pro Thr Thr Val Glu Ser His Gly Asn Tyr Ser Thr Gln Val Gly
145                 150                 155                 160

Ala Thr Gln Ala Gly Arg Phe Ser Ile Thr Pro Ala Ala Pro Ser Tyr
                165                 170                 175

Thr Leu Lys Leu Gly Glu Tyr Gly Glu Val Thr Val Asp Cys Glu Pro
            180                 185                 190

Arg Ser Gly Ile Asp Thr Asn Ala Tyr Tyr Val Met Thr Val Gly Thr
        195                 200                 205

Lys Thr Phe Leu Val His Arg Glu Trp Phe Met Asp Leu Asn Leu Pro
210                 215                 220

Trp Ser Ser Ala Gly Ser Thr Val Trp Arg Asn Arg Glu Thr Leu Met
225                 230                 235                 240

Glu Phe Glu Glu Pro His Ala Thr Lys Gln Ser Val Ile Ala Leu Gly
                245                 250                 255

Ser Gln Glu Gly Ala Leu His Gln Ala Leu Ala Gly Ala Ile Pro Val
            260                 265                 270

Glu Phe Ser Ser Asn Thr Val Lys Leu Thr Ser Gly His Leu Lys Cys
        275                 280                 285

Arg Val Lys Met Glu Lys Leu Gln Leu Lys Gly Thr Thr Tyr Gly Val
290                 295                 300

Cys Ser Lys Ala Phe Lys Phe Leu Gly Thr Pro Ala Asp Thr Gly His
305                 310                 315                 320

Gly Thr Val Val Leu Glu Leu Gln Tyr Thr Gly Thr Asp Gly Pro Cys
                325                 330                 335

Lys Val Pro Ile Ser Ser Val Ala Ser Leu Asn Asp Leu Thr Pro Val
            340                 345                 350

Gly Arg Leu Val Thr Val Asn Pro Phe Val Ser Val Ala Thr Ala Asn
        355                 360                 365

Ala Lys Val Leu Ile Glu Leu Glu Pro Pro Phe Gly Asp Ser Tyr Ile
370                 375                 380

Val Val Gly Arg Gly Glu Gln Gln Ile Asn His His Trp His Lys Ser
385                 390                 395                 400

Gly Ser Ser Ile Gly Lys Ala Phe Thr Thr Thr Leu Lys Gly Ala Gln
                405                 410                 415
```

```
                                            -continued

Arg Leu Ala Ala Leu Gly Asp Thr Ala Trp Asp Phe Gly Ser Val Gly
            420                 425                 430

Gly Val Phe Thr Ser Val Gly Lys Ala Val His Gln Val Phe Gly Gly
        435                 440                 445

Ala Phe Arg Ser Leu Phe Gly Gly Met Ser Trp Ile Thr Gln Gly Leu
    450                 455                 460

Leu Gly Ala Leu Leu Leu Trp Met Gly Ile Asn Ala Arg Asp Arg Ser
465                 470                 475                 480

Ile Ala Leu Thr Phe Leu Ala Val Gly Gly Val Leu Leu Phe Leu Ser
                485                 490                 495

Val Asn Val His Ala
            500

<210> SEQ ID NO 12
<211> LENGTH: 75
<212> TYPE: DNA
<213> ORGANISM: Artificial Sequence
<220> FEATURE:
<223> OTHER INFORMATION: synthetic TPA leader

<400> SEQUENCE: 12
atggatgcaa tgaagagagg gctctgctgt gtgctgctgc tgtgtggagc agtcttcgtt      60
tcgcccagcg ctagc                                                      75
```

IMMUNOGENIC REAGENTS FROM WEST NILE VIRUS

CROSS-REFERENCE TO RELATED APPLICATION

This application is a 35 U.S.C. §371 filing of PCT/US2004/015976, filed May 21, 2004, from which priority is claimed under 35 U.S.C. §120, which in turn claims the benefit of U.S. application Ser. Nos. 60/473,225, filed May 23, 2003, and 60/529,171, filed Dec. 11, 2003, from which applications priority is claimed pursuant to 35 U.S.C. §119(e), and all of which applications are incorporated herein by reference in their entireties.

TECHNICAL FIELD

The present invention pertains generally to West Nile Virus (WNV). In particular, the invention relates to immunogenic reagents derived from WNV for use in immunogenic compositions for diagnosis, prevention and treatment of WNV infection, as well as sensitive methods for detecting the presence of WNV in biological samples.

BACKGROUND

West Nile virus (WNV) is a mosquito-borne flavivirus that infects humans, horses, and birds. The virus is transmitted to humans and several animal species through mosquitoes that acquire the virus by feeding on infected birds. The virus is indigenous to Africa, Asia, Europe, and Australia, and has recently caused large epidemics in the Western Hemisphere, including in Europe and the United States. WNV was first detected in North America in 1999 during an epidemic of meningoencephalitis in New York City. WNV seroprevalence studies in Queens, New York showed evidence of prior infection in 2.6% of the population, age 5 or older. During 1999-2002, the virus extended its range throughout much of the eastern United States. The range of WNV infections within the Western Hemisphere is expected to continue to expand.

Human WNV infections are often subclinical but clinical infections can range in severity from uncomplicated fever to fatal meningoencephalitis. The incidence of severe neuroinvasive disease and death increases with age. Epidemics of WNV encephalitis and meningitis raise concerns that transmission of WNV may occur through voluntary blood donations.

As with other flaviviruses, WNV possesses a single-stranded plus-sense RNA genome of approximately 10,000 nucleotides. The genome contains a single open reading frame (ORF) of about 10,300 nucleotides that encodes a polyprotein that is proteolytically processed into 10 mature viral proteins, in the order of $NH_2$—C—PrM-E-NS1-NS2A-NS2B-NS3-NS4A-NS4B-NS5-COOH. The three structural proteins, capsid (C), membrane (PrM), and envelope (E), are encoded within the 5' portion of the ORF, while the seven nonstructural proteins, NS1, NS2A, NS2B, NS3, NS4A, NS4B and NS5, are encoded within the 3' portion. The boundaries of these proteins, numbered relative to the nucleotide sequence of WNV, strain NY99, are as follows: C, 97-465; pr, 466-741; M, 742-986; E, 987-2469; NS1, 2470-3525; NS2A, 3526-4218; NS2B, 4219-4611; NS3, 4612-6458; NS4A, 6459-6915; NS4B, 6916-7680; NS5, 7681-10395. For a review of WNV and its molecular biology and structure, see, Brinton, M. A., *Ann. Rev. Microbiol.* (2002) 56:371-402; and Lanciotti et al., *Science* (1999) 286:2333-2337.

To date, no effective prevention or treatment of WNV infection exists. Currently, public education and mosquito abatement programs are used to curb transmission of the virus. However, rapid intervention is critical in order to reduce the risk to humans. Traditionally, detection of virus has been accomplished by testing mosquitoes and dead birds for the presence of virus using cell culture methods and immunoassay techniques. However, these methods are extremely time consuming and can take a week or more to complete.

The diagnosis of WNV infection in humans can be established by the presence of WNV IgM antibody in serum or cerebrospinal fluid (CSF), increases in WNV antibody detected by ELISA or WNV neutralizing antibody. However, confirmation of the type of infecting virus is possible only by detection of a fourfold or greater rise in virus-specific neutralizing antibody titers in either CSF or serum by performing plaque reduction neutralization assays with several flaviviruses. Virus isolation in cell culture from CSF and serum has generally been unsuccessful, likely due to the low level and short-lived viremia associated with infection. Additionally, most immunological tests are indirect, and nonspecific antigen-antibody reactions can occur and result in false-positive determinations. Hence, immunological methods for successfully diagnosing WNV infection are greatly needed.

Attempts have been made to develop vaccines for WNV. In particular, killed virus vaccines, a live attenuated chimeric virus vaccine and passive immunization with WNV-immune serum have been studied. Tesh et al., *Emerg. Infect. Dis.* (2002) 8:1392-1397; Malkinson et al., *Ann. N.Y. Acad. Sci.* (2001) 951:255-261; Monath et al., *Curr. Drug Targets Infect. Disord.* (2001) 1:37-50. The WNV E protein has been produced recombinantly and administered to mice. See, U.S. Patent Publication No. 2003/0148261; Wang et al., *J. Immunol.* (2001) 167:5273-5277. Wang et al., *Ann. NY Acad. Sci.* (2001) 951:325-327 report the passive immunization of mice with rabbit anti-E protein sera. PCT Publication No. WO 02/083903 describes the use of WNV peptides in vaccines.

DNA vaccines including either WNV PrM-E or C have also been studied. See, Davis et al., *J. Virol.* (2001) 75:4040-4047; Chang et al., *Ann. NY Acad. Sci.* (2001) 951:272-285; Yang et al., *J. Infect. Dis.* (2001) 184:809-816; U.S. Patent Publication Nos. 2003/0022849, 2003/0104008 and 2003/0091595. For example, Davis et al. *J. Virol.* (2001) 75:4040-4047 describes a DNA construct encoding PrM and E proteins under the control of the Japanese encephalitis virus signal sequence. The recombinant antigen expressed by the construct is assembled and secreted in the form of extracellular subviral particles. U.S. Patent Publication No. 2002/0164349 reports the recombinant production of a WNV capsid protein and immunization using a plasmid encoding the capsid.

Nevertheless, there remains an urgent need for immunogenic reagents for use in vaccines and as diagnostics for WNV.

SUMMARY OF THE INVENTION

The present invention is based in part, on the successful recombinant production of immunogenic WNV proteins. These proteins, polynucleotides encoding the proteins, and combinations thereof, as well as antibodies produced therefrom, can be used in immunogenic compositions for preventing, treating and diagnosing WNV infection. The use of recombinant techniques to produce the WNV products described herein provides protein preparations devoid of other molecules normally present, such as other viral contaminants and harmful proteins. Moreover, the proteins can be provided in a highly purified state and act as highly immunogenic reagents in diagnostic and detection assays and vaccine compositions. Using the methods of the invention, infected samples can be identified and excluded from the blood supply for transfusion, as well as for the preparation of blood derivatives.

Accordingly, in one embodiment, the invention is directed to an isolated immunogenic composition comprising at least one WNV PrM/E heterodimer, the heterodimer consisting of a recombinant WNV PrM polypeptide and a recombinant WNV E polypeptide.

In certain embodiments, the recombinant WNV PrM polypeptide comprises the contiguous sequence of amino acids depicted at positions 1-167 of FIG. 13 (positions 124-290 of FIGS. 2A-2N), or an amino acid sequence having at least 75% sequence identity thereto, such as 80%, 85%, 90%, 95%, and so on, sequence identity thereto.

In additional embodiments, the recombinant WNV E polypeptide comprises the contiguous sequence of amino acids depicted at positions 1-501 of FIGS. 14A-14C (positions 291-791 of FIGS. 2A-2N), or an amino acid sequence having at least 75% sequence identity thereto, such as 80%, 85%, 90%, 95%, and so on, sequence identity thereto.

In still further embodiments, the recombinant WNV PrM polypeptide comprises the contiguous sequence of amino acids depicted at positions 1-167 of FIG. 13 (positions 124-290 of FIGS. 2A-2N) and said recombinant WNV E polypeptide comprises the contiguous sequence of amino acids depicted at positions 1-501 of FIGS. 14A-14C (positions 291-791 of FIGS. 2A-2N).

In another embodiment, the invention is directed to an isolated immunogenic composition comprising a complex of at least about 4 WNV PrM/E heterodimers, each heterodimer consisting of a recombinant WNV PrM polypeptide and a recombinant WNV E polypeptide.

In certain embodiments, the recombinant WNV PrM polypeptide of the heterodimer comprises the contiguous sequence of amino acids depicted at positions 1-167 of FIG. 13 (positions 124-290 of FIGS. 2A-2N), or an amino acid sequence having at least 75% sequence identity thereto, such as 80%, 85%, 90%, 95%, and so on, sequence identity thereto.

In additional embodiments, the recombinant WNV E polypeptide of the heterodimer comprises the contiguous sequence of amino acids depicted at positions 1-501 of FIGS. 14A-14C (positions 291-791 of FIGS. 2A-2N), or an amino acid sequence having at least 75% sequence identity thereto, such as 80%, 85%, 90%, 95%, and so on, sequence identity thereto.

In yet further embodiments the recombinant WNV PrM polypeptide in the heterodimer comprises the contiguous sequence of amino acids depicted at positions 1-167 of FIG. 13 (positions 124-290 of FIGS. 2A-2N), and said recombinant WNV E polypeptide comprises the contiguous sequence of amino acids depicted at positions 1-501 of FIGS. 14A-14C (positions 291-791 of FIGS. 2A-2N).

In an additional embodiment, the various immunogenic compositions described above are substantially free of WNV M polypeptide.

In certain embodiments, the various immunogenic compositions described above further comprise an adjuvant, such as but not limited to an adjuvant selected from the group consisting of Alum, MF-59, CpG, and ISCOMS.

In additional embodiments, the various immunogenic compositions described above further comprise a pharmaceutically acceptable carrier vehicle.

In yet further embodiments, the invention is directed to a method of immunizing an animal against WNV which comprises administering to the animal any of the immunogenic compositions described above.

In additional embodiments, the invention is directed to a recombinant polynucleotide vector comprising a nucleic acid encoding a WNV polyprotein, wherein the nucleic acid encodes, in 5'-3' order, a eukaryotic leader sequence, a WNV PrM polypeptide, a WNV E polypeptide and a translational stop codon.

In certain embodiments, the leader sequence present in the vector is the Tissue Plasminogen Activator (TPA) leader sequence. In other embodiments, the nucleic acid encoding the WNV polyprotein is operably linked to a eukaryotic promoter, such as a regulatable promoter.

In further embodiments, the invention is directed to a host cell comprising any of the above vectors. The host cell can be, but is not limited to, a mammalian cell, such as a CHO cell or a HEK293 cell. In additional embodiments, the regulatable promoter can be activated in these cells.

In yet another embodiment, the invention is directed to a method for producing an immunogenic WNV PrM/E polypeptide. The method comprises: (a) culturing the population of host cells as described above under conditions that provide for intracellular expression of recombinant PrM/E polypeptide; (b) recovering an insoluble portion from the cells, wherein the insoluble portion contains substantially all of the membrane component of the cells; (c) treating the insoluble portion with a non-ionic detergent, thereby to solubilize the membrane component and release the PrM/E polypeptide; and (d) purifying the released PrM/E polypeptide.

In certain embodiments of the above method, the recovering step comprises the sequential steps of: (i) concentrating the cultured cells; (ii) lysing the cells in a hypotonic buffer to produce a soluble lysate portion ad an insoluble portion; and (ii) collecting the insoluble portion.

In yet further embodiments, the purifying comprises at least one column purification step wherein the column is selected from the group consisting of a lectin affinity column, a hydroxyapatite column and a cation exchange column.

In additional embodiments, the purifying step comprises (i) binding the released PrM/E polypeptide to a lectin affinity column; (ii) eluting the bound polypeptide from the lectin affinity column; (iii) subjecting the eluted polypeptide to a hydroxyapatite column; (iv) recovering the flowthrough fraction containing the PrM/E polypeptide from the hydroxyapatite column; (v) binding the recovered PrM/E polypeptide to a cation exchange column; and (vi) eluting the bound PrM/E polypeptide from the cation exchange column.

In certain embodiments of the above methods the lectin affinity column is a GNA lectin column. Additionally, in any of the above methods, the PrM/E heterodimers can recovered in a complex of about 3 to about 6 heterodimers, such as in a complex of about 4 to about 6 heterodimers.

In yet further embodiments, the invention is directed to an immunogenic composition comprising the complex obtained by the methods above.

In additional embodiments, the invention is directed to a vaccine comprising the any of the immunogenic compositions described above.

In further embodiments, the invention is directed to antibodies specific for any of the above immunogenic compositions, such as but not limited to polyclonal or monoclonal antibodies.

In another embodiment, the invention is directed to a method of treating or preventing WNV infection in a vertebrate subject comprising administering to the subject a therapeutically effective amount of the vaccine described above.

In additional embodiments, the invention is directed to a method of detecting WNV antibodies in a biological sample. The method comprises: (a) reacting the biological sample with any of the above immunogenic compositions under conditions which allow WNV antibodies, when present in the biological sample, to bind to the composition to form an antibody/antigen complex; and (b) detecting the presence or absence of the antibody/antigen complex, thereby detecting the presence or absence of WNV antibodies in the sample.

In yet further embodiments, the invention is directed to an immunodiagnostic test kit for detecting WNV infection. The test kit comprises any of the immunogenic compositions described above and instructions for conducting the immunodiagnostic test.

In another embodiment, the invention is directed to a method of detecting WNV antigens in a biological sample, comprising: (a) reacting the biological sample with the antibodies above, under conditions which allow WNV antigens, when present in the biological sample, to bind to the antibodies to form an antibody/antigen complex; and (b) detecting the presence or absence of the antibody/antigen complex, thereby detecting the presence or absence of WNV antigens in said sample.

In further embodiments, the invention is directed to an immunodiagnostic test kit for detecting WNV infection. The test kit comprises antibodies as described above and instructions for conducting the immunodiagnostic test.

In additional embodiment, the invention is directed to a solid support, such as but not limited to a nitrocellulose strip. The solid support comprises the immunogenic composition comprising at least one WNV PrM/E heterodimer as described above. In certain embodiments, the solid support also comprises at least one anti-human immunoglobulin antibody, wherein the PrM/E heterodimer and the anti-human immunoglobulin antibody are immobilized in discrete positions on the solid support. For example, the at least one anti-human immunoglobulin antibody can be selected from the group consisting of an anti-human IgM antibody, an anti-human IgG antibody and an anti-human IgA antibody. Moreover, the solid support can also comprise at least two internal controls, wherein one of the controls defines the lower detection limit for a positive result in an immunoassay using the solid support and the other control defines a highly positive result in an immunoassay using the solid support. In this embodiment, the at least two internal controls can comprise first and second monoclonal antibodies directed against a WNV envelope antigen, such as monoclonal antibodies.

In still further embodiment, the invention is directed to a nitrocellulose support comprising: (a) the immunogenic composition comprising at least one WNV PrM/E heterodimer as described above; (b) at least one anti-human IgM antibody; (c) at least one anti-human IgG antibody; (d) at least one anti-human IgA antibody; and (e) at least two internal controls, wherein one of the controls is an anti-WNV envelope monoclonal antibody that defines a lower detection limit for a positive result in a strip immunoblot assay using the nitrocellulose support, and the other control is anti-WNV envelope monoclonal antibody that defines a highly positive result in a strip immunoblot assay using the nitrocellulose support; wherein the immunogenic composition, the anti-human IgM antibody, the anti-human IgG antibody, the anti-human IgA antibody, and the at least two internal controls are each immobilized in discrete positions on said nitrocellulose support.

In another embodiment, the invention is directed to a method of detecting the presence of WNV antibodies in a biological sample. The method comprises: (a) providing a biological sample; (b) providing any of the solid supports described above; (c) contacting said biological sample with the solid support, under conditions which allow WNV antibodies, if present in the biological sample, to bind with at least the WNV PrM/E heterodimer to form an antibody/antigen complex; and (d) detecting the presence of the antibody/antigen complex, thereby detecting the presence of WNV antibodies in the biological sample. In certain embodiments, the above method further comprises: (e) removing unbound WNV antibodies; (f) providing one or more moieties capable of associating with said antibody/antigen complex; and (g) detecting the presence of said one or more moieties, thereby detecting the presence of WNV antibodies in the biological sample.

In certain embodiments of the above method, the one or more moieties comprises a detectably labeled WNV PrM/E heterodimer. The detectable label can be, but is not limited to, an enzyme. Moreover, the biological sample can be from a human blood sample.

In yet a further embodiment, the invention is directed to a method of detecting WNV antibodies in a biological sample. The method comprises: (a) providing a biological sample from a human blood sample; (b) providing a nitrocellulose support as described above; (c) contacting the biological sample with the nitrocellulose support, under conditions which allow WNV antibodies, if present in the biological sample, to bind with at least the WNV PrM/E heterodimer to form an antibody/antigen complex; (d) removing unbound antibodies; (e) providing a detectably labeled WNV PrM/E heterodimer, under conditions which allow binding to any bound WNV antibodies; (f) removing unbound detectably labeled WNV PrM/E heterodimer; and (g) detecting the presence of said bound detectable label, thereby detecting the presence of WNV antibodies in the biological sample.

In a further embodiment, the invention is directed to a method of identifying the immunoglobulin class of a WNV antibody present in a biological sample containing WNV. The method comprises: (a) providing a biological sample derived from a human blood sample; (b) providing a nitrocellulose support as described above; (c) contacting the biological sample with the nitrocellulose support, under conditions which (i) allow WNV antibodies in the biological sample to bind with the immobilized WNV PrM/E heterodimer to form an antibody/antigen complex, and (ii) allow WNV antibodies present in the biological sample to bind to at least one of the immobilized anti-IgG, anti-IgM and/or anti-IgA immunoglobulins; (d) removing unbound WNV antibodies; (e) providing a detectably labeled WNV PrM/E heterodimer under conditions that allow binding of the labeled WNV PrM/E heterodimer to any bound WNV antibodies; (f) removing any unbound labeled heterodimer; and (g) detecting the presence of said detectable label, thereby identifying the immunoglobulin class of WNV antibody present in the biological sample.

In another embodiment, the invention is directed to an immunodiagnostic test kit for detecting WNV. The test kit comprises: (a) any of the solid supports described above, such as a nitrocellulose support as described above; and (b) instructions for conducting the immunodiagnostic test.

In a further embodiment, the invention is directed to a method of preparing a blood supply comprising whole blood, platelets, plasma or serum, substantially free of WNV. The method comprises: (a) screening aliquots of whole blood, platelets, plasma or serum from collected blood samples by any of the detection methods described above; (b) eliminating any samples in which WNV antigen or WNV antibody is detected; and (c) combining samples in which neither WNV antigen nor WNV antibody is detected to provide a blood supply substantially free of WNV.

In an additional embodiment, the invention is directed to a method of detecting the presence of WNV antibodies in a human biological sample. The method comprises: (a) providing a human biological sample; (b) providing a solid support comprising anti-human immunoglobulin antibody; (c) contacting the biological sample with the solid support, under conditions which allow WNV antibodies, if present in the biological sample, to bind with the anti-human immunoglobulin antibody to form an antibody/antibody complex; (d) removing any unbound WNV antibodies; (e) providing a detectably labeled immunogenic composition as described above, under conditions which allow binding to any bound WNV antibodies; and (f) detecting the presence of the bound labeled immunogenic composition, thereby detecting the presence of WNV antibodies in the biological sample.

In further embodiments, the invention is directed to an improved WNV capture IgM-ELISA, or a WNV indirect IgG-ELISA, the improvement comprising providing any of the immunogenic compositions described above as the antigen.

These and other embodiments of the subject invention will readily occur to those of skill in the art in view of the disclosure herein.

BRIEF DESCRIPTION OF THE FIGURES

FIG. 1 is a diagrammatic representation of the WNV genome, depicting the various regions of the WNV polyprotein.

FIGS. 2A-2N (SEQ ID NOS:1 and 2) show the nucleotide sequence and corresponding amino acid sequence for a representative WNV polyprotein. The various regions of the polyprotein are labeled.

FIGS. 3A-3B show a comparison between the nucleotide sequence of the PrM/E region of WNV strain NY99 (SEQ ID NO:3), top strand, versus a synthetic construct (SEQ ID NO:4), bottom strand, for use with the present invention. The sequences display approximately 98% sequence identity to each other.

FIGS. 4A-4C (SEQ ID NOS:5 and 6) show the nucleotide sequence and corresponding amino acid sequence of the WNV PrM/E synthetic construct.

FIG. 5 shows the reactivity of HEK293 cell-produced WNV PrM/E antigen with various commercial monoclonal antibodies.

FIG. 8 shows a representative interpretation of the strip shown in FIG. 7, with scoring ranging from +/- to 4+.

FIG. 12 shows the amino acid sequence (SEQ ID NO:7) and the DNA sequence (SEQ ID NO:12) of the TPA leader used to express WNV proteins of the invention.

FIG. 13 (SEQ ID NOS:8 and 9) show the nucleotide sequence and corresponding amino acid sequence of a representative WNV PrM region.

FIGS. 14A-14C (SEQ ID NOS:10 and 11) show the nucleotide sequence and the corresponding amino acid sequence of a representative WNV E region.

DETAILED DESCRIPTION OF THE INVENTION

Figure 6:
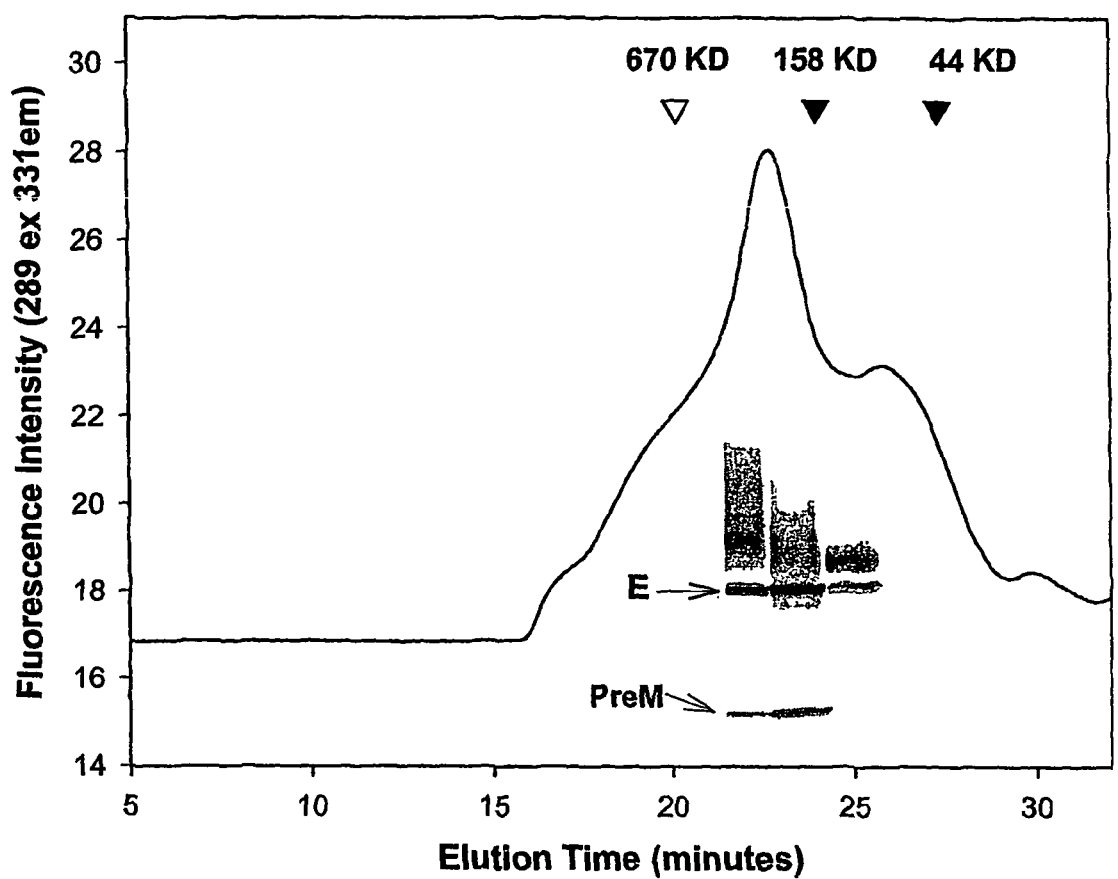
FIG. 6 shows the results of size exclusion chromatography of 293 cell-produced WNV PrM/E antigen.
Figure 7:
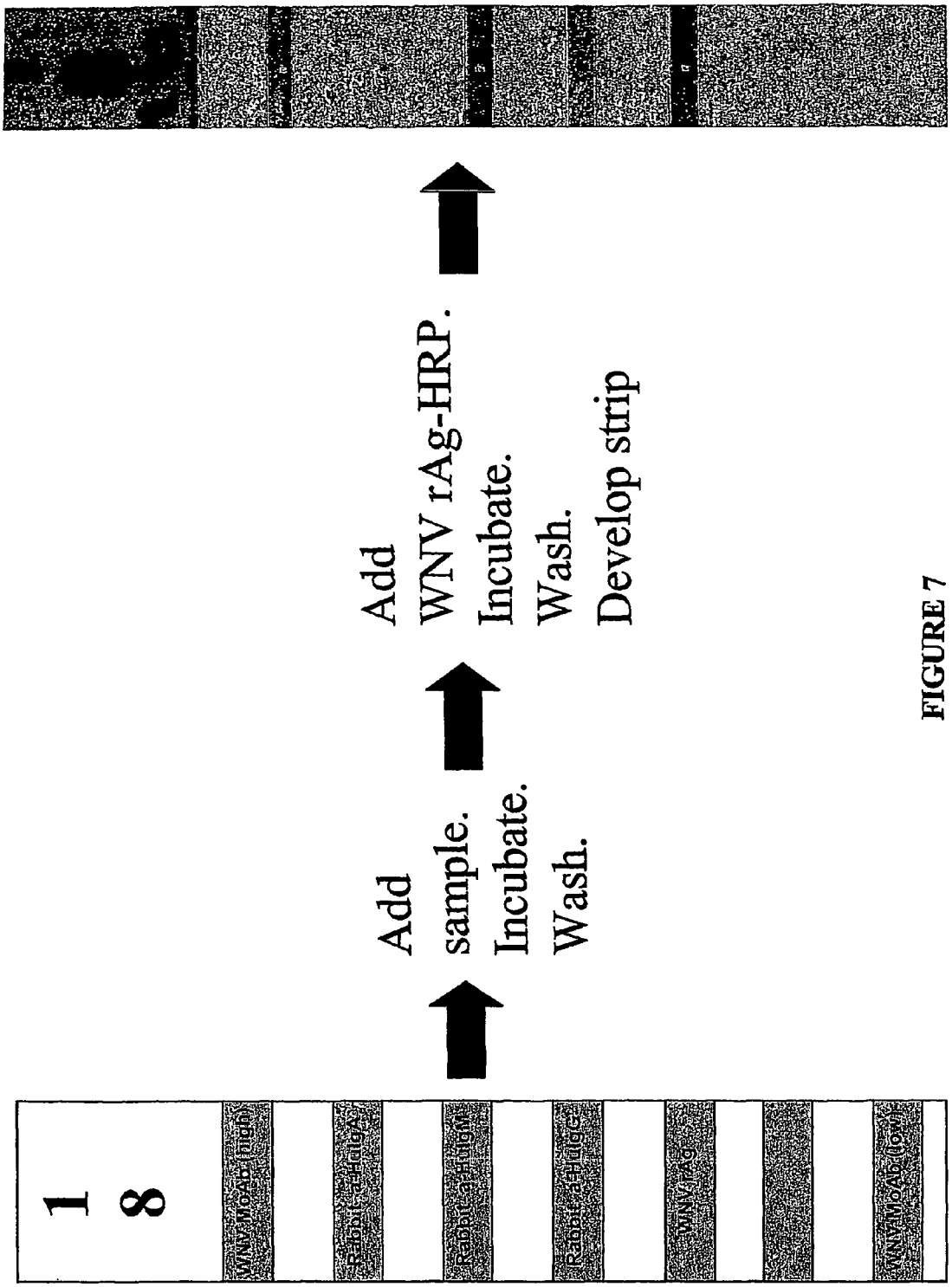
FIG. 7 depicts a representative test strip for use in a strip immunoblot assay (SIA) as described in the examples and representative results after use in a strip immunoblot assay. Two levels of a WNV monoclonal antibody directed against the WNV envelope are used as internal controls (specified as high and low on the figure). Also present are anti-human IgA antibody, anti-human IgG antibody and anti-human IgM antibody, as well as a PrM/E antigen (shown as WNV rAg) in the figure. The reactivity of the individual antigen band with antibody from the sample is determined by comparing the intensity of each band to the low (1+) and high (3+) internal strip controls as described in the examples.

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology*, 2nd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entireties.

The following amino acid abbreviations are used throughout the text:
Alanine: Ala (A)
Asparagine: Asn (N)
Cysteine: Cys (C)
Glutamic acid: Glu (E)
Histidine: His (H)
Leucine: Leu (L)
Methionine: Met (M)
Proline: Pro (P)
Threonine: Thr (T)
Tyrosine: Tyr (Y)
Arginine: Arg (R)
Aspartic acid: Asp (D)
Glutamine: Gin (Q)
Glycine: Gly (G)
Isoleucine: He (I)
Lysine: Lys (K)
Phenylalanine: Phc (F)
Serine: Ser (S)
Tryptophan: Trp (W)
Valine: Val (V)

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an envelope polypeptide" includes a mixture of two or more such polypeptides, and the like.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof can be encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

A WNV polypeptide is a polypeptide, as defined above, derived from the naturally produced WNV polyprotein. The term WNV polypeptide includes fusion polypeptides in which one or more of the fused polypeptides are derived from the WNV polyprotein. The polypeptide need not be physically derived from WNV, but may be synthetically or recombinantly produced. Moreover, the polypeptide may be derived from any of the various WNV strains and isolates. A number of conserved and variable regions are known between the various isolates and, in general, the amino acid sequences of epitopes derived from these regions will have a high degree of sequence homology, e.g., amino acid sequence homology of more than 30%, generally more than 40%-50%, when the two sequences are aligned. Thus, for example, the term "WNV envelope polypeptide" (also referred to herein as "WNV E polypeptide" refers to the native full-length envelope polypeptide from any of the various WNV isolates or strains, or analogs, muteins and immunogenic fragments of the polypeptide, as defined further below. Similarly, the term "WNV PrM polypeptide" refers to the native full-length PrM sequence which includes the membrane precursor. The sequence can be from any of the various WNV isolates or strains. The term can also include analogs, muteins and immunogenic fragments of the native sequence. These regions of the WNV polyprotein are discussed in more detail below. Sequences for the WNV genome, including the regions encoding the various polypeptides found in the polyprotein of WNV in a number of WNV isolates are known. One representative sequence for the WNV polyprotein and DNA encoding the polyprotein is shown in FIGS. 2A-2N herein. See, also, NCBI accession numbers NC001563; AF404757; AF404756; AF404755; AF404754; AF404753; AF481864; M12294; AF196835; AF260969; AF260968; AF260967; AF206518; AF202541; AF196835; Brinton, M. A., *Ann. Rev. Micorbiol.* (2002) 56:371-402; Lanciotti et al., *Science* (1999) 286:2333-2337; and U.S. Patent Publication No. 2002/0164349, all of which are incorporated herein by reference in their entireties. A representative sequence for a WNV PrM/E polypeptide as it exists prior to proteolytic processing is shown in FIGS. 4A-4C herein. This sequence corresponds to amino acid positions 124-791 of FIGS. 2A-2N.

A polypeptide "derived from" a WNV polyprotein intends a polypeptide which comprises a sequence of one or more regions or portions of regions of the reference WNV polyprotein. Typically, the polypeptide is composed of regions or portions of regions that include epitopes, and will generally have an amino acid sequence substantially homologous to the reference polypeptide, as defined below. Thus, the term "derived from" is used to identify the original source of a molecule but is not meant to limit the method by which the molecule is made which can be, for example, by chemical synthesis or recombinant means.

By "WNV PrM/E polypeptide" is meant an association of a WNV PrM polypeptide with a WNV E polypeptide. The mode of association of the PrM polypeptide with the E polypeptide can be, for example, by covalent or non-covalent interaction, such as by hydrophobic interaction. For example, a PrM/E polypeptide can form upon cleavage of a protein including the PrM and E regions or simply by mixing PrM and E proteins together that have been produced separately, e.g., by coexpression of separate DNA constructs encoding the proteins. In a preferred embodiment, the PrM/E polypeptide is formed upon intracellular cleavage of a protein including the PrM and E regions.

In a preferred embodiment, the invention provides a recombinant PrM/E "heterodimer complex" wherein more than one PrM/E heterodimer is in association with each other, wherein the ratio of PrM to E in each heterodimer complex is approximately 1:1). Such heterodimers and heterodimer complexes are discussed more fully below. The formation of a PrM/E heterodimer or heterodimer complexes are readily determined using standard protein detection techniques such as polyacrylamide gel electrophoresis and immunological techniques such as immunoprecipitation.

A composition "substantially free of WNV M polypeptide" is a composition that has less than 15% by weight of free M polypeptide (i.e., M polypeptide not in the PrM form), preferably less than 10% by weight of free M, even more preferably less than 5% by weight of free M, such as less than 4%, 3%, 2%, 1%, 0.5%, etc., by weight of free M, or any % within the stated ranges.

The terms "analog" and "mutein" refer to biologically active derivatives of the reference molecule, such as a WNV envelope, or fragments of such derivatives, that retain desired activity, such as immunoreactivity in assays described herein. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity and which are "substantially homologous" to the reference molecule as defined below. The term "mutein" refers to peptides having one or more peptide mimics ("peptoids"), such as those described in International Publication No. WO 91/04282. Preferably, the analog or mutein has at least the same immunoreactivity as the native molecule. Methods for making polypeptide analogs and muteins are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25, 50 or 75 conservative or non-conservative amino acid substitutions, or any integer between 5-75, so long as the desired function of the molecule remains intact. One of skill in the art can readily determine regions of the molecule of interest that can tolerate change by reference to Hopp/Woods and Kyte-Doolittle plots, well known in the art.

By "fragment" is intended a polypeptide consisting of only a part of the intact full-length polypeptide sequence and structure. The fragment can include a C-terminal deletion an N-terminal deletion, and/or an internal deletion of the native polypeptide. An "immunogenic fragment" of a particular WNV protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains the ability to elicit an immunological response as defined herein. Particular examples of WNV fragments for use with the present invention are described further below.

The term "epitope" as used herein refers to a sequence of at least about 3 to 5, preferably about 5 to 10 or 15, and not more than about 500 amino acids (or any integer there between), which define a sequence that by itself or as part of a larger sequence, elicits an immunological response in the subject to which it is administered. Often, an epitope will bind to an antibody generated in response to such sequence. There is no critical upper limit to the length of the fragment, which may comprise nearly the full-length of the protein sequence, or even a fusion protein comprising two or more epitopes from the WNV polyprotein. An epitope for use in the subject invention is not limited to a polypeptide having the exact sequence of the portion of the parent protein from which it is derived. Indeed, viral genomes are in a state of constant flux and contain several variable domains which exhibit relatively high degrees of variability between isolates. Thus the term "epitope" encompasses sequences identical to the native sequence, as well as modifications to the native sequence, such as deletions, additions and substitutions (generally conservative in nature).

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1985) *Proc. Natl. Acad. Sci. USA* 82:178-182; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824-3828 for determining antigenicity profiles, and the Kyte-Doolittle technique, Kyte et al., *J. Mol. Biol.* (1982) 157:105-132 for hydropathy plots.

A "WNV antigen" is a molecule that is capable of binding to a WNV-specific antibody.

An "immunogenic polypeptide" or "immunogenic fragment" is a polypeptide or a polypeptide fragment that can elicit an immunological response.

An "immunogenic composition" is a composition that comprises at least one immunogenic polypeptide. For example, for purposes of the present invention, an immunogenic composition can include a WNV PrM polypeptide and a WNV E polypeptide in the form of a heterodimer or a complex of a plurality of such heterodimers. In a particularly preferred embodiment, the immunogenic composition of the invention comprises a heterodimer complex of about 4 to 6 PrM/E heterodimers. In another particularly preferred embodiment, the immunogenic composition of the invention comprises a heterodimer complex of about 3 to 5 PrM/E heterodimers A "vaccine composition" is a composition that comprises at least one immunogenic composition and that prevents infection or reinfection (prophylaxis), or reduces or eliminates symptoms of the disease of interest (therapy).

By "an immunogenic heterodimer complex" of PrM/E heterodimers is meant a group of heterodimers (that is, more than one heterodimer) in association with each other, wherein each heterodimer consists of a PrM polypeptide and an E polypeptide. Such complexes may therefore include from 2 up to 50 such heterodimers, preferably 2 to 20 heterodimers, such as 3 to 6, e.g., 3 to 5, 4 to 6, etc. heterodimers, or any number within the stated ranges. Such heterodimers and complexes of heterodimers are discussed more fully below.

An "immunological response" to a WNV immunogen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376.

Thus, an immunological response as used herein may be one which stimulates the production of CTLs, and/or the production or activation of helper T-cells. The antigen of interest may also elicit an antibody-mediated immune response, including, or example, neutralization of binding (NOB) antibodies. The presence of an NOB antibody response is readily determined by the techniques described in, e.g., Rosa et al., *Proc. Natl. Acad. Sci. USA* (1996) 93:1759. Hence, an immunological response may include one or more of the following effects: the production of antibodies by B-cells; and/or the activation of suppressor T-cells and/or γδT-cells directed specifically to an antigen or antigens present in the composition or vaccine of interest. These responses may serve to neutralize infectivity, and/or mediate antibody-complement, or antibody dependent cell cytotoxicity (ADCC) to provide protection or alleviation of symptoms to an immunized host. Such responses can be determined using standard immunoassays and neutralization assays, well known in the art.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

By "equivalent antigenic determinant" is meant an antigenic determinant from different isolates or strains of WNV which antigenic determinants are not necessarily identical due to sequence variation, but which occur in equivalent positions in the WNV sequence in question. In general the amino acid sequences of equivalent antigenic determinants will have a high degree of sequence homology, e.g., amino acid sequence homology of more than 30%, usually more than 40%, such as more than 60%, and even more than 80-90% homology, when the two sequences are aligned.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, counting the exact number of matches between the two aligned sequences, dividing by the length of the reference sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide"."oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnulcleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide, "; "nucleic acid" and "nucleic acid molecule," and these terms will be used interchangeably. Thus, these terms include, for example, 3'-deoxy-2',5'-DNA, oligodeoxyribonucleotide N3' P5'phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

A "WNV polynucleotide" is a polynucleotide that encodes a WNV polypeptide, as defined above.

A "coding sequence" or a sequence which "encodes" a selected polypeptide, is a nucleic acid molecule which is transcribed (in the case of DNA) and translated (in the case of mRNA) into the polypeptide in vitro or in vivo when placed under the control of appropriate regulatory sequences. The typical boundaries of the coding sequence are determined by a start codon at the 5'(amino) terminus and a translation stop codon at the 3'(carboxy) terminus. In the case of a sequence encoding a polyprotein, as is encoded by the WNV genome, the coding sequence is a nucleic acid sequence that is translated into the amino acid sequence of the processed polypeptide and does not necessarily contain a conventional start codon or translational stop codon; for example, a "coding sequence" for the PrM polypeptide is a nucleic acid sequence that encodes the contiguous amino acids from amino acid 124 through amino acid 290 of the sequence shown in FIG. 2A-2N. A transcription termination sequence may be located 3' to the coding sequence.

"Operably linked" refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered "operably linked" to the coding sequence.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A WNV polypeptide is produced "intracellularly" when it is found within the cell, either associated with components of the cell, such as in association with the endoplasmic reticulum (ER) or the Golgi Apparatus, or when it is present in the soluble cellular fraction. A WNV polypeptide is still considered to be produced "intracellularly" even if it is secreted into growth medium so long as sufficient amounts of the polypeptides remain present within the cell such that they can be purified from cell lysates and extracts using techniques described herein.

A "control element" refers to a polynucleotide sequence which aids in the expression of a coding sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for the transcription and translation of a coding sequence in a host cell.

A "eukaryotic leader sequence" is a leader sequence derived from a protein that is naturally produced in a eukaryote, such as, but not limited to, a yeast, fungal, algal, plant and mammalian protein. The term also includes synthetic leader sequences but does not include leaders derived from viruses. Preferably, there are proteolytic processing sites encoded between the leader fragment and the encoded polypeptide of the gene of interest, such as a gene encoding a WNV PrM/E polypeptide, that can be cleaved either in vivo or in vitro. The leader sequence typically encodes a signal peptide comprised of hydrophobic amino acids capable of directing the secretion of the protein under appropriate conditions. Examples of such leaders include, without limitation, those derived from genes encoding tissue plasminogen activator (TPA, see, FIG. 12 for a TPA leader sequence); human α-interferon (Maeda et al., *Nature* (1985) 315:592); human gastrin-releasing peptide, Lebacq-Verheyden et al., *Molec. Cell. Biol.* (1988) 8:3129; human IL-2, Smith et al., *Proc. Nat'l Acad. Sci. USA* (1985) 82:8404; mouse IL-3, (Miyajima et al., *Gene* (1987) 58:273; human glucocerebrosidase, Martin et al., *DNA* (1988) 7:99; leaders derived from genes for secreted yeast proteins, such as the yeast invertase gene (EPO Publication No. 012,873; JPO Publication No. 62,096,086), the α-factor gene (U.S. Pat. No. 4,588,684), truncated α-factor leaders (U.S. Pat. Nos. 4,546,083 and 4,870,008; EPO Publication No. 324,274), hybrid α-factor leaders (PCT Publication No. WO 89/02463); interferon leaders (EPO Publication No. 060,057), and the like.

A "promoter" as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eukaryotic promoters (i.e., those promoters that are capable of functioning in eukaryotic cells and are normally found in association with eukaryotic proteins) will often, but not always, contain "TATA" boxes and "CAT" boxes. Non-limiting examples of eucaryotic promoters include any of the various heat shock protein promoters (see, e.g., Morimoto et. al., eds., *Stress Proteins in Biology and Medicine* (1990) Cold Spring Harbor Press; Hightower, L. E. *Cell* (1991) 66:191-197.; Craig, E. A., and Gross, C. A. (1991) *Trends Bioch. Sci.* 16:135; Dreano et al., *Gene* (1986) 49:1-8; EPO Publication No. 336,523; PCT Publication No. WO 87/00861; EPO Publication No. 118, 393; and PCT Publication No. WO 87/05935); a promoter derived from the murine metallothionein gene; promoters derived from sequences encoding enzymes in the metabolic pathway such as alcohol dehydrogenase (ADH) (EPO Publication No. 284,044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO Publication No. 329,203); a promoter derived from the yeast PHO5 gene encoding acid phosphatase (Myanohara et al., *Proc. Natl. Acad. Sci. USA* (1983) 80:1). Eukaryotic promoters also include viral promoters derived from eukaryotic viruses, e.g., the CMV promoter, SV 40 promoters, adenovirus promoters, alphaviral promoters. A eukaryotic promoter is also intended to encompass synthetic promoters which do not occur in nature, such as but not limited to synthetic hybrid promoters. For example, upstream activating sequences (UAS) of one yeast promoter can be joined with the transcription activation region of another yeast promoter, creating a synthetic hybrid promoter. Non-limiting examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EPO Publication No. 164,556).

A "regulatable" promoter is a promoter that either induces or represses expression of a polynucleotide sequence operably linked to the promoter by e.g., an analyte, cofactor, regulatory protein, temperature, etc. Such promoters are well known in the art. See, e.g., Sambrook, et al., supra.

A control sequence "directs the transcription" of a coding sequence in a cell when RNA polymerase will bind the promoter sequence and transcribe the coding sequence into mRNA, which is then translated into the polypeptide encoded by the coding sequence.

"Expression cassette" or "expression construct" refers to an assembly which is capable of directing the expression of the sequence(s) or gene(s) of interest. The expression cassette includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Transformation," as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

By "nucleic acid immunization" is meant the introduction of a nucleic acid molecule encoding one or more selected immunogens into a host cell, for the in vivo expression of the immunogen. The nucleic acid molecule can be introduced directly into a recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the immunogen encoded by the nucleic acid molecule.

An "antibody" intends a molecule that specifically binds to an epitope of interest present in an antigen. By "specifically binds" is meant that the antibody recognizes and interacts with the epitope in a "lock and key" type of interaction to from a complex between the antigen and antibody, as opposed to non-specific binding that might occur between the antibody and, for instance, the test substrate. Thus, an anti-WNV envelope antibody is a molecule that specifically binds to an epitope of a WNV envelope protein. The epitope can be present in, for example, a larger WNV polypeptide that includes the full-length or a truncated envelope protein, such as in a WNV PrM/E protein as described herein. The term "antibody" as used herein includes antibodies obtained from both polyclonal and monoclonal preparations, as well as, the following: hybrid (chimeric) antibody molecules (see, for example, Winter et al. (1991) *Nature* 349:293-299; and U.S. Pat. No. 4,816,567); F(ab')2 and F(ab) fragments; Fv molecules (non-covalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, for example, Huston et al. (1988) *Proc Natl Acad Sci USA* 85:5879-5883); dimeric and trimeric antibody fragment constructs; minibodies (see, e.g., Pack et al. (1992) *Biochem* 31:1579-1584; Cumber et al. (1992) *J Immunology* 149B:120-126); humanized antibody molecules (see, for example, Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, $F(ab')_2$, Fv, and other fragments, as well as chimeric and humanized homogeneous antibody populations, that exhibit immunological binding properties of the parent monoclonal antibody molecule.

As used herein, a "solid support" refers to a solid surface to which a macromolecule, e.g., protein, polypeptide, peptide, polynucleotide can be attached, such as a magnetic bead, latex bead, microtiter plate well, glass plate, nylon, agarose, polyacrylamide, silica particle, nitrocellulose membrane, and the like.

"Immunologically reactive" means that the antigen in question will react specifically with anti-WNV antibodies present in a biological sample from a WNV-infected individual.

"Immune complex" intends the combination formed when an antibody binds to an epitope on an antigen.

As used herein, a "biological sample" refers to a sample of tissue or fluid isolated from a subject such as, but not limited to, blood, plasma, serum, fecal matter, urine, bone marrow, bile, spinal fluid, lymph fluid, cerebrospinal fluid, samples of the skin, secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. The samples detailed above need not necessarily be in the form obtained directly from the source. For example, the sample can be treated prior to use, such as, for example, by heating, centrifuging, etc. prior to analysis.

As used herein, the terms "label" and "detectable label" refer to a molecule capable of detection, including, but not limited to, radioactive isotopes, fluorescers, semiconductor nanocrystals, chemiluminescers, chromophores, enzymes, enzyme substrates, enzyme cofactors, enzyme inhibitors, dyes, metal ions, metal sols, ligands (e.g., biotin, strepavidin or haptens) and the like. The term "fluorescer" refers to a substance or a portion thereof which is capable of exhibiting fluorescence in the detectable range. Particular examples of labels which may be used under the invention include, but are not limited to, horse radish peroxidase (HRP), fluorescein, FITC, rhodamine, dansyl, umbelliferone, dimethyl acridinium ester (DMAE), Texas red, luminol, NADPH and α-β-galactosidase.

The terms "effective amount" or "pharmaceutically effective amount" of an immunogenic composition, as provided herein, refer to a nontoxic but sufficient amount of the composition to provide the desired response, such as an immunological response, and optionally, a corresponding therapeutic effect. The exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The invention described herein is intended for use in any of the above vertebrate species, since the immune systems of all of these vertebrates operate similarly.

The term "treatment" as used herein refers to either (1) the prevention of infection or reinfection (prophylaxis), or (2) the reduction or elimination of symptoms of the disease of interest (therapy).

2. Modes Of Carrying Out The Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Central to the present invention is the successful recombinant production of immunogenic WNV proteins. In particular, the inventors herein have efficiently produced proteins from numerous regions of the WNV genome, including from regions encoding the capsid, premembrane (including mature membrane) and envelope (see FIG. 1). The WNV proteins, heterodimers of the proteins, immunogenic fragments thereof or fusion proteins including the same, can be provided in immunogenic compositions, such as in subunit vaccine compositions. In addition to use in vaccine compositions, the proteins or antibodies thereto can be used as diagnostic reagents to detect the presence of infection in a vertebrate subject, or to screen blood supplies for the presence of WNV-infected blood.

In order to further an understanding of the invention, a more detailed discussion is provided below regarding WNV, various WNV polypeptide immunogens for use in the subject compositions and methods, as well as production of the proteins, antibodies thereto and methods of using the proteins and antibodies.

WNV Polypeptides and Polynucleotides

As explained above, the genomes of WNV isolates contain a single open reading frame of approximately 10,000 nucleotides, which is transcribed into a polyprotein. The various regions of the polyprotein are shown in FIG. 1 and Table 1. The polyprotein is proteolytically processed by the viral serine protease NS2B-NS3 and various cellular proteases into 10 mature viral proteins, in the order of $NH_2$—C—PrM-E-NS1-NS2A-NS2B-NS3-NS4A-NS4B-NS5-COOH. The three structural proteins, capsid (C), membrane (PrM), and envelope (E), are encoded within the 5' portion of the ORF, while the seven nonstructural proteins, NS1, NS2A, NS2B, NS3, NS4A, NS4B and NS5, are encoded within the 3' portion. The capsid polypeptide occurs at positions 1-123, numbered relative to WNV strain WN-NY99 (see, Lanciotti et al., *Science* (1999) 286:2333-2337 and NCBI Accession No. AF196835, for the WN-NY99 genomic sequence). The membrane precursor polypeptide, PrM, is found at positions 124-290. The mature membrane protein (M) is found at positions 216-290. The envelope polypeptide, E, occurs at about positions 291-791. The NS1 domain is found at about positions 792-1143. NS2A is found at about positions 1144-1374 of the polyprotein. NS2B occurs at 1375-1505. NS3 is found at about positions 1506-2124, NS4A at positions 2125-2273 and NS4B at positions 2274-2528. NS5 occurs at positions 2529-3433.

TABLE 1

| Domain | Approximate Boundaries* |
|---|---|
| C (capsid) | 1-123 |
| PrM | 124-290 |
| E | 291-791 |
| NS1 | 792-1143 |
| NS2A | 1144-1374 |

TABLE 1-continued

| Domain | Approximate Boundaries* |
|---|---|
| NS2B | 1375-1505 |
| NS3 | 1506-2124 |
| NS4A | 2125-2273 |
| NS4B | 2274-2528 |
| NS5 | 2529-3433 |

*Numbered relative to WN-NY99 (see, Lanciotti et al., Science (1999) 286: 2333-2337 and NCBI Accession No. AF196835).

Nucleic acid and amino acid sequences of a number of WNV strains and isolates, including the nucleic acid and amino acid sequences of the various regions described above, have been determined. For example, isolate WN-NY99 is described in Lanciotti et al., Science (1999) 286:2333-2337 and NCBI Accession No. AF196835. See, also, NCBI accession numbers NC001563; AF404757; AF404756; AF404755; AF404754; AF404753; AF481864; M12294; AF196835; AF260969; AF260968; AF260967; AF206518; AF202541; AF196835; Brinton, M. A., Ann. Rev. Micorbiol. (2002) 56:371-402; and U.S. Patent Publication No. 2002/0164349. FIGS. 2A-2N depict a nucleotide and amino acid sequence of a representative WNV polyprotein. FIGS. 3A-3B show a modified nucleotide sequence coding for a WNV PrM/E protein described more fully below. As seen in FIGS. 3A-3B, this sequence includes a number of modifications to nucleotides to either create or destroy restriction enzyme cleavage sites.

Thus, immunogens for use in subunit vaccines and diagnostics include those derived from one or more of the above regions from any strain or isolate. Either the full-length proteins, fragments thereof containing epitopes of the full-length proteins, as well as fusions of the various regions or fragments thereof, will find use in the subject compositions and methods. Thus, for example, the WNV immunogens can be derived from the envelope region of any of these WNV isolates. This region occurs at amino acid positions 291-791 of the WNV polyprotein, numbered relative to WN-NY99 (See, FIGS. 2A-2N). Immunogenic fragments of the envelope which comprise epitopes may be used in the subject methods. For example, fragments of the envelope polypeptide can comprise from about 5 contiguous amino acids to nearly the full-length of the molecule, such as 6, 10, 25, 50, 75, 100, 200, 250, 300, 350, 400, 450 or more contiguous amino acids of an envelope polypeptide, or any integer between the stated numbers.

Moreover, the envelope polypeptide for use herein may lack all or a portion of the transmembrane binding domain found in the C-terminus of the envelope at about positions 742-791. Thus, the present invention contemplates the use of envelope polypeptides which retain the transmembrane binding domain, as well as polypeptides which lack all or a portion of the transmembrane binding domain, including envelope polypeptides terminating at about amino acid 790 and lower, such as terminating at amino acid 775 or lower, such as but not limited to envelope proteins terminating at, for example, amino acid 790 . . . 775 . . . 760 . . . 750 . . . 745, etc. with the understanding that truncations within these stated boundaries are specifically contemplated by the inventors herein.

Furthermore, the C-terminal truncation can extend beyond the transmembrane spanning domain towards the N-terminus. Thus, for example, truncations occurring at positions lower than, e.g., 742, are also encompassed by the present invention. All that is necessary is that the truncated polypeptides remain functional for their intended purpose. Thus, representative C-terminally truncated envelope polypeptides will have a C-terminus at an amino acid position found between amino acid 300 and 790, inclusive, numbered relative to the WN-NY99 polyprotein and FIGS. 2A-2N, such as between amino acid 350 . . . 400 . . . 450 . . . 500 . . . 550 . . . 600 . . . 650 . . . 700 . . . 750 . . . 790, inclusive, or any integer between these stated ranges, numbered relative to the WN-NY99 polyprotein and FIGS. 2A-2N herein.

Additionally, epitopes from the capsid, membrane and non-structural regions will also find use herein For example, epitopes from the precursor membrane protein, found at positions 124-290, or the mature membrane protein, found at positions 216-290, are useful herein. Thus, the membrane protein can include all or a portion of the sequence corresponding to positions 124-215 of the precursor, in addition to one or more epitopes or even the full-length sequence of amino acids corresponding to the sequence of amino acids occurring at positions 216-290, numbered relative to WN-NY99.

Fusion molecules including more than one epitope from more than one region of the WNV polyprotein will also find use with the present invention. The polypeptides derived from the WNV polyprotein need not be organized in the same order as found in the WNV polyprotein. Thus, for example, a capsid polypeptide can be fused to the C-terminus of a membrane polypeptide, etc. One convenient immunogen for use in compositions and methods is a fusion between a membrane polypeptide (with or without the precursor sequence) with an envelope polypeptide, including truncated envelope proteins and fragments as described above. The membrane polypeptide can be fused to either the N- or C-terminus of the envelope polypeptide. Such fusions can also include, for example, sequences upstream of the membrane precursor, such as sequences from the capsid region. For example, 1-10 or more amino acids of the capsid region up to the full-length sequence can be used in the subject fusions. Thus, for example, fusions can include a portion of the capsid beginning at, e.g., amino acid 80 . . . 90, 91, 92, 93, 94, 95 . . . 100, 101, 102, 103 . . . 110 . . . 115 . . . 122, 123, etc. fused to the full-length precursor membrane, the mature membrane polypeptide, or portions thereof, and the full-length envelope, or fragments thereof as described above.

Representative fusion proteins are described in the examples and include, for example, proteins having amino acids 103-791 of FIGS. 2A-2N and amino acids 94-791 of FIGS. 2A-2N. Particularly preferred is the WNV PrM/E fusion protein depicted in FIGS. 4A-4C, or an immunogenic polypeptide with a contiguous sequence of amino acids with at least 75% sequence identity to this sequence, such as displaying at least about 80-90% or more sequence identity thereto, including any percent identity within these ranges, such as 81, 82, 83, 84, 85, 86, 87, 88, 89, 90, 91, 92, 93, 94, 95, 96, 97, 98, 99% sequence identity thereto. As explained above, the sequence depicted in FIGS. 4A-4C corresponds to amino acid positions 124-791 of FIGS. 2A-2N.

Particularly useful is a heterodimeric form of WNV PrM/E. Such heterodimers are produced by intracellular expression of, for example, a polynucleotide encoding a WNV PrM/E fusion protein as described above. When produced intracellularly, the PrM/E fusion protein is further proteolytically processed such that the PrM polypeptide is cleaved away from the E polypeptide. The two polypeptides then spontaneously form heterodimers that include the PrM polypeptide and the E polypeptide in a ratio of approximately 1:1. Moreover, in the heterodimeric form isolated in the present invention the PrM has not been further processed. Thus, the mature M protein is virtually absent from the preparation.

This form of WNV PrM/E differs significantly from the secreted product, such as described in Davis et al., *J. Virol.* (2001) 75:4040-4047. First, the product of the present invention is not isolated as a viral-like particle (VLP) as in Davis et al. but, as described above, as a heterodimer or combination of heterodimer. Additionally, when produced intracellularly, the resulting product substantially lacks free WNV M polypeptide. Thus, the M polypeptide is almost exclusively present in the precursor form and virtually no free M is present. In the VLP form, PrM is further processed to produce free M. Additionally, the heterodimers of the present invention tend to aggregate to form a complex of heterodimers (i.e., more than one heterodimer in association with each other). Such complexes may include from 2 up to 50 such heterodimers, preferably 2 to 20 heterodimers, or any number of heterodimers within these ranges. Typically, the complexes of the present invention have molecular masses of approximately 400 kDa and include 4 to 6 heterodimers. However, depending on the conditions used to isolate the heterodimers, complexes with 2 to 4, 3 to 5, 5 to 7, etc. heterodimers are formed.

The heterodimers and complexes of the present invention are not associated with any viral nucleic acid or other viral components from WNV and thus are distinguished from heterodimers previously described that were isolated from cell-associated WNV particles (Wengler, et al. 1989 J. Virol. 63: 2521).

Moreover, when produced intracellularly, the compositions of the present invention generally include at least 80% of the PrM and E polypeptides in a heterodimeric form, preferably at least 85% to 90% of the PrM and E polypeptides are in a heterodimeric form, and even more preferably at least 95%, such as at least 96%, 97%, 98%, 99%, etc., of the PrM and E polypeptides are in a heterodimeric form.

One representative heterodimer includes a PrM polypeptide with the sequence of amino acids shown at positions 1-167 of FIG. 13 (124-290 of FIG. 2) and an E polypeptide with the sequence of amino acids shown at positions 1-501 of FIG. 14 (291-791 of FIG. 2). These polypeptides are merely illustrative and the heterodimers may take many forms, depending on the PrM and E polypeptides encoded by the polynucleotide used to produce the proteins.

Additionally, epitopes from the NS1, NS2A, NS2B, NS3, NS4A, NS4B, and/or NS5 regions, as well as the full-length sequences, can be used with the subject invention.

It should be noted that for convenience the various regions of the WNV genome have been specified herein with reference to WN-NY99 and FIGS. 2A-2N. However, the polynucleotides and polypeptides for use with the present invention are not limited to those derived from the WN-NY99 sequence. Any strain or isolate of WNV can serve as the basis for providing immunogenic sequences for use with the invention. In this regard, the corresponding regions in another WNV isolate can be readily determined by aligning sequences from the two isolates in a manner that brings the sequences into maximum alignment. Moreover, the sequences used can represent either the native sequence, with or without an N-terminal Met, as well as an active analog of the reference sequence, with or without an N-terminal Met, such as a sequence substantially homologous to the reference sequence, so long as the molecule maintains immunogenicity as defined above.

In one aspect, the present invention includes a recombinant polynucleotide vector comprising a nucleic acid encoding a WNV polyprotein, wherein said nucleic acid encodes, in 5'-3' order, a eukaryotic leader sequence, a WNV PrM polypeptide, a WNV E polypeptide and a translational stop codon.

The eukaryotic leader sequence is preferably the leader sequence (signal peptide) from human tissue plasminogen activator (TPA). In a preferred embodiment, the recombinant vector also includes a eukaryotic promoter that controls expression of the encoded WNV polyprotein. The eukaryotic promoter is preferably a CMV promoter. The vector may additionally contain a polyA addition site.

Polynucleotides and polypeptides for use with the present invention can be obtained using standard techniques. For example, polynucleotides encoding the various WNV polypeptides can be isolated from a genomic library derived from nucleic acid sequences present in, for example, the plasma, serum, or tissue homogenate of a WNV infected individual or can be synthesized in the laboratory, for example, using an automatic synthesizer. An amplification method such as PCR can be used to amplify polynucleotides from either WNV genomic RNA or cDNA encoding therefor.

Polynucleotides can comprise coding sequences for these polypeptides which occur naturally or can include artificial sequences which do not occur in nature. These polynucleotides can be ligated to form a coding sequence for a fusion protein, if desired, using standard molecular biology techniques.

Once coding sequences have been prepared or isolated, such sequences can be cloned into any suitable vector or replicon. Numerous cloning vectors are known to those of skill in the art, and the selection of an appropriate cloning vector is a matter of choice. Suitable vectors include, but are not limited to, plasmids, phages, transposons, cosmids, chromosomes or viruses which are capable of replication when associated with the proper control elements.

The coding sequence is then placed under the control of suitable control elements, depending on the system to be used for expression. Thus, the coding sequence can be placed under the control of a promoter, ribosome binding site (for bacterial expression) and, optionally, an operator, so that the DNA sequence of interest is transcribed into RNA by a suitable transformant. The coding sequence may or may not contain a signal peptide or leader sequence which can later be removed by the host in post-translational processing. See, e.g., U.S. Pat. Nos. 4,431,739; 4,425,437; 4,338,397.

In addition to control sequences, it may be desirable to add regulatory sequences which allow for regulation of the expression of the sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector. For example, enhancer elements may be used herein to increase expression levels of the constructs. Examples include the SV40 early gene enhancer (Dijkema et al. (1985) *EMBO J.* 4:761), the enhancer/promoter derived from the long terminal repeat (LTR) of the Rous Sarcoma Virus (Gorman et al. (1982) *Proc. Natl. Acad. Sci. USA* 79:6777) and elements derived from human CMV (Boshart et al. (1985) *Cell* 41:521), such as elements included in the CMV intron A sequence (U.S. Pat. No. 5,688,688). The expression cassette may further include an origin of replication for autonomous replication in a suitable host cell, one or more selectable markers, one or more restriction sites, a potential for high copy number and a strong promoter.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the molecule of interest may be desirable to achieve this end. For example, in some cases it may be necessary to modify the sequence so that it can be attached to the control sequences in the appropriate orientation; i.e., to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site.

As explained above, it may also be desirable to produce mutants or analogs of the polypeptide of interest. Mutants or analogs of WNV polynucleotides and polypeptides for use in the subject compositions may be prepared by the deletion of a portion of the sequence encoding the molecule of interest, by insertion of a sequence, and/or by substitution of one or more nucleotides within the sequence. Techniques for modifying nucleotide sequences, such as site-directed mutagenesis, and the like, are well known to those skilled in the art. See, e.g., Sambrook et al., supra; Kunkel, T. A. (1985) *Proc. Natl. Acad. Sci. USA* (1985) 82:448; Geisselsoder et al. (1987) *BioTechniques* 5:786; Zoller and Smith (1983) *Methods Enzymol.* 100:468; Dalbie-McFarland et al. (1982) *Proc. Natl. Acad. Sci USA* 79:6409.

The molecules can be expressed in a wide variety of systems, including insect, mammalian, bacterial, viral and yeast expression systems, all well known in the art. For example, insect cell expression systems, such as baculovirus systems, are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described in, e.g., Sambrook et al., supra. Yeast expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human embryonic kidney cells (e.g., HEK293), human hepatocellular carcinoma cells (e.g., Hep G2), Madin-Darby bovine kidney ("MDBK") cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Preferably, the hosts used for the production of the recombinant WNV polypeptides of the present invention are mammalian cell lines; more preferred are Chinese hamster ovary (CHO) cells, or human embryonic kidney cells (e.g., HEK293).

Nucleic acid molecules comprising nucleotide sequences of interest can be stably integrated into a host cell genome or maintained on a stable episomal element in a suitable host cell using various gene delivery techniques well known in the art. See, e.g., U.S. Pat. No. 5,399,346.

Depending on the expression system and host selected, the molecules are produced by growing host cells transformed by an expression vector described above under conditions whereby the protein is expressed. The expressed protein is then isolated from the host cells and purified. If the expression system secretes the protein into growth media, the product can be purified directly from the media. If it is not secreted, it can be isolated from cell lysates. The selection of the appropriate growth conditions and recovery methods are within the skill of the art.

For representative methods for obtaining WNV sequences recombinantly, see, e.g., U.S. Patent Publication No. 2002/0164349; Davis et al., *J. Virol.* (2001) 75:4040-4047; and Yang et al., *J. Infect. Dis.* (2001) 184:809-816.

As explained above, one particularly preferred recombinant method of producing the WNV polypeptides, particularly the WNV PrM/E polypeptide, involves intracellular production. Production in this way produces highly immunogenic heterodimers and complexes of heterodimers. Secreted proteins do not always retain the native conformation and may include modified glycosylation patterns. Thus, purification of intracellularly produced WNV polypeptides from cells rather than from culture medium can be used in order to preserve the native conformation. For example, it has been shown herein that a WNV PrM/E polypeptide produced intracellularly in mammalian cells displays improved biological properties. The molecules so produced perform better in assays and appear to be more immunoreactive and therefore provide improved diagnostic reagents, as compared to their secreted counterparts. While not wishing to be bound by any particular theory, the intracellularly expressed forms of WNV proteins may more closely resemble the native viral proteins due to the carbohydrate motifs present on the molecules, while the secreted glycoproteins may contain modified carbohydrate moieties or glycosylation patterns. Furthermore, the intracellularly produced forms may be conformationally different than the secreted forms.

Intracellular forms of the WNV proteins can be produced using the recombinant methods described above. Production in mammalian hosts, such as but not limited to production in CHO and HEK293 cells, is particularly desirable. In order to produce the protein intracellularly, transformed cells are cultured for an amount of time such that the majority of protein is expressed intracellularly and not secreted. The cells are then disrupted using chemical, physical or mechanical means, which lyse the cells yet keep the WNV polypeptides substantially intact and the proteins recovered from the intracellular extract. Intracellular proteins can also be obtained by removing components from the cell wall or membrane, e.g., by the use of detergents or organic solvents, such that leakage of the WNV polypeptides occurs. Such methods are known to those of skill in the art and are described in, e.g., *Protein Purification Applications: A Practical Approach*, (E. L. V. Harris and S. Angal, Eds., 1990).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS.

The particular technique used to disrupt the cells is largely a matter of choice and will depend on the cell type in which the polypeptide is expressed, culture conditions and any pretreatment used. Preferably, for the production of the recombinant PrM/E polypeptide of the present invention, the cells are treated with a hypotonic solution (i.e. a solution having an ionic strength less than physiological saline, e.g., 10 mM Tris-HCl) to lyse the outer membrane.

Following disruption of the cells, insoluble cellular components are separated from the soluble cell contents, generally by centrifugation, and the intracellularly produced polypeptides are recovered with the insoluble portion, which contains substantially all of the membrane component of the cells. The insoluble portion is then treated with a non-ionic detergent, such as surfactant consisting of the octyl- or nonylphenoxy polyoxyethanols (for example the commercially available Triton series, particularly Triton X-100), polyoxyethylene sorbitan esters (Tween series) and polyoxyethylene ethers or esters, in order to solubilize the membrane component and release the WNV polypeptide, such as the WNV PrM/E polypeptide. The released polypeptide is then further purified, using standard purification techniques such as but not limited to, one or more column chromatography purification steps, such as but not limited to ion-exchange chromatography, size-exclusion chromatography, electrophoresis, HPLC, immunoadsorbent techniques, affinity chromatography, immunoprecipitation, and the like.

For example, one method for obtaining the intracellular WNV polypeptides of the present invention involves affinity purification, such as by immunoaffinity chromatography using antibodies specific for the desired WNV antigen, or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the polypeptides can be further purified using conventional techniques well known in the art, such as by any of the techniques described in the examples, e.g., using a hydroxyapatite column, particularly under high salt buffer conditions (e.g., about 200 mM NaCl), recovering the flowthrough fractions that contain the WNV PrM/E polypeptide, and subsequently using a cation exchange column (e.g., SP-Sepharose). Preferably, a non-ionic detergent maintained in the buffers during the purification process. As shown in the examples, these techniques provide for a highly purified antigen that can subsequently be used in vaccine compositions as well as a highly sensitive diagnostic reagent.

Compositions Comprising WNV Polypeptides or Polynucleotides

The invention provides immunogenic compositions including the above-described WNV polypeptides or polynucleotides. The compositions include a WNV PrM/E heterodimer or a complex of heterodimers, the heterodimer consisting of a recombinant WNV PrM polypeptide and a recombinant WNV E polypeptide. Preferably, the PrM portion of the heterodimer includes the sequence of amino acids depicted at positions 1-167 of FIG. 13 (124-290 of FIG. 2) and the E portion of the heterodimer includes the sequence of amino acids depicted at positions 1-501 of FIG. 14 (291-791 of FIG. 2), or an immunogenic heterodimer or complex of heterodimers wherein the PrM and E portions each include a contiguous sequence of amino acids with at least 75% sequence identity to the PrM and E proteins, respectively, depicted in FIG. 2, such as sequences displaying at least about 80-90% or more sequence identity thereto, including any percent identity within these ranges, such as 81, 82, 83, 84, 85, 86, 87, 88, 89, 90, 91, 92, 93, 94, 95, 96, 97, 98, 99% sequence identity thereto. More preferably, the WNV PrM/E heterodimer is produced recombinantly by isolation of the intracellularly expressed WNV PrM/E polypeptide, as described herein.

For use in the therapeutic methods and vaccines described herein, the compositions of the invention preferably comprise a pharmaceutically acceptable carrier. The carrier should not itself induce the production of antibodies harmful to the host. Pharmaceutically acceptable carriers are well known to those in the art. Such carriers include, but are not limited to, large, slowly metabolized, macromolecules, such as proteins, polysaccharides such as latex functionalized sepharose, agarose, cellulose, cellulose beads and the like, polylactic acids, polyglycolic acids, polymeric amino acids such as polyglutamic acid, polylysine, and the like, amino acid copolymers, and inactive virus particles.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, glycerol, dextrose, ethanol, or the like, singly or in combination, as well as substances such as wetting agents, emulsifying agents, or pH buffering agents. Liposomes can also be used as a carrier for a composition of the invention and are described below.

If desired, co-stimulatory molecules which improve immunogen presentation to lymphocytes, such as B7-1 or B7-2, or cytokines such as GM-CSF, IL-2, and IL-12, can be included in a composition of the invention. Optionally, adjuvants can also be included in a composition. Adjuvants which can be used include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (U.S. Pat. No. 6,299,884, incorporated herein by reference in its entirety; Chapter 10 in *Vaccine design: the subunit and adjuvant approach*, eds. Powell & Newman, Plenum Press 1995), containing 5% Squalene, 0.5% TWEEN 80™, and 0.5% SPAN 85™ (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% TWEEN 80™, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% TWEEN80™, and one or more bacterial cell wall components from the group consisting of monophosphorylipid A (MPL), trehalose dimycolate (TDM), and cell wall skeleton (CWS), preferably MPL+CWS (DETOX™); (3) saponin adjuvants, such as QS21 or STIMULON™ (Cambridge Bioscience, Worcester, Mass.) may be used or particles generated therefrom such as ISCOMs (immunostimulating complexes), which ISCOMs may be devoid of additional detergent, see, e.g., International Publication No.

WO 00/07621; (4) Complete Freund's Adjuvant (CFA) and Incomplete Freund's Adjuvant (IFA); (5) cytolines, such as interleukins (IL-1, IL-2, IL-4, IL-5, IL-6, IL-7, IL-12 (International Publication No. WO 99/44636), etc.), interferons (e.g., gamma interferon), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); (7) MPL or 3-O-deacylated MPL (3dMPL) (see, e.g., GB 2220221), EP-A-0689454, optionally in the substantial absence of alum when used with pneumococcal saccharides (see, e.g., International Publication No. WO 00/56358); (8) combinations of 3dMPL with, for example, QS21 and/or oil-in-water emulsions (see, e.g., EP-A-0835318, EP-A-0735898, EP-A-0761231; (9) oligonucleotides comprising CpG motifs (see, e.g., Roman et al. (1997) *Nat. Med.* 3:849-854; Weiner et al. (1997)*Proc. Natl. Acad. Sci. USA* 94:10833-10837; Davis et al. (1998) *J. Immunol.* 160:870-876; Chu et al. (1997) *J. Exp. Med.* 186:1623-1631; Lipford et al. (1997) *Eur. J. Immunol.* 27:2340-2344; Moldoveanu et al. (1988) *Vaccine* 16:1216-1224; Krieg et al. (1995) *Nature* 374:546-549; Klinman et al. (1996) *Proc. Natl. Acad. Sci. USA* 93:2879-2883; Ballas et al. (1996) *J. Immunol.* 157: 1840-1845; Cowdery et al. (1996) *J. Immunol.* 156:4570-4575; Halpern et al. (1996) *Cell Immunol.* 167:72-78; Yamamoto et al. (1988) *Jpn. J. Cancer Res.* 79:866-873; Stacey et al. (1996) *J. Immunol.* 157:2116-2122; Messina et al. (1991) *J. Immunol.* 147:1759-1764; Yi et al. (1996) *J. Immunol.* 157:4918-4925; Yi et al. (1996) *J. Immunol.* 157:5394-5402; Yi et al. (1998) *J. Immunol.* 160:4755-4761; Yi et al. (1998) *J. Immunol.* 160:5898-5906; International Publication Nos. WO 96/02555, WO 98/16247, WO 98/18810, WO 98/40100, WO 98/55495, WO 98/37919 and WO 98/52581), such as those containing at least one CG dinucleotide, with cytosine optionally replaced with 5-methylcytosine; (10) a polyoxyethylene ether or a polyoxyethylene ester (see, e.g., International Publication No. WO 99/52549); (11) a polyoxyethylene sorbitan ester surfactant in combination with an octoxynol (see, e.g., International Publication No. WO 01/21207) or a polyoxyethylene alkyl ether or ester surfactant in combination with at least one additional non-ionic surfactant such as an octoxynol (see, e.g., International Publication No. WO 01/21152); (12) a saponin and an immunostimulatory oligonucleotide such as a CpG oligonucleotide (see, e.g., International Publication No. WO 00/62800); (13) an immunostimulant and a particle of metal salt (see, e.g., International Publication No. WO 00/23105); and (14) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), -acetylmuramyl-L-alanyl-D-isogluatminyl-L-alanine-2-(1'-2'-dipahlitoyl-sn-glycero-3-hydroxyphosphoryloxy)-ethylamine (MTP-PE), etc.

Particularly preferred adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsions containing 4-5% w/v squalene, 0.25-1.0% w/v Tween 80 ™ (polyoxyelthylenesorbitan monooleate), and/or 0.25-1.0% Span 85™ (sorbitan trioleate), and optionally, N-acetylmuramyl-L-alanyl-D-isogluatminyl-L-alanine-2-(1'-2'-dipalmitoyl-sn-glycero-3-huydroxyphosphoryloxy)-ethylamine (MTP-PE), for example, the submicron oil-in-water emulsion known as "MF59" (International Publication No. WO 90/14837; U.S. Pat. Nos. 6,299,884 and 6,451,325, incorporated herein by reference in their entireties; and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296). MF59 contains 4-5% w/v Squalene (e.g., 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 μg/dose, more preferably 0-250 μg/dose and most preferably, 0-100 μg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 μg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121, and thr-MDP, also microfluidized into a submicron emulsion. MF75-MTP denotes an MF75 formulation that includes MTP, such as from 100-400 μg MTP-PE per dose.

Submicron oil-in-water emulsions, methods of making the same and immunostimulating agents, such as muramyl peptides, for use in the compositions, are described in detail in International Publication No. WO 90/14837 and U.S. Pat. Nos. 6,299,884 and 6,451,325, incorporated herein by reference in their entireties.

Other preferred agents to include in the subject compositions are immunostimulatory molecules such as immunostimulatory nucleic acid sequences (ISS), including but not limited to, unmethylated CpG motifs, such as CpG oligonucleotides. Oligonucleotides containing unmethylated CpG motifs have been shown to induce activation of B cells, NK cells and antigen-presenting cells (APCs), such as monocytes and macrophages. See, e.g., U.S. Pat. No. 6,207,646. Thus, adjuvants derived from the CpG family of molecules, CpG dinucleotides and synthetic oligonucleotides which comprise CpG motifs (see, e.g., Krieg et al. *Nature* (1995) 374:546 and Davis et al. *J. Immunol.* (1998) 160:870-876) such as any of the various immunostimulatory CpG oligonucleotides disclosed in U.S. Pat. No. 6,207,646, may be used in the subject methods and compositions. Such CpG oligonucleotides generally comprise at least 8 up to about 100 basepairs, preferably 8 to 40 basepairs, more preferably 15-35 basepairs, preferably 15-25 basepairs, and any number of basepairs between these values. For example, oligonucleotides comprising the consensus CpG motif, represented by the formula 5'-$X_1CGX_2$-3', where $X_1$ and $X_2$ are nucleotides and C is unmethylated, will find use as immunostimulatory CpG molecules. Generally, $X_1$ is A, G or T, and $X_2$ is C or T. Other useful CpG molecules include those captured by the formula 5'-$X_1X_2CGX_3X_4$, where $X_1$ and $X_2$ are a sequence such as GpT, GpG, GpA, ApA, ApT, ApG, CpT, CpA, CpG, TpA, TpT or TpG, and $X_3$ and $X_4$ are TpT, CpT, ApT, ApG, CpG, TpC, ApC, CpC, TpA, ApA, GpT, CpA, or TpG, wherein "p" signifies a phosphate bond. Preferably, the oligonucleotides do not include a GCG sequence at or near the 5'-and/or 3' terminus. Additionally, the CpG is preferably flanked on its 5'-end with two purines (preferably a GpA dinucleotide) or with a purine and a pyrimidine (preferably, GpT), and flanked on its 3'-end with two pyrimidines, preferably a TpT or TpC dinucleotide. Thus, preferred molecules will comprise the sequence GACGTT, GACGTC, GTCGTT or GTCGCT, and these sequences will be flanked by several additional nucleotides. The nucleotides outside of this central core area appear to be extremely amendable to change.

Moreover, the CpG oligonucleotides for use herein may be double- or single-stranded. Double-stranded molecules are more stable in vivo while single-stranded molecules display enhanced immune activity. Additionally, the phosphate backbone may be modified, such as phosphorodithioate-modified, in order to enhance the immunostimulatory activity of the CpG molecule. As described in U.S. Pat. No. 6,207,646, CpG molecules with phosphorothioate backbones preferentially activate B-cells, while those having phosphodiester backbones preferentially activate monocytic (macrophages, dendritic cells and monocytes) and NK cells.

CpG molecules can readily be tested for their ability to stimulate an immune response using standard techniques, well known in the art. For example, the ability of the molecule to stimulate a humoral and/or cellular immune response is readily determined using the immunoassays described above. Moreover, the immunogenic compositions can be administered with and without the CpG molecule to determine whether an immune response is enhanced.

The WNV molecules may also be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J. Microencap.* (1996). One preferred method for adsorbing macromolecules onto prepared microparticles is described in International Publication No. WO 00/050006, incorporated herein by reference in its entirety.

Compositions for use in the invention will comprise a therapeutically effective amount of the desired WNV molecule and any other of the above-mentioned components, as needed. By "therapeutically effective amount" is meant an amount of a protein or DNA encoding the same which will induce an immunological response, preferably a protective immunological response, in the individual to which it is administered, if the composition is to be used as a vaccine. Such a response will generally result in the development in the subject of an antibody-mediated and/or a secretory or cellular immune response to the composition. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδT cell populations.

It is known in the art that the addition of adjuvants and other immunostimulatory molecules or immune potentiators as described above are able to generate increased antigen-specific titers, thereby having a dose-reducing effect. Reduction in dose can be realized as less antigen and or fewer inoculums. Thus, it is contemplated that the heterodimer complex of the present invention can be combined with one or more of the immune potentiators described herein in order to minimize the need for repeated dosing regimens in order to achieve an effective immune response.

Administration

Typically, the immunogenic compositions (both DNA and protein) are prepared as injectables, either as liquid solutions or suspensions; solid forms suitable for solution in, or suspension in, liquid vehicles prior to injection may also be prepared. Thus, once formulated, the compositions are conventionally administered parenterally, e.g., by injection, either subcutaneously or intramuscularly. For example, the immunogen is preferably administered intramuscularly to a large mammal, such as a primate, for example, a baboon, chimpanzee, or human. Additional formulations suitable for other modes of administration include oral and pulmonary formulations, suppositories, and transdermal applications. The immunogens can be administered either to a mammal that is not infected with a WNV or can be administered to a WNV-infected mammal.

Dosage treatment may be a single dose schedule or a multiple dose schedule. Preferably, the effective amount is sufficient to bring about treatment or prevention of disease symptoms. The exact amount necessary will vary depending on the subject being treated; the age and general condition of the individual to be treated; the capacity of the individual's immune system to synthesize antibodies; the degree of protection desired; the severity of the condition being treated; the particular macromolecule selected and its mode of administration, and choice of adjuvant, among other factors. An appropriate effective amount can be readily determined by one of skill in the art. A "therapeutically effective amount" will fall in a relatively broad range that can be determined through routine trials using in vitro and in vivo models known in the art.

Thus, for example, if polypeptide immunogens are delivered, generally the amount administered will be about 0.1 μg to about 5.0 mg of immunogen per dose, or any amount between the stated ranges, such as 0.5 μg to about 10 mg, 1 μg to about 2 mg, 2.5 μg to about 250 μg, 4 μg to about 200 μg, such as 4, 5, 6, 7, 8, 10 . . . 20 . . . 30 . . . 40 . . . 50 . . . 60 . . . 70 . . . 80 . . . 90 . . . 100, etc., μg per dose.

As explained above, expression constructs, such as constructs encoding individual WNV immunogens or fusions, may be used for nucleic acid immunization to stimulate an immunological response, such as a cellular immune response and/or humoral immune response, using standard gene delivery protocols. Methods for gene delivery are known in the art. See, e.g., U.S. Pat. Nos. 5,399,346, 5,580,859, 5,589,466, incorporated by reference herein in their entireties. Genes can be delivered either directly to the subject or, alternatively, delivered ex vivo, to cells derived from the subject and the cells reimplanted in the subject. For example, the constructs can be delivered as plasmid DNA, e.g., contained within a plasmid, such as pBR322, pUC, or ColE1.

Additionally, the expression constructs can be packaged in liposomes prior to delivery to the cells. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1-17; Straubinger et al., in *Methods of Enzymology* (1983), Vol. 101, pp. 512-527.

Liposomal preparations for use with the present invention include cationic (positively charged), anionic (negatively charged) and neutral preparations, with cationic liposomes particularly preferred. Cationic liposomes are readily available. For example, N[1-2,3-dioleyloxy)propyl]-N,N,N-triethyl-ammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413-7416). Other commercially available lipids include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194-4198; PCT Publication No. WO 90/11092 for a description of the synthesis of DOTAP (1,2-bis(oleoyloxy)-3-(trimethylammonio)propane) liposomes. The various liposome-nucleic acid complexes are prepared using methods known in the art. See, e.g., Straubinger et al., in METHODS OF IMMUNOLOGY (1983), Vol. 101, pp. 512-527; Szoka et al., *Proc. Natl. Acad. Sci. USA* (1978) 75:4194-4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA can also be delivered in cochleate lipid compositions similar to those described by Papahadjopoulos et al., *Biochem. Biophys. Acta*. (1975) 394:483-491. See, also, U.S. Pat. Nos. 4,663,161 and 4,871,488.

A number of viral based systems have been developed for gene transfer into mammalian cells. For example, retroviruses provide a convenient platform for gene delivery systems, such as murine sarcoma virus, mouse mammary tumor virus, Moloney murine leukemia virus, and Rous sarcoma virus. A selected gene can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, *BioTechniques* (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Tennn, *Cur. Opin. Genet. Develop*. (1993) 3:102-109. Briefly, retroviral gene delivery vehicles of the present invention may be readily constructed from a wide variety of retroviruses, including for example, B, C, and D type retroviruses as well as spumaviruses and lentiviruses such as FIV, HIV, HIV-1, HIV-2 and SIV (see RNA Tumor Viruses, Second Edition, Cold Spring Harbor Laboratory, 1985). Such retroviruses may be readily obtained from depositories or collections such as the American Type Culture Collection ("ATCC"; 10801 University Blvd., Manassas, Va. 20110-2209), or isolated from known sources using commonly available techniques.

A number of adenovirus vectors have also been described, such as adenovirus Type 2 and Type 5 vectors. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J. Virol.* (1994) 68:933-940; Barr et al., *Gene Therapy* (1994) 1:51-58; Berkner, K. L. *BioTechniques* (1988) 6:616-629; and Rich et al., *Human Gene Therapy* (1993) 4:461-476).

Molecular conjugate vectors, such as the adenovirus chimeric vectors described in Michael et al., *J. Biol. Chem.* (1993) 268:6866-6869 and Wagner et al., *Proc. Natl. Acad. Sci. USA* (1992) 89:6099-6103, can also be used for gene delivery.

Members of the Alphavirus genus, such as but not limited to vectors derived from the Sindbis virus (SIN), Semliki Forest virus (SFV), and Venezuelan equine encephalitis (VEE), will also find use as viral vectors for delivering the gene of interest. For a description of Sindbis-virus derived vectors useful for the practice of the instant methods, see, Dubensky et al., *J. Virol.* (1996) 70:508-519; International Publication Nos. WO 95/07995 and WO 96/17072; and U.S. Pat. No. 5,843,723 and U.S. Pat. No. 5,789,245, both incorporated herein by reference in their entireties.

Other vectors can be used, including but not limited to simian virus 40 and cytomegalovirus. Bacterial vectors, such as *Salmonella* spp. *Yersinia enterocolitica, Shigella* spp., *Vibrio cholerae, Mycobacterium* strain BCG, and Lieriea monocytogenes can be used. Minichromosomes such as MC and MC1, bacteriphages, cosmids (plasmids into which phage lambda cos sites have been inserted) and replicons (genetic elements that are capable of replication under their own control in a cell) can also be used.

The expression constructs may also be encapsulated, adsorbed to, or associated with, particulate carriers as described above. Such carriers present multiple copies of a selected molecule to the immune system and promote trapping and retention of molecules in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J. Microencap*. (1996). One preferred method for adsorbing macromolecules onto prepared microparticles is described in International Publication No. WO 00/050006, incorporated herein by reference in its entirety. Briefly, microparticles are rehydrated and dispersed to an essentially monomeric suspension of microparticles using dialyzable anionic or cationic detergents. Useful detergents include, but are not limited to, any of the various N-methylglucamides (known as MEGAs), such as heptanoyl-N-methylglucamide (MEGA-7), octanoyl-N-methylglucamide (MEGA-8), nonanoyl-N-methylglucamide (MEGA-9), and decanoyl-N-methyl-glucamide (MEGA-10); cholic acid; sodium cholate; deoxycholic acid; sodium deoxycholate; taurocholic acid; sodium taurocholate; taurodeoxycholic acid; sodium taurodeoxycholate; 3-[(3-cholamidopropyl)dimethylammonio]-1-propane-sulfonate (CHAPS); 3-[(3-cholamidopropyl) dimethylammonio]-2-hydroxy-1-propane-sulfonate (CHAPSO); -dodecyl-N,N-dimethyl-3-ammonio-1-propane-sulfonate (ZWITTERGENT 3-12); N,N-bis-(3-D-gluconeamidopropyl)-deoxycholamide (DEOXY-BIGCHAP); -octylglucoside; sucrose monolaurate; glycocholic acid/sodium glycocholate; laurosarcosine (sodium salt); glycodeoxycholic acid/sodium glycodeoxycholate; sodium dodceyl sulfate (SDS); 3-(trimethylsilyl)-1-propanesulfonic acid (DSS); cetrimide (CTAB, the principal component of which is hexadecyltrimethylammonium bromide); hexadecyltrimethylammonium bromide; dodecyltrimethylammonium bromide; hexadecyltrimethyl-ammonium bromide; tetradecyltrimethylammonium bromide; benzyl dimethyldodecylammonium bromide; benzyl dimethylhexadecylammonium chloride; and benzyl dimethyltetra-decylammonium bromide. The above detergents are commercially available from e.g., Sigma Chemical Co., St. Louis, Mo. Various cationic lipids known in the art can also be used as detergents. See Balasubramaniam et al., 1996, *Gene Ther.*, 3:163-72 and Gao, X., and L. Huang. 1995, *Gene Ther.*, 2:7110-722.

A wide variety of other methods can be used to deliver the expression constructs to cells. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, liposomes, peptoid delivery, or microinjection. See, e.g., Sambrook et al., supra, for a discussion of techniques for transforming cells of interest; and Felgner, P. L., *Advanced Drug Delivery Reviews* (1990) 5:163-187, for a review of delivery systems useful for gene transfer. Methods of delivering DNA using electroporation are described in, e.g., U.S. Pat. Nos. 6,132,419; 6,451,002, 6,418,341, 6,233,483, U.S. Patent Publication No. 2002/0146831; and International Publication No. WO/0045823, all of which are incorporated herein by reference in their entireties.

Moreover, the WNV polynucleotides can be adsorbed to, or entrapped within, an ISCOM. Classic ISCOMs are formed by combination of cholesterol, saponin, phospholipid, and immunogens, such as viral envelope proteins. Generally, the WNV molecules (usually with a hydrophobic region) are solubilized in detergent and added to the reaction mixture, whereby ISCOMs are formed with the WNV molecule incorporated therein. ISCOM matrix compositions are formed identically, but without viral proteins. Proteins with high positive charge may be electrostatically bound in the ISCOM particles, rather than through hydrophobic forces. For a more detailed general discussion of saponins and ISCOMs, and methods of formulating ISCOMs, see Barr et al. (1998) *Adv. Drug Delivery Reviews* 32:247-271 (1998); U.S. Pat. Nos. 4,981,684, 5,178,860, 5,679,354 and 6,027,732, incorporated herein by reference in their entireties; European Publ. Nos. EPA 109,942; 180,564 and 231,039; and Coulter et al. (1998) *Vaccine* 16:1243.

Additionally, biolistic delivery systems employing particulate carriers such as gold and tungsten, are useful for delivering the expression constructs of the present invention. The particles are coated with the construct to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744.

The amount of WNV DNA delivered will generally be about 1 µg to 500 mg of DNA, such as 5 µg to 100 mg of DNA, e.g., 10 µg to 50 mg, or 100 µg to 5 mg, such as 20 . . . 30 . . . 40 . . . 50 . . . 60 . . . 100 . . . 200 µg and so on, to 500 µg DNA, and any integer between the stated ranges.

Administration of WNV polypeptide or polynucleotide compositions can elicit a cellular immune response, and/or an anti-WNV antibody titer in the mammal that lasts for at least 1 week, 2 weeks, 1 month, 2 months, 3 months, 4 months, 6 months, 1 year, or longer. The compositions can also be administered to provide a memory response. If such a response is achieved, antibody titers may decline over time, however exposure to WNV or the particular immunogen results in the rapid induction of antibodies, e.g., within only a few days. Optionally, antibody titers can be maintained in a mammal by providing one or more booster injections of the WNV polypeptides, at e.g., 2 weeks, 1 month, 2 months, 3 months, 4 months, 5 months, 6 months, 1 year, or more after the primary injection.

Preferably, an antibody titer of at least 10, 100, 150, 175, 200, 300, 400, 500, 750, 1,000, 1,500, 2,000, 3,000, 5,000, 10,000, 20,000, 30,000, 40,000, 50,000 (geometric mean titer), or higher, is elicited, or any number between the stated titers, as determined using a standard immunoassay.

WNV Antibodies

The immunogenic WNV recombinant polypeptides and compositions described herein can be used to produce WNV-specific polyclonal and monoclonal antibodies. WNV-specific polyclonal and monoclonal antibodies specifically bind to WNV antigens. Polyclonal antibodies can be produced by administering the polypeptides or compositions to a mammal, such as a mouse, a rabbit, a goat, or a horse. Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Monoclonal antibodies directed against WNV-specific epitopes present in the proteins can also be readily produced. Normal B cells from a mammal, such as a mouse (see, e,g., Kohler and Milstein, *Nature* (1975) 256:495-497), or a rabbit (see, e.g., U.S. Pat. No. 5,675,063 incorporated herein by reference in its entirety), immunized with a WNV recombinant polypeptide or composition, can be fused with, for example, HAT-sensitive mouse myeloma cells to produce hybridomas. Hybridomas producing WNV-specific antibodies can be identified using RIA or ELISA and isolated by cloning in semi-solid agar or by limiting dilution. Clones producing WNV-specific antibodies are isolated by another round of screening.

It may be desirable to provide chimeric antibodies, especially if the antibodies are to be used in preventive or therapeutic pharmaceutical preparations, such as for providing passive protection against WNV infection, as well as in WNV diagnostic preparations. Chimeric antibodies composed of human and non-human amino acid sequences may be formed from the mouse monoclonal antibody molecules to reduce their immunogenicity in humans (Winter et al. (1991) *Nature* 349:293; Lobuglio et al. (1989) *Proc. Nat. Acad. Sci. USA* 86:4220; Shaw et al. (1987) *J Immunol.* 138:4534; and Brown et al. (1987) *Cancer Res.* 47:3577; Riechmann et al. (1988) *Nature* 332:323; Verhoeyen et al. (1988) *Science* 239:1534; and Jones et al. (1986) *Nature* 321:522; EP Publication No. 519,596, published 23 Dec. 1992; and U.K. Patent Publication No. GB 2,276,169, published 21 Sep. 1994).

Antibody molecule fragments, e.g., $F(ab')_2$, Fv, and sFv molecules, that are capable of exhibiting immunological binding properties of the parent monoclonal antibody molecule can be produced using known techniques. Inbar et al. (1972) *Proc. Nat. Acad. Sci. USA* 69:2659; Hochman et al. (1976) *Biochem* 15:2706; Ehrlich et al. (1980) *Biochem* 19:4091; Huston et al. (1988) *Proc. Nat. Acad. Sci. USA* 85(16):5879; and U.S. Pat. Nos. 5,091,513 and 5,132,405, to Huston et al.; and U.S. Pat. No. 4,946,778, to Ladner et al.

In the alternative, a phage-display system can be used to expand monoclonal antibody molecule populations in vitro. Saiki, et al. (1986) *Nature* 324:163; Scharf et al. (1986) *Science* 233:1076; U.S. Pat. Nos. 4,683,195 and 4,683,202; Yang et al. (1995) *J Mol Biol* 254:392; Barbas, III et al. (1995) *Methods: Comp. Meth Enzymol* 8:94; Barbas, III et al. (1991) *Proc Natl Acad Sci USA* 88:7978.

Once generated, the phage display library can be used to improve the immunological binding affinity of the Fab molecules using known techniques. See, e.g., Figini et al. (1994) *J. Mol. Biol.* 239:68. The coding sequences for the heavy and light chain portions of the Fab molecules selected from the phage display library can be isolated or synthesized, and cloned into any suitable vector or replicon for expression. Any suitable expression system can be used, including those described above.

Antibodies which are directed against WNV epitopes, are particularly useful for detecting the presence of WNV or WNV antigens in a sample, such as a blood sample from a WNV-infected human. An immunoassay for a WNV antigen may utilize one antibody or several antibodies. An immunoassay for a WNV antigen may use, for example, a monoclonal antibody directed towards a WNV epitope, a combination of monoclonal antibodies directed towards epitopes of one WNV polypeptide, monoclonal antibodies directed towards epitopes of different WNV polypeptides, polyclonal antibodies directed towards the same WNV antigen, polyclonal antibodies directed towards different WNV antigens, or a combination of monoclonal and polyclonal antibodies. Preferably, an immunoassay to detect the presence of a WNV or a WNV antigen will utilize WNV-specific antibody that is directed towards an epitope in the WNV PrM/E heterodimer or heterodimer complex of the invention. Immunoassay protocols may be based, for example, upon competition, direct reaction, or sandwich type assays using, for example, labeled antibody and are described further below. The labels may be, for example, fluorescent, chemiluminescent, or radioactive.

The WNV-specific antibodies may further be used to isolate WNV particles or antigens by immunoaffinity columns. The antibodies can be affixed to a solid support by, for example, adsorption or by covalent linkage so that the antibodies retain their immunoselective activity. Optionally, spacer groups may be included so that the antigen binding site of the antibody remains accessible. The immobilized antibodies can then be used to bind WNV particles or antigens from a biological sample, such as blood or plasma. The bound WNV particles or antigens are recovered from the column matrix by, for example, a change in pH.

WNV Diagnostic Assays

As explained above, the immunogenic WNV polypeptides and compositions and antibodies that specifically bind WNV polypeptides can be used as reagents in assays to detect WNV infection. Typically, the presence of WNV in a biological sample will be determined by the presence of antibodies to WNV in the sample, although in appropriate cases the presence of the viral proteins (i.e., antigens) may be detected and used as an indicator of WNV in the sample. The above reagents can be used for detecting WNV in blood samples, including without limitation, in whole blood, serum and plasma. The immunogens and antibodies can be used to detect WNV infection in a subject, as well as to detect WNV contamination in donated blood samples. Thus, aliquots from individual donated samples or pooled samples can be screened for the presence of WNV and those samples or pooled samples contaminated with WNV can be eliminated before they are combined. In this way, a blood supply substantially free of WNV contamination can be provided. By "substantially free of WNV" is meant that the presence of WNV is not detected using the assays described herein, preferably using the strip immunoblot assay described more fully below.

Assays for use herein include Western blots; agglutination tests; enzyme-labeled and mediated immunoassays, such as ELISAs; biotin/avidin type assays; antigen sandwich assay, antibody sandwich assays, antigen/antibody combination assays, radioimmunoassays; immunoelectrophoresis; immunoprecipitation, and the like. The reactions generally include detectable labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound antibody or antigen in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

In one aspect of the invention, the immunogenic WNV polypeptides and compositions can be used for capture or detection or both of anti-WNV antibodies in a sample. In another aspect of the invention, recombinant antibodies to the immunogenic WNV polypeptides can be used for the capture or detection or both of WNV antigens in a sample. By "capture" of an analyte (i.e., anti-WNV antibodies or WNV antigens in a sample) is meant that the analyte can be separated from other components of the sample by virtue of the binding of the capture molecule. Typically, the capture molecule is associated with a solid support, either directly or indirectly. Typically, the detection molecule is associated with a detectable label, either directly or indirectly.

Typically, a solid support is first reacted with a solid phase component (e.g., one or more immunogenic WNV polypeptides or recombinant anti-WNV antibodies) under suitable binding conditions such that the component is sufficiently immobilized to the support. Sometimes, immobilization to the support can be enhanced by first coupling to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigen or antibody to the support include polysaccharides, polylactic acids, polyglycolic acids, polymeric amino acids, amino acid copolymers, and the like. Such molecules and methods of coupling these molecules are well known to those of ordinary skill in the art. See, e.g., Brinkley, M. A. *Bioconjugate Chem.* (1992) 3:2-13; Hashida et al., *J. Appl. Biochem.* (1984) 6:56-63; and Anjaneyulu and Staros, *International J. of Peptide and Protein Res.* (1987) 30:117-124.

After reacting the solid support with the solid phase component, any non-immobilized solid-phase components are removed from the support by washing, and the support-bound component is then contacted with a biological sample suspected of containing the analyte component (i.e., WNV antigens or antibodies) under suitable binding conditions. After washing to remove any non-bound analyte, a secondary binder moiety can be added under suitable binding conditions, wherein the secondary binder is capable of associating selectively with the bound analyte. The presence of the secondary binder can then be detected using techniques well known in the art.

More particularly, an ELISA method can be used, wherein the wells of a microtiter plate are coated with one or more WNV epitopes, polypeptides, compositions or WNV-specific antibodies according to the present invention. A biological sample containing or suspected of containing either anti-WNV immunoglobulin molecules or WNV antigens is then added to the coated wells. After a period of incubation sufficient to allow antigen-antibody binding, the plate(s) can be washed to remove unbound moieties and a detectably labeled secondary binding molecule added. The secondary binding molecule is allowed to react with any captured sample, the plate washed and the presence of the secondary binding molecule detected using methods well known in the art.

In one particular format, an ELISA antigen sandwich format is used. In this case, the solid support is coated with a WNV antigen, preferably—a WNV PrM/E heterodimer or a complex of heterodimers, wherein the PrM portion of the heterodimer includes the sequence of amino acids depicted at positions 124-290 of FIG. 2 and the E portion of the heterodimer includes the sequence of amino acids depicted at positions 291-791 of FIG. 2, or an immunogenic heterodimer or complex of heterodimers wherein the PrM and E portions each include a contiguous sequence of amino acids with at least 75% sequence identity to the PrM and E proteins, respectively, depicted in FIG. 2, such as sequences displaying at least about 80-90% or more sequence identity thereto, including any percent identity within these ranges, such as 81, 82, 83, 84, 85, 86, 87, 88, 89, 90, 91, 92, 93, 94, 95, 96, 97, 98, 99% sequence identity thereto. The sample is then contacted with the support under conditions that allow anti-WNV antibodies, if present, to bind the WNV PrM/E antigen to form an antigen/antibody complex. Unbound reagents are removed and an enzymatically labeled antigen that reacts with the bound antigen/antibody complex, such as a labeled WNV PrM/E antigen or a labeled WNV envelope antigen, is added. An enzyme substrate is used to generate a signal.

In another format, the solid support is coated with species-specific anti-isotypic antibodies (e.g., anti-human IgM antibodies, anti-human IgG antibodies, anti-human IgA antibodies, etc). The support is then contacted with the sample under conditions that allow binding of antibodies present in the sample to the anti-isotypic antibodies. Unbound antibodies can be removed and the presence of bound anti-WNV antibodies is detected using a labeled WNV polypeptide of the present invention, particularly a labeled WNV PrM/E polypeptide. The label will typically be an enzyme label, e.g., a HRP, AP.

In another embodiment, the presence of bound WNV analytes from a biological sample can be readily detected using a secondary binder comprising an antibody directed against the analytes. A number of anti-human immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Other formats for detection of anti-WNV antibodies in a sample are known and the WNV polypeptides of the present invention can be used with any known format that employs a WNV antigen. For example, the capture IgM-ELISA described in Martin et al. (J. Clin Microbiol. 2000 38:1823-1826) and the indirect IgG ELISA described in Johnson et al. (J. Clin Microbiol. 2000 38:1827-1831). Other useful formats include a microsphere immunoassay (Wong et al. J. Clin. Microbiol. 2004 42:65-72) and epitope-blocking ELISA (Blitvich et al. J. Clin. Microbiol. 2003 41:2676-2679).

The immunogenic composition comprising a WNV heterodimer can be used in an IgM capture ELISA as follows. Anti-human IgM antibody (e.g., goat anti-human IgM antibody) is attached to a solid support, the support is contacted with a sample to be tested for the presence of human IgM to WNV, under conditions that would allow the binding of the anti-WNV IgM, if present, to the anti-human IgM antibody attached to the solid support, to form an antibody/antibody complex. The WNV PrM/E heterodimer composition is added under conditions that would allow binding to the anti-WNV IgM in the antibody/antibody complex forming an antibody/antibody/heterodimer complex. Unbound heterodimer composition is removed and a detectably labeled anti-WNV antibody is added under conditions that would allow binding to the bound heterodimer composition. The presence of IgM to WNV in the sample is determined by the presence of detectably labeled anti-WNV antibody to the bound anti-human IgM Ab/human anti-WNV IgM/WNV heterodimer complex attached to the solid support.

The immunogenic composition comprising a WNV heterodimer can also be used in an indirect IgG ELISA as follows. Antibody specific for WNV antigen (in particular, WNV PrM, M, or E) is attached to a solid support, the support is contacted with the WNV heterodimer composition under conditions that would allow binding to the anti-WNV antibody bound to the support to form an antibody/heterodimer complex. Unbound heterodimer is removed and the support is contacted with a sample to be tested for the presence of human IgG to WNV under conditions that would allow binding of human anti-WNV IgG, if present, to the heterodimer in the antibody/heterodimer complex. The presence of bound anti-WNV IgG can be detected using a detectably labeled anti-human IgG antibody.

While some of the foregoing assay formats are termed "ELISA" (Enzyme Linked ImmunoSorbant Assay) assays, it will be apparent to one of skill in the art that the use of a detectable label other than an "enzyme linked" binding moiety is possible and may be desirable in many situations. Other suitable detectable labels are described herein and are well known in the art.

Assays can also be conducted in solution, such that the WNV epitopes, polypeptides, compositions or antibodies and ligands specific for these molecules form complexes under precipitating conditions. In one particular embodiment, the molecules can be attached to a solid phase particle (e.g., an agarose bead or the like) using coupling techniques known in the art, such as by direct chemical or indirect coupling. The coated particle is then contacted under suitable binding conditions with a biological sample suspected of containing WNV antibodies or antigens. Cross-linking between bound antibodies causes the formation of complex aggregates which can be precipitated and separated from the sample using washing and/or centrifugation. The reaction mixture can be analyzed to determine the presence or absence of complexes using any of a number of standard methods, such as those immunodiagnostic methods described above.

In yet a further embodiment, an immunoaffinity matrix can be provided, wherein, for example, a polyclonal population of antibodies from a biological sample suspected of containing WNV antibodies is immobilized to a substrate. An initial affinity purification of the sample can be carried out using immobilized antigens. The resultant sample preparation will thus only contain anti-WNV moieties, avoiding potential nonspecific binding properties in the affinity support. A number of methods of immobilizing immunoglobulins (either intact or in specific fragments) at high yield and good retention of antigen binding activity are known in the art. Once the immunoglobulin molecules have been immobilized to provide an immunoaffinity matrix, labeled molecules are contacted with the bound antibodies under suitable binding conditions. After any non-specifically bound WNV epitope has been washed from the immunoaffinity support, the presence of bound antigen can be determined by assaying for label using methods known in the art.

In a particularly preferred embodiment of the invention, a strip immunoblot assay (SIA) is used to detect WNV antibodies in a biological sample using one or more of the above-described immunogenic WNV polypeptides immobilized on the test strip. One preferred antigen is the WNV PrM/E heterodimer or a complex of heterodimers, wherein the PrM portion of the heterodimer includes the sequence of amino acids depicted at positions 124-290 of FIG. 2 and the E portion of the heterodimer includes the sequence of amino acids depicted at positions 291-791 of FIG. 2 or an immunogenic heterodimer or complex of heterodimers wherein the PrM and E portions each include a contiguous sequence of amino acids with at least 75% sequence identity to the PrM and E proteins, respectively, depicted in FIG. 2, such as displaying at least about 80-90% or more sequence identity thereto, including any percent identity within these ranges, such as 81, 82, 83, 84, 85, 86, 87, 88, 89, 90, 91, 92, 93, 94, 95, 96, 97, 98, 99% sequence identity thereto.

In particular, the present invention involves the use of SIA techniques, such as those known in the art, which combine traditional western and dot blotting techniques, e.g., the RIBA® (Chiron Corp., Emeryville, Calif.) SIA. The assay can be conducted in an antigen sandwich format. In these assays, one or more WNV antigens, such as the WNV PrM/E polypeptide, and optionally, one or more species specific anti-immunoglobulin antibodies, such as anti-human IgM antibody, anti-human IgG antibody and/or anti-human IgA antibody, are immobilized in discrete positions, e.g., as bands or dots, on a solid support, particularly a membrane support. By "discretely immobilized" or "immobilized in discrete positions" on a solid support is meant that the various reagents are immobilized on the support as separate components, in discrete and non-overlapping positions and not mixed, such that reactivity or lack thereof with each of the components present can be assessed individually. A biological sample suspected of containing antibodies to WNV is then reacted with the test membrane. Visualization of reactivity in the biological sample is accomplished using a WNV antigen enzyme-conjugate, capable of binding WNV antibodies which have complexed with immobilized antigen, in conjunction with a calorimetric enzyme substrate. Additionally, immunoglobulin molecules from the infected sample which have complexed with the anti-immunoglobulin antibodies immobilized on the test strip can also be bound by the WNV antigen enzyme-conjugate. The assay can be performed manually or used in an automated format.

Figure 9:
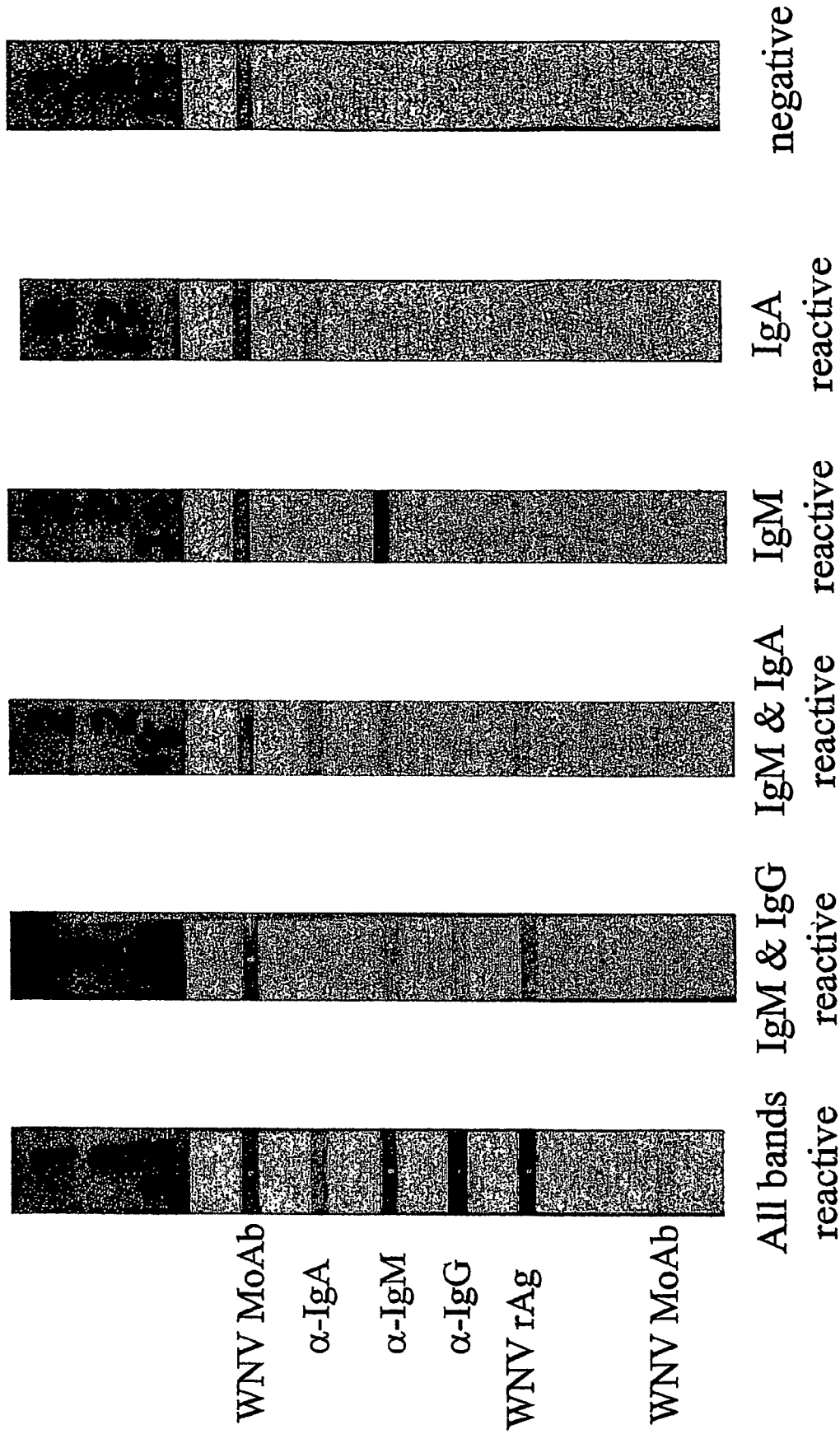
FIG. 9 shows the various patterns of IgG, IgM and IgA reactivity observed in positive samples.

By using antibodies directed against more than one class of immunoglobulins described above, such as anti-IgM antibodies, anti-IgG antibodies, and/or anti-IgA antibodies, greater specificity is achieved and false-positives can be avoided. For example, it is known that other flaviviruses, such as Dengue virus, produce IgM, IgG and IgA at different times during the course of infection. See, e.g., Koraka et al., *J. Clin. Microbiol.* (2001) 39:4332-4338. It is generally believed that IgM is produced first and may persist from approximately six months to about two or more years. IgG also persists for years. Finally, IgA antibodies may be higher in the acute phase of infection and persist for only a short time, for example, a week. Conventional WNV diagnostics currently available rely on an IgM capture ELISA format. However, since IgM molecules persist well after infection is resolved, these assays will show positive results even in individuals that are no longer actively infected. Thus, by using multiple immunoglobulin classes and, in particular IgA, the presence of active infection can be accurately detected. Representative results for the various Ig classes are shown in FIG. 9.

Internal controls, such as antibodies directed against a WNV antigen, particularly WNV envelope epitopes, can also be immobilized on the test strip. One particularly convenient method is to include the same antibody in two separate known positions on the test strip, but in high and low concentrations. These controls will be bound by the labeled WNV polypeptide used for detection of the sample antibodies. The low concentration control is designed to provide the lower cutoff for a positive versus negative result. The higher concentration control is designed to provide a basis for a highly reactive sample. In this configuration, then, a sample is considered positive only if reactivity is greater than or equal to the low level antibody control band, which can be arbitrarily defined to represent a 1+ reactivity. A reactivity equivalent to the high level antibody control band is considered to represent, for example, a reactivity of 3+. Reactivity intensity intermediate between the low and high level antibody control bands is considered to be 2+, and reactivity stronger than the high level antibody band is considered to be 4+. Representative reactivities are shown in FIG. 8.

Solid supports which can be used in the practice of the strip immunoblot assays include, but are not limited to, membrane supports derived from a number of primary polymers including cellulose, polyamide (nylon), polyacrylonitrile, polyvinylidene difluoride, polysulfone, polypropylene, polyester, polyethylene and composite resins consisting of combinations or derivatives of the above. Particularly preferred are supports derived from cellulose, such as nitrocellulose membranes, as well as nylon membranes. The substrate generally includes the desired membrane with an inert plastic backing as a support.

The amount of antigen applied to the membrane varies, depending on the antigen in question. Generally, the antigen will be applied to the strip in an amount of about 20-500 ng/strip, preferably 50-250 ng/strip, more preferably 75-150 ng/strip. One of skill in the art can readily determine the amount of antigen necessary to produce a useable result.

The anti-immunoglobulin antibodies, such as anti-human IgM antibody, anti-human IgG antibody and/or anti-human IgA antibody, can be present in an amount of about 100 to about 2000 ng/strip, preferably about 200 to about 1000 ng/strip, such as 400-900 ng/strip. The anti-IgM antibody can be present in lesser amounts as IgM appears to be the most prevalent immunoglobulin class found in infected samples. Thus, for example, anti-IgG antibody and anti-IgA antibody may be present in an amount such as 800 ng/strip while anti-IgM antibody might be present in an amount of 500 ng on the same strip.

The low concentration internal control antibody can be present in an amount of e.g., 25-200 ng, such as 50-150 ng, e.g., 100 ng/strip. The high level control will be present in an amount sufficiently higher to give a highly positive result, such as at 200-500 ng, particularly 250-350 ng, e.g., 300 ng/strip.

Typically for ELISAs, when used for detection of bound antibodies, immunogenic WNV polypeptide of the invention will be conjugated to a detectable enzyme label, such as horseradish peroxidase (HRP), glucose oxidase, β-galactosidase, alkaline phosphatase (AP) and urease, among others, using methods known to those of skill in the art. An appropriate enzyme substrate is then used to generate a detectable signal. Alternatively, the detection WNV polypeptide may be labeled with any detectable label.

The above-described assay reagents, including WNV polypeptides and/or antibodies thereto, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits. A preferred kit will comprise a membrane including an immunogenic WNV polypeptide of the present invention discretely immobilized thereon and, optionally, a labeled immunogenic WNV polypeptide for detection of bound antibodies, together with written instructions for use in an immunoassay. Preferably, the immunogenic WNV polypeptide will be a WNV PrM/E polypeptide. Another preferred kit will comprise a membrane comprising an anti-isotypic antibody (e.g., an anti-IgM, an anti-IgG, or an anti-IgA antibody), preferably an anti-human Ig antibody, discretely immobilized thereon and a labeled immunogenic WNV polypeptide of the present invention for detection of bound antibodies, together with written instructions for use in an immunoassay. Preferably, the immunogenic WNV polypeptide will be a WNV PrM/E polypeptide.

2. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Enzymes were purchased from commercial sources, and used according to the manufacturers' directions.

In the isolation of DNA fragments, except where noted, all DNA manipulations were done according to standard procedures. See, Sambrook et al., supra. Restriction enzymes, $T_4$ DNA ligase, *E. coli*, DNA polymerase II, Klenow fragment, and other biological reagents can be purchased from commercial suppliers and used according to the manufacturers' directions. Double stranded DNA fragments were separated on agarose gels.

Sources for chemical reagents generally include Sigma Chemical Company, St. Louis, Mo.; Alrich, Milwaukee, Wis.; Roche Molecular Biochemicals, Indianapolis, Ind. Plasmid design.

EXAMPLE 1

Yeast Expression of WNV Polypeptides

The following constructs were made and expressed in yeast:
1. WNV capsid: A WNV capsid polypeptide, including amino acids 1-123 of FIG. 2 (13.8 kDa);
2. SOD/WNV, capsid: A fusion of human superoxide dismutase (hSOD) and WNV capsid polypeptide, including amino acids 1 to 154 of hSOD and amino acids 1-123 of FIG. 2 (31.3 kDa);
3. WNV PrM/E: A WNV protein including the entire WNV membrane precursor protein (amino acids 124-290 of FIG. 2) and the WNV envelope (amino acids 291-791 of FIG. 2) (74.1 kDa);
4. SOD/WNV PrM/E: A fusion of hSOD as described above with a WNV protein including the entire WNV membrane precursor protein (amino acids 124-290 of FIG. 2) and the WNV envelope (amino acids 291-791 of FIG. 2) (91.6kDa);
5. WNV envelope: A WNV envelope polypeptide including amino acids 291-791 of FIG. 2 (55.6 kDa);
6. SOD/WNV envelope: A fusion of hSOD as described above with a WNV envelope polypeptide including amino acids 291-791 of FIG. 2 (73 kDa);
7. WNV envelope-Q681: A C-terminally truncated WNV envelope polypeptide including amino acids 291-681 of FIG. 2 (43.4 kDa);
8. SOD/WNV envelope-Q681: A fusion of hSOD as described above with a C-terminally truncated WNV envelope polypeptide including amino acids 291-681 of FIG. 2 (60.9 kDa);
9. WNV envelope-H686: A C-terminally truncated WNV envelope polypeptide including amino acids 291-686 of FIG. 2 (44 kDa);
10. SOD/WNV envelope-H686: A fusion of hSOD as described above with a C-terminally truncated WNV envelope polypeptide including amino acids 291-686 of FIG. 2 (61.5 kDa);
11. WNV envelope-G691: A C-terminally truncated WNV envelope polypeptide including amino acids 291-691 of FIG. 2 (44.5 kDa);
12. SOD/WNV envelope-G691: A fusion of hSOD as described above with a C-terminally truncated WNV envelope polypeptide including amino acids 291-691 of FIG. 2 (62 kDa);
13. WNV envelope-K696: A C-terminally truncated WNV envelope polypeptide including amino acids 291-696 of FIG. 2 (45.1 kDa);
14. SOD/WNV envelope-K696: A fusion of hSOD as described above with a C-terminally truncated WNV envelope polypeptide including amino acids 291-696 of FIG. 2 (62.6 kDa);
15. WNV envelope-T701: A C-terminally truncated WNV envelope polypeptide including amino acids 291-701 of FIG. 2 (45.6 kDa);
16. SOD/WNV envelope-T701: A fusion of hSOD as described above with a C-terminally truncated WNV envelope polypeptide including amino acids 291-701 of FIG. 2 (63.1 kDa);
17. WNV envelope-Q706: A C-terminally truncated WNV envelope polypeptide including amino acids 291-706 of FIG. 2 (46.2 kDa);
18. SOD/WNV envelope-Q706: A fusion of hSOD as described above with a C-terminally truncated WNV envelope polypeptide including amino acids 291-706 of FIG. 2 (63.7 kDa);
19. WNV NS1: A WNV NS1 polypeptide including amino acids 792-1143 of FIG. 2 (39.1 kDa);
20. SOD/WNV NS1: A fusion of hSOD as described above with a WNV NS1 polypeptide including amino acids 792-1143 of FIG. 2 (56.6 kDa);

For yeast expression, WNV constructs as indicated above were made by incorporating the initiation ATG codon (methionine) as needed and including linker nucleotide sequences when the WNV gene was expressed as a fusion with hSOD. The sequence of hSOD is known (see, e.g., U.S. Pat. Nos. 6,331,421; 5,817,794; 5,710,033; 5,629,189; all incorporated herein by reference in their entireties) and the use of SOD as a fusion partner for expression of heterologous proteins is also well known (see, e.g., U.S. Pat. No. 5,342,921, incorporated herein by reference in its entirety). The resulting nucleotide sequences were cloned into the yeast expression vector pBS24.1 (Pichuantes et al., *Protein Eng., Principle*

*and Prac.* (1996) 5:129-161). This vector contains 2μ and inverted repeat (IR) sequences for autonomous replication in yeast, the α-factor terminator to ensure transcription termination, the ADH2/GAPDH promoter, the leu2-d and ura3 yeast genes for selection, and the β-lactamase gene and the ColE1 origin of replication for selection and bacterial propagation.

All recombinant proteins were expressed in *Saccharomyces cerevisiae* and protein was purified from yeast cells harvested several hours after depletion of glucose from the medium. This condition is needed to activate the ADH2/GAPDH promoter and trigger production of the foreign protein (Pichuantes et al., *J. Biol. Chem.* (1990) 265:13890-13898). Cells were broken with glass beads in a Dynomill using a lysis buffer and protein was recovered from the insoluble fraction (obtained by centrifugation) with increasing amounts of urea After centrifugation, the pellet containing the protein of interest was solubilized, cell debris was removed by centrifugation, and the recombinant WNV proteins purified therefrom by treatments with 0.1 N NaOH/25 mM DTT and use of gel filtration columns.

The *S. cerevisiae*-expressed proteins were purified as follows. Yeast cell pellets were obtained and washed with multiple urea/octyglucoside buffers. Protein was extracted by boiling with 2.3% SDS, and 25 mM DTT. The soluble antigen was subsequently purified by size exclusion chromatography on a Sephacryl S300 column in PBS containing 0.1% SDS and 25 mM DTT. The peak fractions were concentrated and boiled for 3 minutes and reapplied to the S300 column and peak fractions collected.

Yeast expression constructs for expression in *Pichia pastoris* were also made by cloning the nucleotide sequences into the expression vector pAO815 (see, U.S. Pat. No. 5,258,302, the disclosure of which is incorporated herein by reference in its entirety). The sequences included the AOX1 promoter and yeast α-factor leader for secretion.

EXAMPLE 2

Mammalian Expression of WNV Polypeptides

The following WNV PrM/E gene constructs were made for mammalian cell expression:

Construct #1. A WNV TPA/PrM/E construct encoding a WNV protein including the entire WNV membrane precursor protein (amino acids 124-290 of FIG. 2) and the WNV envelope (amino acids 291-791 of FIG. 2) (73 kDa). This construct also encoded a TPA leader sequence at the N-terminus of the protein. The sequence for the TPA leader is shown in FIG. 12. This TPA leader is naturally cleaved when the protein is expressed in mammalian cells.

Construct #2. A WNV capsid/PrM/E construct encoding a WNV protein precursor including a methionine initiation codon, amino acids 94-123 of the WNV capsid as depicted in FIG. 2, the entire WNV membrane precursor protein (amino acids 124-290 of FIG. 2) and the WNV envelope (amino acids 291-791 of FIG. 2) (73 kDa).

Construct #3. A WNV capsid/PrM/E construct encoding a WNV protein including a methionine initiation codon, amino acids 100-123 of the capsid as depicted in FIG. 2, the entire WNV membrane precursor protein (amino acids 124-290 of FIG. 2) and the WNV envelope (amino acids 291-791 of FIG. 2) (73 kDa).

Each of these constructs were cloned into vectors for expression in HEK293 cells or CHO cells.

Vectors including the PrM/E gene constructs were used to transfect HEK293 cells and CHO cells as follows.

A. HEK293 Cell Expression:

For expression of the PrM/E gene in HEK293 cells, a synthetically designed PrM/E gene from WNV was constructed (Construct #1, #2 or #3 described above) and cloned into pCMVkm2 (International Publication Number WO99/08711) for mammalian cell transient transfection in HEK293 cells. The pCMVKm2 vector was derived from pCMV6a (Chapman et al., *Nuc. Acids Res.* (1991) 19:3979-3986) and comprises a kanamycin selectable marker, a ColE1 origin of replication, a CMV promoter enhancer and Intron A, followed by an insertion site for the synthetic sequence described below, followed by a polyadenylation signal derived from bovine growth hormone. The WNV precursor was processed within the cell host to yield the mature viral envelope that was secreted into media as evidenced by the appearance of a protein band of approximately 54 kDa that comigrated with the envelope protein of viral particles propagated in Vero cells. This protein band was immunoreactive on Western blots, with monoclonal antibodies raised against the envelope protein of Kunjin virus and with a human WNV-positive serum.

In particular for one vector, the synthetically designed PrM/E gene sequence (Construct #1 and as shown in FIGS. 3A-3B) was made in order to express the PrM/E protein including the entire WNV membrane precursor protein and the WNV envelope. Unique restriction sites were introduced into the synthetically designed gene to allow for further manipulations. The TPA leader sequence in an EcoRI/NheI fragment and the synthetic gene as an NheI/BamHI fragment were cloned into pCMVkm2 to create pCMVkm2.TPA.prME #2 for transient expression in HEK293 cells. To do so, approximately $2\times10^6$ Cells were absorbed with 40 μg of DNA plasmid and fugene for 24 hrs at 37° C. in a volume of 100 ml. 300 ml of media containing 6% FCS was then added. Cells were then fed with 200 ml of media for the last 24 hrs and incubated at 37° C. in a 1 liter glass vessel for a total of 72 hours. Cells were then harvested, washed once with PBS and frozen at −80° C.

B. CHO Cell Expression:

A WNV PrM/E nucleic acid construct encoding a WNV protein including the entire WNV membrane precursor protein (amino acids 124-290 of FIG. 2) and the WNV envelope (amino acids 291-791 of FIG. 2) (73 kDa) was synthesized. The construct also encoded a TPA leader sequence at the N-terminus of the protein. The sequence for the TPA leader is shown in FIG. 12. This leader is naturally cleaved after the protein is produced. Also, when this construct is expressed in host cells, the PrM and E polyprotein is cleaved to yield two separate polypeptides, PrM and E, which assemble in the host cell endoplasmic reticulum membrane as heterodimers.

For expression in CHO cells, the synthetically designed PrM/E gene sequence described above (construct # 1) and shown in FIGS. 3A-3B was cloned into pCMVIII (described U.S. Pat. No. 6,602,705, incorporated herein by reference in its entirety), as an EcoRI/XmaI fragment to create pCMVIII-TPA.prME #12. Briefly, construction of pCMVIII was as follows. To construct a DHFR cassette, the EMCV IRES (internal ribosome entry site) leader was PCR-amplified from pCite-4a+ (Novagen, Inc., Milwaukee, Wis.) and inserted into pET-23d (Novagen, Inc., Milwaukee, Wis.) as an Xba-Nco fragment to give pET-EMCV. The dhfr gene was PCR-amplified from pESN2dhfr to give a product with a Gly-Gly-Gly-Ser spacer in place of the translation stop codon and inserted as an Nco-BamH1 fragment to give pET-E-DHFR. Next, the attenuated neo gene was PCR-amplified from a pSV2Neo (Clontech, Palo Alto, Calif.) derivative and inserted into the unique BamH1 site of pET-E-DHFR to give pET-E-DHFR/

Neo(m2). Then, the bovine growth hormone terminator from pCDNA3 (Invitrogen, Inc., Carlsbad, Calif.) was inserted downstream of the neo gene to give pET-B-DHFR/Neo (m2) BGHt. The EMCV-dhfr/neo selectable marker cassette fragment was prepared by cleavage of pET-E-DHFR/Neo(m2) BGHt. The CMV enhancer/promoter plus Intron A was transferred from pCMV6a (Chapman et al., *Nuc. Acids Res.* (1991) 19:3979-3986) as a HindIII-Sal1 fragment into pUC19 (New England Biolabs, Inc., Beverly, Mass.). The vector backbone of pUC19 was deleted from the Nde1 to the Sap1 sites. The above described DHFR cassette was added to the construct such that the EMCV IRES followed the CMV promoter to produce the final construct. The vector also contained an ampr gene and an SV40 origin of replication.

CHO (DG44) cells were transfected with the DNA of the vector pCMVIIITPA.prME #12. G418 was used for primary selection and methotrexate for secondary selection of clones. Positive clones were identified by immunofluorescent staining with an monoclonal antibody to WNV E glycoprotein of methanol fixed monolayers. A high expressing clone was grown in a bioreactor for 45 days with continuous harvesting of cells from the bioreactor. Cells were harvested and frozen at −80° C. in Phosphate Buffered Saline (PBS). For purification of PrM/E heterodimer complexes from the stably transfected CHO cells, purification of recombinant PrM/E heterodimer complex from stably transfected CHO cells was performed as described below in C.

C. Purification of Recombinant PrM/E Heterodimer Complex:

Expression of the WNV PrM/E protein intracellularly in mammalian cells as described above produced a full-length PrM and E proteins with the transmembrane regions of both proteins intact and assembled into heterodimers. The heterodimers included a PrM polypeptide and an E polypeptide in approximately a 1:1 ratio. This product was purified from HEK293 and CHO cells as follows.

Cell detergent extraction. PrM/E heterodimer complex is purified following lysis of cells in a hypotonic buffer, extraction with non-ionic detergent and purification with several chromatography steps.

Frozen transfected HEK293 or CHO cells as described in Example 2A or 2B were thawed and lysed by suspension in a 10 mM Tris-HCl, pH 8.0 buffer followed by douncing in a Kontes glass dounce in an ice bucket. Following lysis, the solution was centrifuged. In this process, PrM/E heterodimer bound to cell membranes located in the cell pellet was obtained. After centrifugation, the membrane pellet was resuspended in a 100 mm Tris-HCl, pH 8.0 buffer containing 4% Triton X-100 detergent and again dounced in an ice bucket. After centrifugation, the supernatant was diluted with an equal volume of 2 M NaCl and centrifuged again. This extraction with a non-ionic detergent solubilizes the PrM/E heterodimers. The resulting supernatant, referred to as a Triton X-100 extract, was frozen at −80° C.

GNA lectin chromatography. The Triton X-100 extract was thawed and filtered with 5 µm and 1 µm filters then applied to a Galanthus nivalis lectin agarose (GNA) column previously equilibrated with 25 mM phosphate buffer, pH 6.8, containing 1 M NaCl and 2.0% Triton X-100 detergent. The column was washed with 25 mM phosphate buffer, pH 6.8, containing 1 M NaCl and 0.1% Triton X-100 detergent. The PrM/E polypeptide was eluted with 1 M methyl-d-alpha-manoside in 25 mM phosphate buffer, pH 6.8, containing 1 M NaCl and 0.1% Triton X-100 detergent. The E protein of West Nile Virus is known to contain one glycosylation site which results in a high mannose carbohydrate glycoprotein. Utilizing the affinity for this high mannose glycoprotein, the PrM/E heterodimers were purified in this step via an affinity for the lectin column Accordingly, other components having a high affinity for the E protein can also be used to purify the heterodimer complex.

HAP chromatography. GNA eluate material was concentrated and then diluted to reduce the NaCl content to 200 mM. It was then applied to a hydroxyapatite (HAP) equilibrated with 25 mM phosphate buffer, pH 6.8, containing 200 mM NaCl and 0.1% Triton X-100 detergent. The flow through material was collected and dialyzed against 25 mM phosphate buffer, pH 6.0, containing 0.1% Triton X-100 detergent overnight at 4° C.

SP chromatography. The dialyzed antigen was applied to a SP sepharose high performance column previously equilibrated in 25 mM phosphate buffer, pH 6.0, containing 0.1% Triton X-100 detergent. The PrM/E antigen was eluted with 25 mM phosphate buffer, pH 6.0, containing 0.5 M NaCl and 0.1% Triton X-100 detergent.

The resulting eluate contains the PrM/E heterodimer complexes of the invention at a purity of about 90%. This product is used as the PrM/E heterodimer complex for immunization and other processes requiring West Nile PrM/E immunogenic compositions described herein.

D. Characterization of the Purified Recombinant PrM/E Polypeptide:

Using the above technique, the PrM/E polypeptide could be purified to approximately 85% to 90% purity as assessed by SDS-PAGE. Moreover, antibodies from convalescent WNV human patient serum bound to both the PrM and E antigens as assayed in an immunoblot assay. The recombinant PrM/E polypeptide appeared to be incorporated in the cell membranes as it could be extracted with the nonionic detergent Triton X-100.

Size-exclusion chromatography of the 293 cell-produced PrM/E antigen was performed on an analytical Sepharose 12 column at a flow rate of 0.5 ml/min in 2×PBS containing 0.1% reduced Triton X-100 detergent. As shown in FIG. 6, the PrM/E antigen was found in the peak elution fraction as demonstrated by SDS-PAGE silver stain. The PrM and E antigens eluted together as a complex of approximately five heterodimers. Relative to the molecular weight standards, the elution time of the synthetic PrM/E antigen indicated that it had an estimated molecular weight of 400,000.

To determine the reactivity of the purified PrM/E antigen with various monoclonal antibodies reported to have WNV neutralizing and/or conformational epitopes, the following experiment was conducted. The purified 293-produced PrM/E antigen was treated with 4% dithiothreitol (DTT) for 30 minutes at room temperature and then coated on polystyrene microtiter plates at a concentration of one µg/ml in PBS. Untreated antigen was also coated. The treated and untreated antigen was probed with the WNV monoclonal antibodies described in Table 2 and any bound monoclonal antibody detected with HRP conjugated anti-mouse antibody. The antibodies were from Chemicon International (Temecula, Calif.), BioReliance (Rockville, Md.) and Hennessy Research (Shawnee, Kans.).

Figure 5:
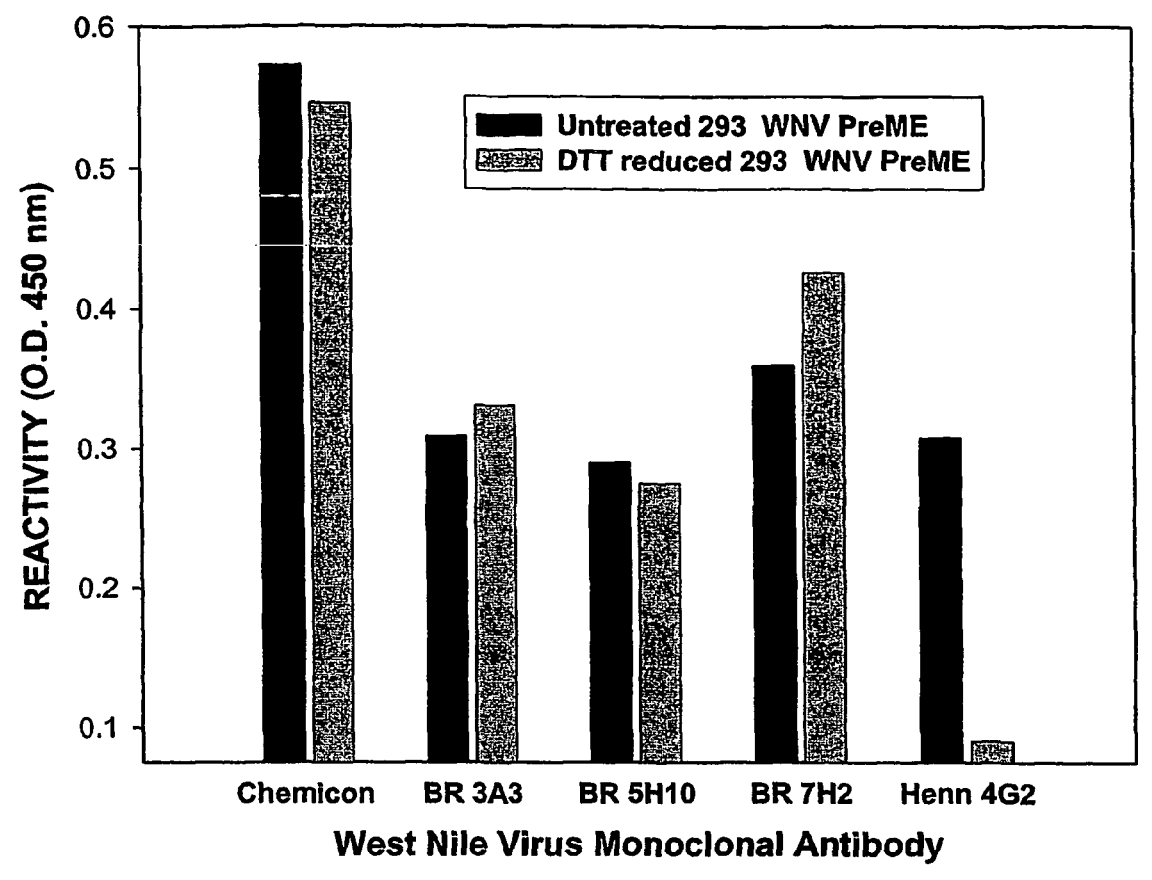

As shown in FIG. 5 and in Table 2, the 293-produced WNV PrM/E antigen bound to 5 different WNV monoclonal antibodies. The three BioReliance monoclonal antibodies, 3A3, 5H10 and 7H2, have been reported to neutralize West Nile Virus. The Hennessy 4G2 monoclonal antibody bound to a conformational or noncontinuous epitope as demonstrated by its lack of binding to DTT-reduced WNV PrM/E antigen. The Chemicon monoclonal antibody is directed against the WNV envelope.

TABLE 2

Reactivity of WNV monoclonal antibodies with 293-produced PrM/E polypeptide

| WNV Monoclonal Antibody | Immunogen used to produce Mab | Reported WNV neutralizing activity | Epitope | Reactivity with 293 produced PrM/E Polypeptide |
|---|---|---|---|---|
| Chemicon 8150 | WNV | TBD | Linear | Positive |
| BioReliance 3A3 | WNV | Positive[a] | Linear[a] | Positive |
| BioReliance 5H10 | WNV | Positive[a] | Linear[a] | Positive |
| BioReliance 7H2 | WNV | Positive[a] | Linear[a] | Positive |
| Hennessy 4G2 | Dengue type 2[b] Virus | TBD | Noncontinuous. Conformational epitope destroyed by DTT | Positive |

[a]Beaseley D et al., J. of Virology (2002) 76: 13097. Reported to bind to the E protein Structural domain III, comprising amino acids 385-415.
[b]Kauman, et al., Am. J Trop Med. Hyg. (1987) 36: 427. Flavivirus E protein-specific monoclonal.

EXAMPLE 3

Insect Cell Expression of WNV Polypeptides

A WNV PrM/E construct was made for insect cell expression. This construct encoded a WNV protein of 73 kDa including the entire WNV membrane precursor protein (amino acids 124-290 of FIG. 2) and the WNV envelope (amino acids 291-791 of FIG. 2) (73 kDa). The protein also included a Glu-Glu Tag fused to the N-terminus. The WNV PrM/E precursor was immunoreactive on Western blots with monoclonal antibodies raised against the envelope protein of Kunjin virus and also with monoclonal antibodies raised against the Glu-Glu Tag. The WNV PrM/E precursor was also processed within the cell host to yield the mature viral envelope as evidenced by the appearance a protein band of approximately 54 kDa that comigrated with the envelope protein of viral particles propagated in Vero cells. This protein band was immunoreactive on Western blots, with monoclonal antibodies raised against the envelope protein of Kunjin virus.

For expression in insect cells, the ATG codon was incorporated as needed and the Glu-Glu Tag (middle T antigen of SV40) and linker nucleotide sequences were included between the tag and WNV genes to facilitate cloning of the fusion proteins. The gene was cloned into pT7Bluebac 4.5 (Invitrogen Life Technologies, Carlsbad, Calif.) utilizing the strong polyhedron promoter for expression during the late stage of infection. Flanking polyhedron sequence provided the genetic regions for homologous recombination of baculoviral wild-type. Production in insect cells was accomplished using standard techniques. See, e.g., Summers and Smith, *Texas Agricultural Experiment Station Bulletin No. 1555* (1987).

EXAMPLE 4

Vaccination of Animals Using WNV Polypeptides

Groups of 10 BALB-C mice were immunized IM on day 0 and 30 and 70 with 2 µg of the purified recombinant WNV PrM/E polypeptide from either HEK293 cells, CHO cells or yeast. MF59C.1 was used as adjuvant. (For a description of MF59, see, International Publication No. WO 90/14837; U.S. Pat. Nos. 6,299,884 and 6,451,325, incorporated herein by reference in their entireties; and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296). Mice were also immunized with 1/10 of a horse dose of West Nile Inovator Equine vaccine (formalin inactivated), a commercial horse vaccine produced by Fort Dodge Animal Health (Wyeth, Overland Park, Kans.). Serum samples were obtained 14 days after the second and third immunizations and antibody response to PrM/E antigen was determined by EIA and by WNV neutralization assay. In particular, EIA antibody assays were performed by using purified WNV PrM/E polypeptide from CHO cells coated on polystyrene microtiter plates. Any bound antibody from diluted mouse sera specimens was detected with anti-mouse HRP conjugate. Plaque reduction WNV neutralization assays were also performed. Serum samples were not heat inactivated prior to assay.

As shown in Tables 3 and 4, ten-fold higher antibody titers were observed with the mammalian cell-produced recombinant PrM/E polypeptide than with the other two vaccines. The PrM/E polypeptide produced in yeast is denatured during the purification process used which may account for its inability to produce neutralizing antibodies in immunized mice.

TABLE 3

Immunogenicity comparison of recombinant PrM/E polypeptide produced 293 cells, CHO cells and S. cerevisiae yeast with a commercial WNV equine vaccine as assessed by EIA.

| Vaccine | Dose[e] | WNV PrM/E EIA antibody titer Post 2nd | | WNV PrM/E EIA antibody titer Post 3rd | |
|---|---|---|---|---|---|
| WNV recombinant PrM/E polypeptide from 293 cells[a] or CHO cells[b]/MF59 | 2 µg | 151<br>356<br>289<br>134<br>251<br>398<br>34<br>165<br>161<br>385 | GMT = 193 +/− 45 | 2,577<br>3,504<br>1,940<br>965<br>659<br>4,075<br>5,034<br>558<br>2,508<br>1,381 | GMT = 1,838 +/− 444 |
| Commercial horse vaccine[d] | 1/10th horse dose | 13<br>6<br>17<br>11<br>13<br>19<br>77<br>13<br>56<br>5 | GMT = 16 +/− 4 | 16<br>17<br>35<br>26<br>27<br>119<br>229<br>26<br>53<br>39 | GMT = 39.7 +/− 10.6 |
| WNV recombinant PrM/E polypeptide from S. cerevisiae yeast/MF59 | 2 µg | —<br>1<br>1<br>—<br>6<br>7<br>—<br>1<br>—<br>3 | GMT = 1.6 +/− 0.4 | 30<br>—<br>1<br>—<br>3,488<br>—<br>—<br>1<br>1<br>500 | GMT = 5.96 +/− 5.7 |

[a]Recombinant WNV PrM/E polypeptide purified from transiently transfected 293 cells was used for the first two immunizations.
[b]Recombinant WNV PrM/E polypeptide purified from stably transfected CHO cells was used for the third immunization.
[d]West Nile Inovator Equine vaccine (formalin inactivated) produced by Fort Dodge Animal Health
[e]Groups of 10 Balb-C mice were immunized IM on 0, 30 and 70 days. Serum samples were taken 14 days after the first two immunizations.

TABLE 4

Immunogenicity comparison of WNV recombinant PrM/E polypeptide produced in HEK 293 or CHO cells and *S. cerevisiae* with commercial WNV equine vaccine as assessed by WNV Plaque Reduction Neutralizing antibody titers.

| Vaccine | Dose[c] | WNV PR Neutralizing antibody titer Post 2nd | | WNV PR Neutralizing antibody titer Post 3rd | |
|---|---|---|---|---|---|
| WNV recombinant PrM/E polypeptide from 293 cells[a] or CHO cells[b]/MF59 | 2 μg | 640 | GMT = 160 | 2,560 | GMT = >1,940 |
| | | 640 | | >5,120 | |
| | | 80 | | 2,560 | |
| | | 10 | | 320 | |
| | | 160 | | 640 | |
| | | 640 | | >5,120 | |
| | | 5 | | 640 | |
| | | 2,560 | | 2,560 | |
| | | 160 | | >5,120 | |
| | | 640 | | 2,560 | |
| Commercial horse vaccine[d] | 1/10th horse dose | 10 | GMT = 15.1 | 10 | GMT = 80 |
| | | 10 | | 40 | |
| | | <5 | | 40 | |
| | | <5 | | 20 | |
| | | 10 | | 160 | |
| | | 10 | | 160 | |
| | | 160 | | 160 | |
| | | 40 | | 160 | |
| | | 640 | | 40 | |
| | | 10 | | 80 | |
| WNV recombinant PrM/E polypeptide from *S. cerevisiae* yeast/MF59 | 2 μg | <5 | GMT = <5 | <5 | |
| | | <5 | | ND | |
| | | <5 | | ND | |
| | | <5 | | <5 | |
| | | <5 | | ND | |
| | | <5 | | ND | |
| | | <5 | | ND | |
| | | <5 | | ND | |
| | | <5 | | <5 | |
| | | <5 | | | |

[a]Recombinant WNV PrM/E polypeptide purified from transiently transfected 293 cells was used for the first two immunizations.
[b]Recombinant WNV PrM/E polypeptide purified from stably transfected CHO cells was used for the third immunization.
[d]West Nile Inovator Equine vaccine (formalin inactivated) produced by Fort Dodge Animal Health
[c]Groups of 10 Balb-C mice were immunized IM on 0, 30 and 70 days. Serum samples were taken 14 days after the first two immunizations.

EXAMPLE 5

Strip Immunoblot Assay (SIA) Using WNV Recombinant PrM/E Polypeptide as Antigen The SIA used was based on the RIBA test (Chiron Corp., Emeryville, Calif.). The membrane consisted of nitrocellulose with an inert plastic backing as support. The strips are generally prepared as follows: the particular antigen or antibody to be attached is coated on a nitrocellulose sheet, the sheet is dried at about 45° C. then blocked with a solution of 1% casein in PBS, dried again at about 45° C. A plastic backing is applied and the sheet is cut into strips. The WNV recombinant PrM/E polypeptide produced intracellularly and purified from CHO cells was applied as a discrete band to nitrocellulose strips at a concentration of 100 ng/strip. This band serves to capture anti-WNV antibodies of all Ig classes (isotypes) present in an infected sample and does not distinguish between the Ig classes. Therefore, in order to provide enhanced sensitivity and to distinguish the class of antibody present, additional bands were coated onto the strip. In particular, 800 ng/strip of a rabbit anti-human IgA antibody, 500 ng/strip of a rabbit anti-human IgM antibody and 800 ng/strip of a rabbit anti-human IgG antibody were also applied to the strip. Finally, two internal controls were present on the strip, one control was monoclonal antibody WNV 5180 (Chemicon International, Temecula, Calif.) at a low level (100 ng/strip) and the other control was monoclonal antibody WNV 5180 at a high level (300 ng/strip). WNV 5180 is a monoclonal antibody directed against the WNV envelope protein. These serve as controls for the binding of the labeled recombinant WNV PrM/E polypeptide used for detection. FIG. 7 shows a diagram of a nitrocellulose strip with the various coated reagents as described above.

The SIA was used to test human plasma samples for the presence of anti-WNV antibodies. The assay procedure was performed as follows. 65 random plasma samples were used initially. These were presumed to be negative for WNV. Additionally, 56 samples were used that had previously tested positive in a standard commercial WNV IgM capture ELISA from PANBIO (Australia). All steps were performed at room temperature. Each strip was numbered and then placed in a well of an 8-well tray. To each well was added 50 μl of human plasma sample to 1 ml of specimen diluent buffer (phosphate-buffered saline (PBS) with bovine protein stabilizers and detergents, 0.1% sodium azide and 0.05% gentamicin sulfate as preservatives). The plates were rocked gently for 2 hours, the solution removed by aspiration, 1 ml of specimen diluent added to each well and the tray was rocked for 15 min. The diluent was then aspirated out and the strips washed 4 times with 1 ml of wash buffer made from wash buffer concentrate (50×) (phosphate-buffered detergent solution with 0.01% thimerosal as a preservative). Residual wash solution was removed by aspiration and 0.5 ml of conjugate solution (horse radish peroxidase (HRP)-labeled WNV PrM/E, with bovine protein stabilizers, containing 0.01% thimerosal as a preservative) at 1:1000 was added to each well. The rack was rocked slowly for 1 hour. The conjugate was removed by aspiration and the strips were washed 2 times with 1 ml each of wash buffer and placed in a RIBA vessel. The strips were washed 2 times with 60 ml of wash buffer in the cup. Residual solution was again removed by aspiration and 10 ml of substrate/developer (4-chloro-1-napthol in methanol/phosphate-buffered hydrogen peroxide per 8 strips) added, followed by rotation for 15 minutes at 110 rpm. The solution was decanted and the strips were washed in distilled water. Developed strips were placed face up on absorbent paper and allowed to dry for 30 minutes in the dark. Strips were read visually or using a RIBA processor (Chiron Corp., Emeryville, Calif.).

FIG. 8 shows representative scoring criteria and FIG. 9 shows the various patterns observed in positive samples. A plasma sample was considered positive only if reactivity was greater than or equal to the low level monoclonal antibody control band, which was defined to represent a 1+ reactivity. A reactivity equivalent to the high level monoclonal antibody control band was considered to represent a reactivity of 3+. Reactivity intensity intermediate between the low and high level monoclonal antibody control bands was considered to be 2+, and reactivity stronger than the high level monoclonal antibody band was considered to be 4+.

Results using the 65 donor plasmas presumed negative were as follows. 64 of the 65 samples were negative by the SIA. Three of these negative samples did give faint +/− results two on the anti-IgM band and one on the anti-IgG band, but were still considered negative. There was one positive SIA result in the 65 presumed negative samples, which showed positive for the anti-IgM band. The positive result was likely due to the presence of WNV antibody from donors that had either previously been infected or that were resolving an infection as IgG and IgM antibody can persist for years.

SIA results using the 56 previously determined positive samples were as follows. All 56 samples reacted with the anti-IgM band, as expected since the commercial assay used to detect positives detects IgM. 55 samples reacted with the WNV recombinant PrM/E polypeptide band, 49 samples with the anti-IgA band and 48 samples with the anti-IgG band. Additional results using 39 seroconversion panels showed 38/39 positive for IgM, 27/39 positive for IgA and 2/39 positive for IgG.

Thus, the strip immunoblot assay was able to simultaneously detect human IgA, IgM and IgG directed against the WNV envelope antigen.

EXAMPLE 6

ELISA Using WNV Recombinant PrM/E Polypeptide Antigen

ELISAs were also performed using the WNV PrM/E antigen produced intracellularly and purified from CHO cells. The ELISA reagents used were from Ortho-Clinical Diagnostics, Raritan, New Jersey. Bloodsamples were from 240 human donors from a region in the Midwest known to have some positive incidences of WNV cases.

In particular, microtiter plate wells were coated with 100 ng/well of the WNV recombinant PrM/E polypeptide in PBS. The wells were washed and blocked using normal Ortho Eci procedures (with an ELISA washer). The washed and blocked wells were dried overnight in vacuo. The dried wells were sealed in moisture-free packets with dessicant and stored at 4° C. until used.

50 µl of sample was added to 150 µl of ELISA specimen diluent to the coated well. The plate was incubated with shaking for 1 hour at 37° C. The solution was aspirated and the wells washed 5 times with Ortho Eci wash buffer. 200 µl of WNV PrM/E-HRP conjugate prepared as in Example 7 was added at 1:10K, diluted in Ortho 3.0 HCV ELISA conjugate diluent.

Plates were incubated with shaking for 1 hour at 37° C. The conjugate was then removed by aspiration, the wells were washed 5 times with Ortho Eci wash buffer and 200 µl of Ortho Eci (chemiluminescent) substrate added. Results were read as relative luminescence units (RLU) after 2 minutes. The cutoff for a positive result was considered to be 1000 RLU. Thus, samples displaying>1000 were considered positive while those<1000 were negative.

Results are shown in Table 5. As can be seen, the ELISA was highly specific (99.58%) with only 1 sample showing an RLU of greater than 1000.

TABLE 5

| RLU | Frequency |
|---|---|
| 0-500 | 238 |
| 501-1000 | 1 |
| 1001-2001 | 0 |
| 2001-3000 | 0 |
| 3001-4000 | 0 |
| 4001-5000 | 0 |

TABLE 5-continued

| RLU | Frequency |
|---|---|
| 5001-6000 | 1 |
| 6001-7000 | 0 |
| More | 0 |
| For 239 donor plasmas: | |
| Avg(RLU) = | 91 |
| StDev(RLU) = | 68 |
| CV(RLU) = | 75 |
| Cutoff(RLU) = | 1000 |
| Specificity | =239/240 donor samples =99.58% |

Figure 10:
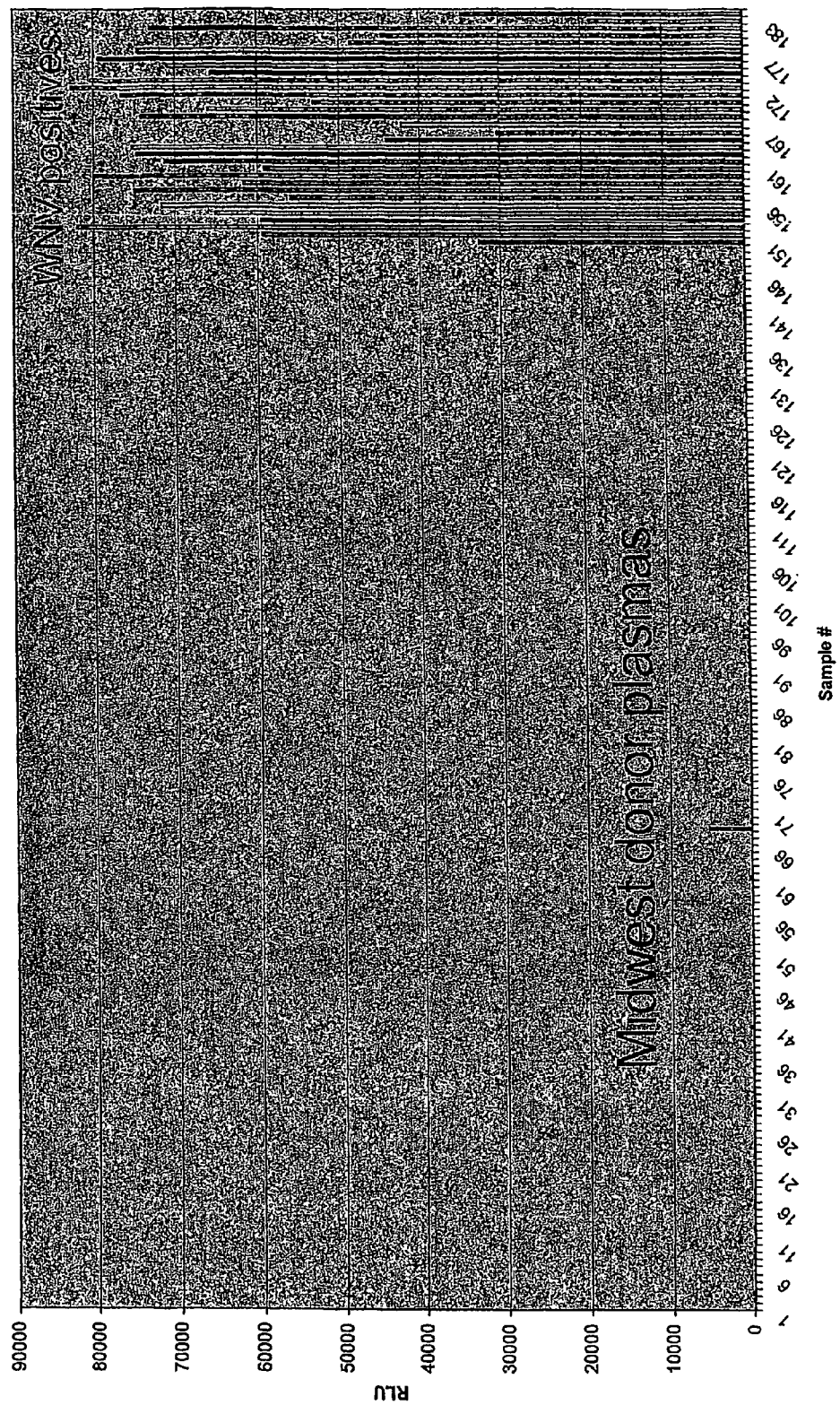
FIG. 10 shows a determination of the sensitivity of the WNV ELISA described in the examples using 32 WNV IgM positive samples.

Another experiment was performed as described above to determine the sensitivity of the WNV ELISA. In this experiment, 32 samples that had tested positive in the PANBIO WNV IgM Capture ELISA were tested using the WNV ELISA described above. As can be seen in FIG. 10, all 32 samples were clearly positive in the WNV ELISA. Moreover, there was a wide separation between the negative samples and the positive samples.

EXAMPLE 7

Detectably Labeled WNV Recombinant PrM/E Polypeptide-PrM/E-HRP Conjugate

The PrM/E-HRP conjugate was produced by modification of the recombinant PrM/E polypeptide with sulfosuccinimidyl 4N-maleimidomethyl cyclohexane-1-carboxylate (sulfo-SMCC, Pierce Chemicals, Dallas, Tex., catalog no. 22322) and modification of the HRP with succinimidyl 6-(3-[2-pyridyldithio]-propionamido)hexanoate (LC-SPDP, Pierce Chemicals, Dallas, Tex., catalog no. 21651) followed by dithiothreitol activation. After separation of excess reagent, the two proteins were combined to allow conjugation. The conjugation was verified by SDS-PAGE analysis of the products and the conjugate was used with no further purification.

EXAMPLE 8

Figure 11:
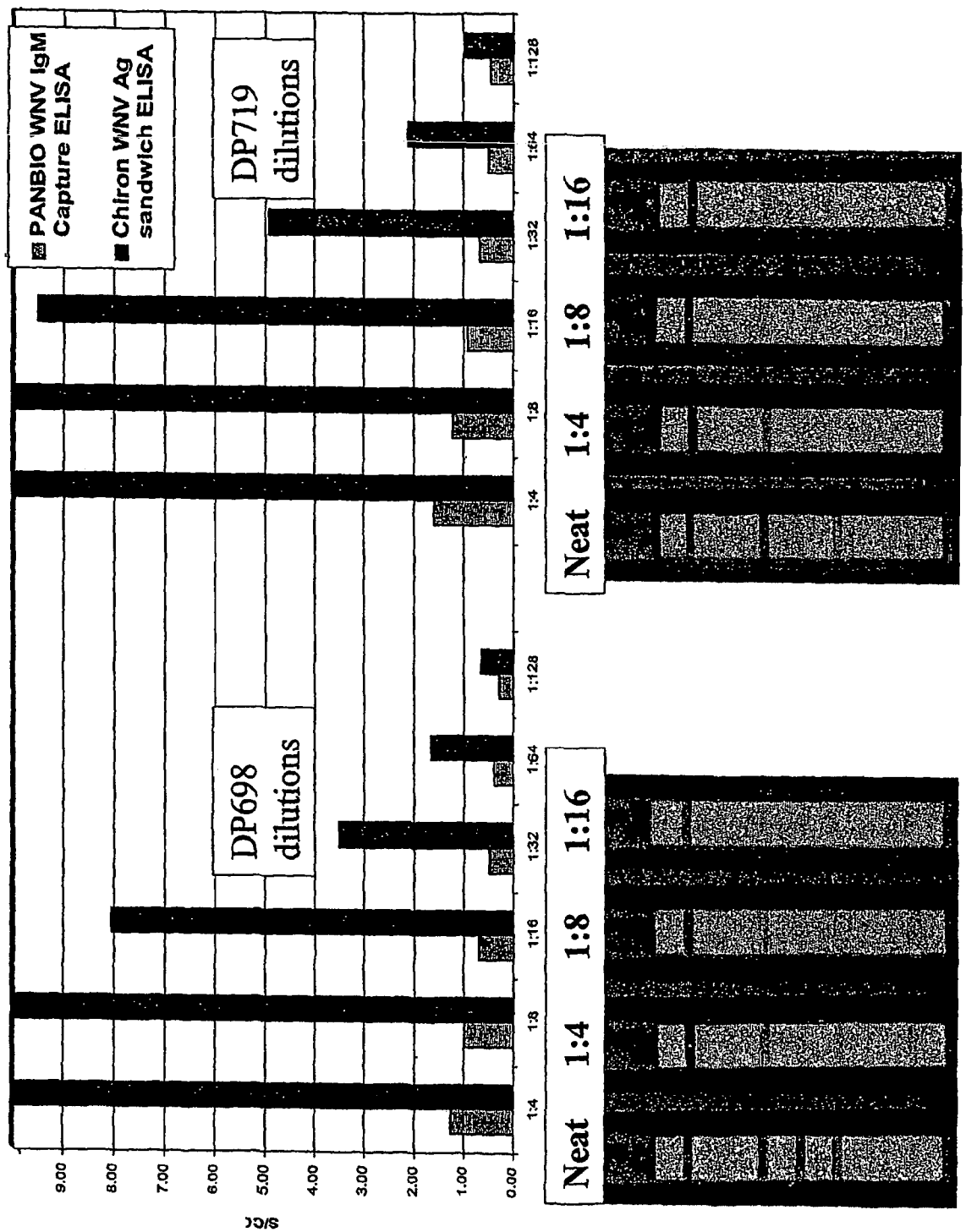
FIG. 11 shows the results of a comparison of a commercially available ELISA with the WNV ELISA and SIA Using the PrM/E Antigen of the invention.

Comparison of Commercial ELISA with the WNV ELISA and SIA Using the Recombinant PrM/E Polypeptide as Antigen In order to compare the sensitivity of the above-described SIA and ELISA which used the intracellularly produced recombinant PrM/E polypeptide, the following experiment was conducted. Two human plasma samples, DP698 and DP719, that had tested positive in the commercial WNV IgM ELISA from Focus Technologies (Cypress, Calif.) but negative on the same company's WNV IgG assay, were used in the SIA and ELISA assays described above, as well as in the commercial WNV IgM Capture ELISA from PANBIO (Australia). This assay only measures the IgM class of immunoglobulins. Results are shown in FIG. 11.

As can be seen, the WNV ELISA assay of the present invention was more sensitive than the PANBIO IgM Capture ELISA. Moreover, the strip immunoassay of the present invention was at least as sensitive on the IgM band as the PANBIO assay.

EXAMPLE 9

Immunogenicity Comparison of Recombinant CHO-Derived WNV PrM/E Heterodimer Complex with Commercial WNV Equine Vaccine as Assessed by WNV PrM/E Heterodimer Complex EIA Antibody Titers in Mice Groups of 10 mice were immunized IM as described at 0, 30 and 90 days with PrM/E heterodimer complex or West Nile Innovator Equine vaccine (formalin inactivated) produced by Fort Dodge Animal Health Serum samples were taken 14 days after the last two immunizations. Results are shown in Table 6.

TABLE 6

| Vaccine | Dose[c] | WNV PrM/E EIA Geometric mean antibody titers Post 2nd | WNVPrM/E EIA Geometric Mean antibody titers Post 3rd |
| --- | --- | --- | --- |
| Recombinant WNV CHO PrM/E heterodimer complex/MF59 | 7.5 µg | 9,536 +/− 622 | 11,738 +/− 791 |
| | 2.5 µg | 7,988 +/− 1,105 | 13,930 +/− 1,930 |
| Recombinant WNV CHO PrM/E heterodimer complex/Alum | 2.5 µg | 639 +/− 03 | 1,835 +/− 257 |
| Commercial horse vaccine[d] | 1/10th horse dose | 52 +/− 12 | 135 +/− 27 |

EXAMPLE 10

Immunogenicity Comparison of Recombinant CHO-Derived WNV PrM/E Heterodimer Complex with Alum vs MF59 as Assessed by WNV Neutralizing Antibody Titers Groups of 10 mice were immunized IM as described at 0, 30 and 90 days with PrM/E heterodimer complex. Serum samples were taken 14 days after the last two immunizations. Results are shown in Table 7.

TABLE 7

| Vaccine | Dose[c] | WNV Neutralizing Geometric mean antibody titers Post 2nd | WNV Neutralizing Geometric Mean antibody titers Post 3rd |
| --- | --- | --- | --- |
| Recombinant WNV CHO PrM/E heterodimer complex/MF59 | 2.5 µg | 4,456 | >5,120 |
| Recombinant WNV CHO PrM/E heterodimer complex/Alum | 2.5 µg | 845 | 2,559 |

EXAMPLE 11

Immunogenicity Comparison of Recombinant CHO-Derived WNV PrM/E Heterodimer Complex and a Commercial WNV Equine Vaccine as Assessed by WNV EIA and Neutralizing Antibody Titers in Hamsters Groups of 10 Hamsters were immunized IM as described at 0, 30 and 90 days with the indicated doses of PrM/E heterodimer complex prepared as described from stably transfected CHO cells. Serum samples were taken 14 days after the last two immunizations. Immunogenicity of the PrM/E heterodimer complex was compared to a commercial horse vaccine diluted to 1/10th strength. The horse vaccine was West Nile Innovator Equine vaccine (formalin inactivated) produced by Fort Dodge Animal Health. Results are shown below in Table 8. Antibody titers represent Geometric Mean titers (GMT) against West Nile Virus PrM/E heterodimer complex antigen following collection of sera 14 d after the 2nd and 3rd immunizations.

EIA Results are shown in Table 8 and Neutralizing titers are shown in Table 9.

TABLE 8

| Vaccine | Dose[c] | WNV PrM/E EIA antibody titer Post 2nd | | WNV PrM/E EIA antibody titer Post 3rd | |
| --- | --- | --- | --- | --- | --- |
| Recombinant WNV CHO PrM/E heterodimer complex/MF59 | 7.5 µg | 5,396 | GMT = 2,725 | 2,500 | GMT = 3,873 |
| | | 3,091 | | 5,240 | |
| | | 2,884 | | 9,780 | |
| | | 776 | | 1,099 | |
| | | 4,594 | | 5,146 | |
| | | 633 | | 3,828 | |
| | | 5,028 | | 4,267 | |
| | | 2,347 | | 2,485 | |
| | | 2,736 | | 4,301 | |
| Recombinant WNV CHO PrM/E heterodimer complex/MF59 | 20 µg | 2,584 | GMT = 1,888 | 2,675 | GMT = 4,085 |
| | | 2,687 | | 3,868 | |
| | | 4,846 | | 3,748 | |
| | | 2,251 | | 10,272 | |
| | | 2,384 | | 2,431 | |
| | | 1,547 | | 4,188 | |
| | | 3,111 | | 7,688 | |
| | | 603 | | 9,448 | |
| | | 437 | | 896 | |
| | | 2,515 | | 4,903 | |
| Recombinant WNV CHO PrM/E heterodimer complex/Alum | 7.5 µg | 4,613 | GMT = 3,483 | 5,536 | GMT = 6,351 |
| | | 5,548 | | 7,014 | |
| | | 4,577 | | 13,701 | |
| | | 2,181 | | 3,420 | |
| | | 5,084 | | 10,835 | |
| | | 2,896 | | 8,835 | |
| | | 3,982 | | 5,597 | |
| | | 2,587 | | 4,586 | |
| | | 2,486 | | 5,030 | |
| | | 2,725 | | 4,910 | |
| Commercial horse vaccine[d] | 1/10th horse dose | 635 | GMT = 528 | 1,149 | GMT = 998 |
| | | 345 | | 958 | |
| | | 1,064 | | 1,717 | |
| | | 367 | | 1,010 | |
| | | 552 | | 2,125 | |
| | | 569 | | 404 | |
| | | 364 | | 668 | |
| | | 579 | | 700 | |
| | | 620 | | 1,161 | |
| | | 479 | | 1,101 | |

TABLE 9

| Vaccine | Dose[c] | WNV Neutralizing antibody titer Post 2nd | WNV Neutralizing antibody titer Post 3rd |
|---|---|---|---|
| Recombinant WNV CHO PrM/E heterodimer complex/ MF59 | 7.5 μg | 640<br>80<br>640 GMT =<br>640 394<br>160<br>640<br>160<br>640<br>640<br>640 | 640<br>640<br>640 GMT =<br>640 493<br>80<br>320<br>640<br>640<br>640<br>1,280 |
| Recombinant WNV CHO PrM E Antigen/ Alum | 7.5 μg | 5,120<br>320<br>2,560 GMT =<br>640 910<br>640<br>640<br>2,560<br>640<br>640 | 2,560<br>160<br>2,560 GMT =<br>640 845<br>2,560<br>640<br>640<br>640<br>640 |
| Commercial horse vaccine[d] | 1/10th horse dose | 640<br>160<br>640 GMT =<br>320 394<br>640<br>640<br>640<br>160<br>640<br>640 | 640<br>160<br>640 GMT =<br>160 197<br>640<br>40<br>160<br>80<br>160<br>160 |

Comparisons: 0.300 (between first two Post 3rd GMTs); P = 0.001 (between second and third groups).

As can be seen in comparisons of Tables 6-9, immunizations with recombinant PrM/E heterodimer complex and MF59 increased the antibody response in mice but not in hamsters.

Thus, recombinant WNV immunogens, methods of preparing the immunogens and use of the immunogens for diagnosis, prevention and treatment of WNV infection is described. Although preferred embodiments of the subject invention have been described in some detail, it is understood that obvious variations can be made without departing from the spirit and the scope of the invention as defined by the appended claims.

We claim:

1. An isolated immunogenic composition comprising a complex of at least 4 West Nile Virus (WNV) PrM/E heterodimers, each heterodimer consisting of (i) a recombinant WNV PrM polypeptide and (ii) a recombinant WNV E polypeptide, wherein the complex is purified from a mammalian cell, and further wherein the composition comprising the purified WNV PrM/E complex is substantially free of free WNV M polypeptide.

2. The immunogenic composition of claim 1, wherein said recombinant PrM polypeptide comprises an amino acid sequence exhibiting at least 90% sequence identity to the contiguous sequence of amino acids depicted at positions 124-290 of SEQ ID NO:2.

3. The immunogenic composition of claim 1, wherein said recombinant E polypeptide comprises an amino acid sequence exhibiting at least 90% sequence identity to the contiguous sequence of amino acids depicted at positions 291-791 of SEQ ID NO:2.

4. The immunogenic composition of claim 1, wherein said recombinant WNV PrM polypeptide comprises the contiguous sequence of amino acids depicted at positions 124-290 of SEQ ID NO:2.

5. The immunogenic composition of claim 1, wherein said recombinant WNV E polypeptide comprises the contiguous sequence of amino acids depicted at positions 291-791 of SEQ ID NO:2.

6. The immunogenic composition of claim 1, wherein said recombinant WNV PrM polypeptide comprises the contiguous sequence of amino acids depicted at positions 124-290 of SEQ ID NO:2 and said recombinant WNV E polypeptide comprises the contiguous sequence of amino acids depicted at positions 291-791 of SEQ ID NO:2.

7. The immunogenic composition of claim 1, further comprising an adjuvant.

8. The immunogenic composition of claim 7 wherein the adjuvant is selected from the group consisting of Alum, MF-59, CpG, and ISCOMS.

9. The immunogenic composition of claim 8, wherein the adjuvant is alum.

10. The immunogenic composition of claim 8, wherein the adjuvant is MF-59.

11. The immunogenic composition claim 1, which further comprises a pharmaceutically acceptable carrier vehicle.

12. A method of immunizing an animal against the West Nile Virus which comprises administering to said animal an immunogenic composition of claim 1.

13. An immunogenic composition comprising a purified complex of at least 4 West Nile Virus (WNV) PrM/E heterodimers, each heterodimer consisting of a recombinant WNV PrM polypeptide and (ii) a recombinant WNV E polypeptide wherein the composition comprising the purified complex is substantially free of free WNV M polypeptide obtained by the method comprising:

(a) culturing a population of mammalian host cells comprising a recombinant polynucleotide vector comprising a nucleic acid encoding a WNV polyprotein, wherein said nucleic acid encodes, in 5'-3' order, a eukaryotic leader sequence, a WNV PrM polypeptide, a WNV E polypeptide and a translational stop codon, under conditions that provide for intracellular expression of recombinant PrM/E polypeptide;

(b) recovering an insoluble portion from the cells, wherein the insoluble portion contains substantially all of the membrane component of the cells;

(c) treating the insoluble portion with a non-ionic detergent, thereby to solubilize the membrane component and release the PrM/E polypeptide; and (d) purifying the released PrM/E polypeptide, to provide a composition comprising said purified complex substantially free of free WNV M polypeptide.

14. A vaccine comprising the immunogenic composition of claim 1.

15. A method of detecting WNV antibodies in a biological sample, comprising:
   (a) reacting said biological sample with the immunogenic composition of claim 1 under conditions which allow WNV antibodies, when present in the biological sample, to bind to said composition to form an antibody/antigen complex; and
   (b) detecting the presence or absence of said antibody/antigen complex,
   thereby detecting the presence or absence of WNV antibodies in said sample.

16. An immunodiagnostic test kit for detecting WNV infection, said test kit comprising the immunogenic composition of claim 1 and instructions for conducting the immunodiagnostic test.

17. A solid support comprising the immunogenic composition comprising at least one WNV PrM/E complex according to claim 1.

18. A solid support comprising the immunogenic composition comprising at least one WNV PrM/E complex according to claim 1 and at least one anti-human immunoglobulin antibody, wherein the PrM/E complex and the anti-human immunoglobulin antibody are immobilized in discrete positions on the solid support.

19. The solid support of claim 18, wherein the at least one anti-human immunoglobulin antibody is selected from the group consisting of an anti-human IgM antibody, an anti-human IgG antibody and an anti-human IgA antibody.

20. The solid support of claim 19, wherein the solid support comprises an anti-human IgM antibody and an anti-human IgG antibody immobilized in discrete positions thereon.

21. The solid support of claim 20, wherein the solid support further comprises an anti-human IgA antibody immobilized in a discrete position on the solid support.

22. The solid support of claim 18, further comprising at least two internal controls, wherein one of the controls defines the lower detection limit for a positive result in an immunoassay using the solid support and the other control defines a highly positive result in an immunoassay using the solid support.

23. The solid support of claim 22, wherein the at least two internal controls comprise first and second monoclonal antibodies directed against a WNV envelope antigen.

24. The solid support of claim 23, wherein the first and second monoclonal antibodies are the same monoclonal antibody.

25. The solid support of claim 17, wherein the solid support is a nitrocellulose strip.

26. A nitrocellulose support comprising:
   (a) the immunogenic composition comprising at least one WNV PrM/E complex according to claim 1;
   (b) at least one anti-human IgM antibody;
   (c) at least one anti-human IgG antibody;
   (d) at least one anti-human IgA antibody; and
   (e) at least two internal controls, wherein one of the controls is an anti-WNV envelope monoclonal antibody that defines a lower detection limit for a positive result in a strip immunoblot assay using the nitrocellulose support, and the other control is an anti-WNV envelope monoclonal antibody that defines a highly positive result in a strip immunoblot assay using the nitrocellulose support;
   wherein the immunogenic composition, the anti-human IgM antibody, the anti-human IgG antibody, the anti-human IgA antibody, and the at least two internal controls are each immobilized in discrete positions on said nitrocellulose support.

27. A method of detecting the presence of WNV antibodies in a biological sample, said method comprising:
   (a) providing a biological sample;
   (b) providing a solid support according to claim 17;
   (c) contacting said biological sample with said solid support, under conditions which allow WNV antibodies, if present in the biological sample, to bind with at least the WNV PrM/E heterodimer to form an antibody/antigen complex; and
   (d) detecting the presence of the antibody/antigen complex, thereby detecting the presence of WNV antibodies in the biological sample.

28. The method of claim 27, further comprising:
   (e) removing unbound WNV antibodies;
   (f) providing one or more moieties capable of associating with said antibody/antigen complex; and
   (g) detecting the presence of said one or more moieties,
   thereby detecting the presence of WNV antibodies in the biological sample.

29. The method of claim 28, wherein said one or more moieties comprises a detectably labeled WNV PrM/E heterodimer.

30. The method of claim 29, wherein the detectable label is an enzyme.

31. The method of claim 27, wherein said biological sample is from a human blood sample.

32. A method of detecting WNV antibodies in a biological sample, said method comprising:
   (a) providing a biological sample from a human blood sample;
   (b) providing a nitrocellulose support according to claim 26;
   (c) contacting said biological sample with said nitrocellulose support, under conditions which allow WNV antibodies, if present in the biological sample, to bind with at least the WNV PrM/E heterodimer to form an antibody/antigen complex;
   (d) removing unbound antibodies;
   (e) providing a detectably labeled WNV PrM/E heterodimer, under conditions which allow binding to any bound WNV antibodies;
   (f) removing unbound detectably labeled WNV PrM/E heterodimer; and
   (g) detecting the presence of said bound detectable label, thereby detecting the presence of WNV antibodies in the biological sample.

33. A method of identifying the immunoglobulin class of a WNV antibody present in a biological sample containing WNV, said method comprising:
   (a) providing a biological sample derived from a human blood sample;
   (b) providing a nitrocellulose support according to claim 26;
   (c) contacting said biological sample with said nitrocellulose support, under conditions which (i) allow WNV antibodies in the biological sample to bind with the immobilized WNV PrM/E heterodimer to form an antibody/antigen complex, and (ii) allow WNV antibodies present in the biological sample to bind to at least one of the immobilized anti-IgG, anti-IgM and/or anti-IgA immunoglobulins;
   (d) removing unbound WNV antibodies;
   (e) providing a detectably labeled WNV PrM/E heterodimer under conditions that allow binding of the labeled WNV PrM/E heterodimer to any bound WNV antibodies;

(f) removing any unbound labeled heterodimer; and
(g) detecting the presence of said detectable label,
thereby identifying the immunoglobulin class of WNV antibody present in the biological sample.

34. An immunodiagnostic test kit for detecting WNV, said test kit comprising:
(a) a solid support according to claim 17; and
(b) instructions for conducting the immunodiagnostic test.

35. An immunodiagnostic test kit for detecting WNV, said test kit comprising:
(a) a nitrocellulose support according to claim 26; and
(b) instructions for conducting the immunodiagnostic test.

36. A method of detecting the presence of WNV antibodies in a human biological sample, said method comprising:
(a) providing a human biological sample;
(b) providing a solid support comprising anti-human immunoglobulin antibody;
(c) contacting said biological sample with said solid support, under conditions which allow WNV antibodies, if present in the biological sample, to bind with the anti-human immunoglobulin antibody to form an antibody/antibody complex,
(d) removing any unbound WNV antibodies;
(e) providing a detectably labeled immunogenic composition according to claim 1, under conditions which allow binding to any bound WNV antibodies; and
(f) detecting the presence of the bound labeled immunogenic composition,
thereby detecting the presence of WNV antibodies in the biological sample.

37. The immunogenic composition of claim 1, wherein said recombinant WNV PrM polypeptide comprises an amino acid sequence exhibiting at least 95% sequence identity to the contiguous sequence of amino acids depicted at positions 124-290 of SEQ ID NO:2.

38. The immunogenic composition of claim 1, wherein said recombinant WNV PrM polypeptide comprises an amino acid sequence exhibiting at least 95% sequence identity to the contiguous sequence of amino acids depicted at positions 291-791 of SEQ ID NO:2.

* * * * *